United States Patent
Cruse et al.

(10) Patent No.: US 9,290,520 B2
(45) Date of Patent: Mar. 22, 2016

(54) CYCLIC DIOL-DERIVED BLOCKED MERCAPTOFUNCTIONAL SILANE COMPOSITIONS

(71) Applicants: Richard W Cruse, Yorktown Heights, NY (US); Leda N. Gonzalez, Norwalk, CT (US); Rodica Himmeldirk, Vincent, OH (US); Larry Allen Divens, Parkersburg, WV (US); Melinda Jackson, Belmont, WV (US); Eric Raymond Pohl, Mount Kisco, NY (US); Antonio Chaves, Chappaqua, NY (US)

(72) Inventors: Richard W Cruse, Yorktown Heights, NY (US); Leda N. Gonzalez, Norwalk, CT (US); Rodica Himmeldirk, Vincent, OH (US); Larry Allen Divens, Parkersburg, WV (US); Melinda Jackson, Belmont, WV (US); Eric Raymond Pohl, Mount Kisco, NY (US); Antonio Chaves, Chappaqua, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 255 days.

(21) Appl. No.: 14/088,825

(22) Filed: Nov. 25, 2013

(65) Prior Publication Data

US 2014/0076202 A1 Mar. 20, 2014

Related U.S. Application Data

(60) Continuation of application No. 12/916,885, filed on Nov. 1, 2010, now Pat. No. 8,609,877, which is a division of application No. 11/208,367, filed on Aug. 19, 2005, now Pat. No. 7,928,258, which is a continuation-in-part of application No. 10/922,426, filed on Aug. 20, 2004, now abandoned.

(51) Int. Cl.
  *C07F 7/18* (2006.01)
  *C07F 7/08* (2006.01)
  *C08K 5/54* (2006.01)
  *C08K 5/549* (2006.01)
  *C08L 9/06* (2006.01)

(52) U.S. Cl.
  CPC .................. *C07F 7/0818* (2013.01); *C07F 7/18* (2013.01); *C07F 7/1836* (2013.01); *C08K 5/54* (2013.01); *C08K 5/549* (2013.01); *C08L 9/06* (2013.01)

(58) Field of Classification Search
  CPC ........................................ C07F 7/18
  USPC ........................................ 556/406
  See application file for complete search history.

(56) References Cited

U.S. PATENT DOCUMENTS

| | | | |
|---|---|---|---|
| 6,753,438 B2 * | 6/2004 | Taylor | C08G 77/08 524/779 |
| 6,777,569 B1 * | 8/2004 | Westmeyer | C07F 7/1892 556/427 |

* cited by examiner

*Primary Examiner* — Elvis O Price
(74) *Attorney, Agent, or Firm* — James C. Abruzzo

(57) ABSTRACT

Diol derived blocked mercaptofunctional silane compositions in which the silanes comprise cyclic and bridged alkoxy groups derived from hydrocarbon-based diols and processes for their preparation are provided. Also provided are rubber compositions comprising the cyclic diol-derived blocked mercaptofunctional silanes, processes for their preparation and articles of manufacture comprising the rubber compositions, in particular, automotive tires and components thereof.

15 Claims, No Drawings

CYCLIC DIOL-DERIVED BLOCKED MERCAPTOFUNCTIONAL SILANE COMPOSITIONS

CROSS-REFERENCE TO RELATED APPLICATIONS

This application is a continuation of U.S. patent application Ser. No. 12/916,885 filed Nov. 1, 2010, which is a divisional of U.S. patent application Ser. No. 11/208,367, filed Aug. 19, 2005 now issued as U.S. Pat. No. 7,928,258, which is a continuation-in-part of U.S. patent application Ser. No. 10/922,426, filed Aug. 20, 2004, now abandoned, the entire contents of which are incorporated by reference herein.

BACKGROUND OF THE INVENTION

1. Field of the Invention

The present invention generally relates to the cyclic diol-derived blocked mercaptofunctional silane compositions, processes for their preparation, and rubber compositions comprising same.

2. Description of Related Art

A number of ether-based diol derivatives of sulfur silanes are known in the art that suffer from a tendency to yield bridged structures in favor of cyclic structures exclusively or primarily, leading to high viscosities and gellation, which limits their usefulness in elastomer manufacture. These silanes and their use further suffer from the hazards associated with the use of ethers, which have a tendency to form peroxides spontaneously, thereby presenting a substantial flammability risk and possibly interfering with the use of these silanes as coupling agents.

Also described in the prior art are blocked mercaptofunctional silanes, such as thiocarboxylate-functional silanes, processes for their preparation and their use in rubber compositions. A presentation on the subject was also given at the 2002 International Tire Exposition and Conference (ITEC) in Akron, Ohio. This art generally describes thiocarboxylate-functional silanes whose hydrolysable groups are derived from simple monofunctional alcohols.

The prior art also describes processes for the preparation of cyclic alkoxysilanes by reacting difunctional and trifunctional alkoxysilanes or silazanes with glycols or other diols to form cyclic monomers. These silanes however tend to self-polymerize to high viscosity polymeric materials.

The prior art also describes the kinetics and mechanisms of substitution reactions at the thiocarboxyl function in which the rate of alcoholysis of a thiol ester should be higher than the rate of thiolysis of an ester. This means that the reaction equilibrium will favor the replacement of the thiol group with the alcohol group.

The prior art does not address the use of cyclic diol-derived blocked mercapto functional silane compositions with reduced volatile organic compound ("VOC") emissions. Accordingly, there exists a need for improved silanes.

BRIEF DESCRIPTION OF THE INVENTION

Silane compositions are provided herein comprising cyclic dialkoxy haloalkyl silanes and cyclic dialkoxy thiocarboxylate silane compositions. These silanes are derived from diols and release diols during use, as opposed to the ethanol released during the use of the thiocarboxylate silanes and/or polysulfide silanes used in the prior art. The diols are very resistant to volatilization owing to their low volatility, thereby resulting in a substantially reduced level of VOC emissions during use.

Accordingly, in a first embodiment of the present invention, a cyclic and bridging dialkoxy silane composition is provided comprising at least one component selected from the group consisting of:

$$[[[(ROC(=O))_p\text{-}(G)_j]_k\text{-}Y\text{—}S]_r\text{-}G\text{-}(SiX_uZ^b_v,Z^c_w)_s]_n,$$
and
$$[[(Z^c_wZ^b_v,X_uSi)_q\text{-}G]_a\text{-}[Y\text{—}[S\text{-}G\text{-}SiX_uZ^b_v,Z^c_w]_b]_c]_n,$$

wherein
each occurrence of Y is independently selected from a polyvalent species $(Q)_zA(=E)$, wherein the atom (A) attached to an unsaturated heteroatom (E) is attached to a sulfur, which in turn is linked via a group G to a silicon atom;

each occurrence of R is independently selected from the group consisting of hydrogen, straight, cyclic or branched alkyl that may or may not contain unsaturation, alkenyl groups, aryl groups, and aralkyl groups, with each R, other than hydrogen, containing from 1 to about 18 carbon atoms;

each occurrence of G is independently selected from the group consisting of monovalent and polyvalent groups derived by substitution of alkyl, alkenyl, aryl, or aralkyl wherein G can comprise from 1 to about 30 carbon atoms, with the proviso that if G is univalent, G can be hydrogen;

each occurrence of $Z^b$, which forms a bridging structure between two silicon atoms, is independently selected from the group consisting of $(\text{—O—})_{0.5}$ and $[\text{—O}(R^4CR^5)_fO\text{—}]_{0.5}$, wherein each occurrence of $R^4$ and $R^5$ is independently R;

each occurrence of $Z^c$, which forms a cyclic structure with a silicon atom, is independently given by $\text{—O}(R^4CR^5)_fO\text{—}$; wherein each occurrence of $R^4$ and $R^5$ is independently R;

each occurrence of X is independently selected from the group consisting of —Cl, —Br, $R^1O$—, $R^1O(R^4CR^5)_fO$—, $R^1C(=O)O$—, $R^1R^2C=NO$—, $R^1R^2NO$—, $R^1R^2N$—, $\text{—}R^1$, and $\text{—}(OSiR^1R^2)_t(OSiR^1R^2R^3)$, wherein each occurrence of $R^1$, $R^2$, $R^3R^4$ and $R^5$ is independently R;

each occurrence of Q is independently selected from oxygen, sulfur or (—NR—);

each occurrence of A is independently selected from carbon, sulfur, phosphorus or sulfonyl;

each occurrence of E is independently selected from oxygen, sulfur or (—NR—);

each occurrence of the subscripts, u, n, v, w, f, p, r, z, q, a, b, j, p, c, t, s, and k, is independently given by u is 0 to about 3; n is 1 to about 100, with the proviso that when n is greater than 1, v is greater than 0 and all the valences for $Z^b$ have a silicon atom bonded to them; v is 0 to about 3; w is 0 to about 1; u+v+2w is 3; f is 1 to about 15; p is 0 to about 5; r is 1 to about 3; z is 0 to about 2; q is 0 to about 6; a is 0 to about 7; b is 1 to about 3; j is 0 to about 1, but it may be 0 only if p is 1, c is 1 to about 6; t is 0 to about 50; s is 1 to about 3; and k is 1 to about 2, with the provisos that (I) if A is carbon, sulfur, or sulfonyl, then (i) a+b is 2 and (ii) k is 1; (II) if A is phosphorus, then a+b is 3 unless both (i) c is greater than 1 and (ii) b is 1, in which case a is c+1; and (III) if A is phosphorus, then k is 2; and wherein that each of the above structures comprise at least one hydrolysable group, $Z^b$ or $Z^c$, that is a difunctional alkoxy group.

In a second embodiment of the present invention, a process for the preparation of a cyclic and bridging dialkoxy blocked mercaptofunctional silane composition is provided comprising reacting an aqueous solution of a salt of at least one thiocarboxylate acid with at least one cyclic and bridging dialkoxy haloalkyl silane and, optionally, at least one haloalkyl silane, in the presence or absence of at least one phase transfer catalyst. In one embodiment, the cyclic and bridging dialkoxy haloalkyl silanes and haloalkyl silanes are, respectively, of the structures:

$$L_r\text{-}G\text{-}(SiX_u Z^b_v Z^c_w)_s, \text{ and}$$

$$L_r\text{-}G\text{-}(SiX_3)_s$$

and the structures for the thiocarboxylate salts are:

$$G(\text{-}Y^1\text{---}SM)_d$$

$$[(ROC(=O))_p\text{-}(G)_j]\text{-}Y^1\text{---}SM \text{ or}$$

$$[(Z^c_w Z^b_v X_u Si)_q\text{-}G]\text{-}Y^1\text{---}SM].$$

wherein
  each occurrence of M is independently selected from alkali metal; ammonium; or mono-, di-, or tri-substituted ammonium;
  each occurrence of $Y^1$ is independently carbonyl; and d is 1 to about 6 and R, L, G, X, $Z^b$, $Z^c$, j, p, q, u, v, w, r, and s have the aforestated meanings.

In accordance with a third embodiment of the present invention, a rubber composition is provided comprising (a) a rubber component; (b) a filler and (c) at least one cyclic and bridging dialkoxy blocked mercaptofunctional silane composition comprising at least one component selected from the group consisting of $$[[[(ROC(=O))_p\text{-}(G)_j]_k\text{-}Y\text{---}S]_r\text{-}G\text{-}(SiX_u Z^b_v Z^c_w)_s]_n,$$
and $$[[(Z^c_w Z^b_v X_u Si)_q\text{-}G]_a\text{-}[Y\text{---}[S\text{-}G\text{-}SiX_u Z^b_v Z^c_w]_b]_c]_n,$$

wherein R, G, Y, X, $Z^b$, $Z^c$, u, v, w, f, p, r, z, q, a, b, j, c, t, s, k and n have the aforestated meanings, and wherein that each of the above structures comprise at least one hydrolysable group, $Z^b$ or $Z^c$, that is a difunctional alkoxy group.

In accordance with a fourth embodiment of the present invention, a process for preparing a rubber composition is provided comprising adding to a rubber composition reaction-forming mixture an effective amount of at least one cyclic and bridging dialkoxy blocked mercaptofunctional silane composition comprising at least one component selected from the group consisting of:

$$[[[(ROC(=O))_p\text{-}(G)_j]_k\text{-}Y\text{---}S]_r\text{-}G\text{-}(SiX_u Z^b_v Z^c_w)_s]_n,$$
and $$[[(Z^c_w Z^b_v X_u Si)_q\text{-}G]_a\text{-}[Y\text{---}[S\text{-}G\text{-}SiX_u Z^b_v Z^c_w]_b]_c]_n,$$

wherein R, G, Y, X, $Z^b$, $Z^c$, u, v, w, f, p, r, z, q, a, b, j, c, t, s, k and n have the aforestated meanings, and wherein that each of the above structures comprise at least one hydrolysable group, $Z^b$ or $Z^c$, that is a difunctional alkoxy group.

In accordance with a fifth embodiment, the present invention, an article of manufacture, in particular tires and tire treads, is provided comprising at least one cyclic and bridging dialkoxy silane composition comprising at least one component selected from the group consisting of:

$$[[[(ROC(=O))_p\text{-}(G)_j]_k\text{-}Y\text{---}S]_r\text{-}G\text{-}(SiX_u Z^b_v Z^c_w)_s]_n,$$
and $$[[(Z^c_w Z^b_v X_u Si)_q\text{-}G]_a\text{-}[Y\text{---}[S\text{-}G\text{-}SiX_u Z^b_v Z^c_w]_b]_c]_n,$$

wherein R, G, Y, X, $Z^b$, $Z^c$, u, v, w, f, p, r, z, q, a, b, j, c, t, s, k and n have the aforestated meanings, and wherein that each of the above structures comprise at least one hydrolysable group, $Z^b$ or $Z^c$, that is a difunctional alkoxy group.

DETAILED DESCRIPTION OF THE INVENTION

Cyclic and Bridging Dialkoxy Haloalkyl Silane and Cyclic and Bridging Dialkoxy Blocked Mercaptofunctional Silane Compositions: Silane Structures In one embodiment of the present invention, cyclic and bridging dialkoxy blocked mercaptofunctional silanes are provided as represented by the general formulae (1-2):

$$[[[(ROC(=O))_p\text{-}(G)_j]_k\text{-}Y\text{---}S]_r\text{-}G\text{-}(SiX_u Z^b_v Z^c_w)_s]_n \quad \text{(Formula 1)}$$

$$[[(Z^c_w Z^b_v X_u Si)_q\text{-}G]_a\text{-}[Y\text{---}[S\text{-}G\text{-}SiX_u Z^b_v Z^c_w]_b]_c]_n \quad \text{(Formula 2)}$$

In another embodiment of the present invention, cyclic and bridging dialkoxy haloalkyl silane compositions can comprise single components or mixtures of components whose individual chemical structures can be represented by Formula 3:

$$L_r\text{-}G\text{-}(SiX_u Z^b_v Z^c_w)_s \quad \text{(Formula 3)}$$

In Formulae 1, 2 and 3:
  each occurrence of Y is independently a polyvalent species $(Q)_z A(=E)$, wherein the atom (A) attached to the unsaturated heteroatom (E) is attached to the sulfur, which in turn is linked via a group G to the silicon atom including, by way of example, —C(=NR)—; —SC(=NR)—; —SC(=O)—; (—NR)C(=O)—; (—NR)C(=S)—; —OC(=O)—; —OC(=S)—; —C(=O)—; —SC(=S)—; —C(=S)—; —S(=O)—; —S(=O)$_2$—; —OS(=O)$_2$—; (—NR)S(=O)$_2$—; —SS(=O)—; —OS(=O)—; (—NR)S(=O)—; —SS(=O)$_2$—; (—S)$_2$P(=O)—; —(—S)P(=O)—; —P(=O)(—)$_2$; (—S)$_2$P(=S)—; —(—S)P(=S)—; —P(=S)(—)$_2$; (—NR)$_2$P(=O)—; (—NR)(—S)P(=O)—; (—O)(—NR)P(=O)—; (—O)(—S)P(=O)—; (—O)$_2$P(=O)—; —(—O)P(=O)—; —(—NR)P(=O)—; (—NR)$_2$P(=S)—; (—NR)(—S)P(=S)—; (—O)(—NR)P(=S)—; (—O)(—S)P(=S)—; (—O)$_2$P(=S)—; —(—O)P(—S)—; and —(—NR)P(=S)—;
  each occurrence of R is independently selected from hydrogen, straight, cyclic or branched alkyl that may or may not be unsaturated, alkenyl groups, aryl groups, and aralkyl groups, with each R, other than hydrogen, having from 1 to about 18 carbon atoms such as methyl, ethyl, propyl, isopropyl, butyl, pentyl, hexyl, heptyl, octenyl, cyclohexyl, phenyl, benzyl, and the like;
  each occurrence of G is independently selected from a monovalent or polyvalent group derived by substitution of alkyl, alkenyl, aryl or aralkyl wherein G can comprise from 1 to about 30 carbon atoms, with the proviso that if G is univalent (i.e., if p=0), G can be a hydrogen atom;
  each occurrence of X is independently selected from the group consisting of —Cl, —Br, $R^1 O$—, $R^1 O(R^4 CR^5)_f O$—, $R^1 C(=O)O$—, $R^1 R^2 C=NO$—, $R^1 R^2 NO$—, $R^1 R^2 N$—, —$R^1$, and —$(OSiR^1 R^2)_f(OSiR^1 R^2 R^3)$, wherein each occurrence of $R^1$, $R^2$ and $R^3$ is independently R;
  each occurrence of $Z^b$, which forms a bridging structure between two silicon atoms, is independently selected from group consisting of $(—O—)_{0.5}$ and $[—O(R^4 CR^5)_f O—]_{0.5}$, wherein each occurrence of $R^4$ and $R^5$ is independently R;

each occurrence of $Z^c$, which forms a cyclic structure with a silicon atom, is independently given by —O($R^4CR^5$)$_f$O— wherein each occurrence of $R^4$ and $R^5$ is independently R;

each occurrence of Q is independently oxygen, sulfur or (—NR—);

each occurrence of A is independently carbon, sulfur, phosphorus or sulfonyl;

each occurrence of E is independently oxygen, sulfur or (—NR—);

each occurrence of L is independently a halogen atom (i.e., F, Cl, Br, or I), sulfonate group, sulfinate group, or carboxylate group;

each occurrence of the subscripts, u, n, v, w, f, p, r, z, q, a, b, j, p, c, t, s, and k, is independently given by u is 0 to about 3; n is 1 to about 100 and all subranges therebetween, with the proviso that when n is greater than 1, v is greater than 0 and all the valences for $Z^b$ have a silicon atom bonded to them; v is 0 to about 3; w is 0 to about 1; u+v+2w is about 3; f is 1 to about 15; p is 0 to about 5; r is 1 to about 3; z is 0 to about 2; q is 0 to about 6; a is 0 to about 7; b is 1 to about 3; j is 0 to about 1, but it may be 0 only if p is 1, c is 1 to about 6; t is 0 to about 50; s is 1 to about 3; and k is 1 to about 2, with the provisos that (I) if A is carbon, sulfur or sulfonyl, then (i) a+b is 2 and (ii) k is 1; (II) if A is phosphorus, then a+b is 3 unless both (i) c is greater than 1 and (ii) b is 1, in which case a is c+1; and (III) if A is phosphorus, then k is 2; and wherein that the structures described by Formulae 1, 2 and 3 comprise at least one hydrolysable group, $Z^b$ or $Z^c$, that is a difunctional alkoxy group.

As used herein, the terms "diol" and "difunctional alcohol" refer to any structure given by Formula 4, set forth hereinbelow, wherein f, $R^4$ and $R^5$ have the aforestated meanings. These structures represent hydrocarbons in which two hydrogen atoms are replaced with OH in accordance with the structures drawn in Formula 4.

The terms "dialkoxy" and "difunctional alkoxy" as used herein refer to hydrocarbon-based diols in which the two OH hydrogen atoms have been removed to give divalent radicals, and whose structures are given by Formula 5, set forth hereinbelow, wherein f, $R^4$ and $R^5$ have the aforestated meanings.

The term "cyclic dialkoxy" as used herein refers to a silane or group in which cyclization is about silicon, by two oxygen atoms each attached to a common divalent hydrocarbon group, such as is commonly found in diols. Cyclic dialkoxy groups herein are represented by $Z^c$. The structure of $Z^c$ is advantageous in the formation of the cyclic structure. $R^4$ and $R^5$ groups that are more sterically hindered than hydrogen promote the formation of cyclic structures. The formation of cyclic structures is also promoted when the value of f in Formula 5 is 2 or 3.

The term "bridging dialkoxy" as used herein refers to a silane or group in which two different silicon atoms are each bound to one oxygen atom, which in turn is bound to a common divalent hydrocarbon group, such as is commonly found in diols. Bridging dialkoxy groups herein are represented by substituent $Z^b$.

The term "hydrocarbon based diols" as used herein refers to diols that comprise two OH groups on a hydrocarbon structure. Absent from the hydrocarbon based diols are heteroatoms (other than, of course, the two OH groups), in particular ether groups, which are avoided because of problems associated with their tendency to form peroxides spontaneously, which lead to flammability hazards and free radical formation.

Formulae 4 and 5 can be represented as follows:

HO($R^4CR^5$)$_f$OH           (Formula 4)

—O($R^4CR^5$)$_f$O—           (Formula 5)

The structure given by Formula 4 will herein be referred to as the appropriate diol (in a few specific cases, glycol is the more commonly used term), prefixed by the particular hydrocarbon group associated with the two OH groups. Examples include, but are not limited to, neopentylglycol, 1,3-butanediol, and 2-methyl-2,4-pentanediol.

The groups whose structures are given by Formula 5 will herein be referred to as the appropriate dialkoxy, prefixed by the particular hydrocarbon group associated with the two OH groups. Diols, such as, for example, neopentylglycol, 1,3-butanediol and 2-methyl-2,4-pentanediol, correspond herein to the dialkoxy groups, neopentylglycoxy, 1,3-butanedialkoxy, and 2-methyl-2,4-pentanedialkoxy, respectively.

Cyclic and bridging dialkoxy blocked mercaptofunctional silanes herein, in which the diol from which the silane is derived is commonly referred to as a glycol, are named as the corresponding glycoxysilane. Cyclic dialkoxy silanes herein, in which the diol from which the silane is derived is commonly referred to as a diol, are named as the corresponding dialkoxysilane.

As used herein for $Z^b$, the notations, (—O—)$_{0.5}$ and [—O($R^4CR^5$)$_f$O—]$_{0.5}$, refer to one-half of a siloxane bond, and one-half of a bridging dialkoxy group, respectively. These notations are used in conjunction with a silicon atom and they are taken herein to mean one-half of an oxygen atom, namely, the half bound to the particular silicon atom, or to one-half of a dialkoxy group, namely, the half bound to the particular silicon atom, respectively. It is understood that the other half of the oxygen atom or dialkoxy group and its bond to silicon occurs somewhere else in the overall molecular structure being described. Thus, the (—O—)$_{0.5}$ siloxane groups and the [—O($R^4CR^5$)$_f$O—]$_{0.5}$ dialkoxy groups mediate the chemical bonds that hold two separate silicon atoms together, whether these two silicon atoms occur intermolecularly or intramolecularly. In the case of [—O($R^4CR^5$)$_f$O—]$_{0.5}$, if the hydrocarbon group, ($R^4CR^5$)$_f$, is unsymmetrical, either end of [—O($R^4CR^5$)$_f$O—]$_{0.5}$ may be bound to either of the two silicon atoms required to complete the structures given in Formulae 1, 2, and 3.

The term "alkyl" as used herein includes straight, branched and cyclic alkyl groups. The term "alkenyl" as used herein includes any straight, branched, or cyclic alkenyl group comprising one or more carbon-carbon double bonds, where the point of substitution can be either at a carbon-carbon double bond or elsewhere in the group. The term "alkynyl" as used herein includes any straight, branched, or cyclic alkynyl group comprising one or more carbon-carbon triple bonds and, optionally, one or more carbon-carbon double bonds as well, where the point of substitution can be either at a carbon-carbon triple bond, a carbon-carbon double bond, or elsewhere in the group. Examples of alkyls include, but are not limited to, methyl, ethyl, propyl, and isobutyl. Examples of alkenyls include, but are not limited to, vinyl, propenyl, allyl, methallyl, ethylidenyl norbornane, ethylidene norbornyl, ethylidenyl norbornene, and ethylidene norbornenyl. Examples of alkynyls include, but are not limited to, acetylenyl, propargyl, and methylacetylenyl.

The term "aryl" as used herein includes any aromatic hydrocarbon from which one hydrogen atom has been removed useful aralkyl includes, but is not limited to, any of the aforementioned alkyl groups in which one or more hydrogen atoms have been substituted by the same number of like and/or different aryl (as defined herein) substituents; and "arenyl" includes any of the aforementioned aryl groups in which one or more hydrogen atoms have been substituted by the same number of like and/or different alkyl (as defined herein) substituents. Examples of aryls include, but are not limited to, phenyl and naphthalenyl. Examples of aralkyls include, but are not limited to, benzyl and phenethyl. Examples of arenyls include, but are not limited to, tolyl and xylyl.

The terms "cyclic alkyl", "cyclic alkenyl", and "cyclic alkynyl" as used herein also include bicyclic, tricyclic, and higher cyclic structures, as well as the aforementioned cyclic structures further substituted with alkyl, alkenyl, and/or alkynyl groups. Representative examples include, but are not limited to, norbornyl, norbornenyl, ethylnorbornyl, ethylnorbornenyl, ethylcyclohexyl, ethylcyclohexenyl, cyclohexylcyclohexyl, and cyclododecatrienyl.

Representative examples of the functional groups (—YS—) present in the silanes of the present invention include, but are not limited to, thiocarboxylate ester, —C(=O)—S— (any silane with this functional group is a "thiocarboxylate ester silane"); dithiocarboxylate, —C(=S)—S— (any silane with this functional group is a "dithiocarboxylate ester silane"): thiocarbonate ester, —O—C(=O)—S— (any silane with this functional group is a "thiocarbonate ester silane"); dithiocarbonate ester, —S—C(=O)—S— and —O—C(=S)—S— (any silane with this functional group is a "dithiocarbonate ester silane"); trithiocarbonate ester, —S—C(=S)—S— (any silane with this functional group is a "trithiocarbonate ester silane"); dithiocarbamate ester, N—C(=S)—S—(any silane with this functional group is a "dithiocarbamate ester silane"); thiosulfonate ester, —S(=O)$_2$—S— (any silane with this functional group is a "thiosulfonate ester silane"); thiosulfate ester, —O—S(=O)$_2$—S— (any silane with this functional group is a "thiosulfate ester silane"); thiosulfamate ester, (—N—)S(=O)$_2$—S— (any silane with this functional group is a "thiosulfamate ester silane"); thiosulfinate ester, C—S(=O)—S— (any silane with this functional group is a "thiosulfinate ester silane"): thiosulfite ester, —O—S(=O)—S— (any silane with this functional group is a "thiosulfite ester silane"): thiosulfimate ester, N—S(=O)—S-(any silane with this functional group is a "thiosulfimate ester silane"); thiophosphate ester. P(=O)(O—)$_2$(S—) (any silane with this functional group is a "thiophosphate ester silane"); dithiophosphate ester. P(=O)(O—)(S—)$_2$ or P(=S)(O—)$_2$(S—) (any silane with this functional group is a "dithiophosphate ester silane"): trithiophosphate ester, P(=O)(S—)$_3$ or P(=S)(O—)(S—)$_2$ (any silane with this functional group is a "trithiophosphate ester silane"); tetrathiophosphate ester P(=S)(S—)$_3$ (any silane with this functional group is a "tetrathiophosphate ester silane"); thiophosphamate ester, —P(=O)(—N—)(S—) (any silane with this functional group is a "thiophosphamate ester silane"); dithiophosphamate ester, —P(=S)(—N—)(S—) (any silane with this functional group is a "dithiophosphamate ester silane"); thiophosphoramidate ester, (—N—)P(=O)(O—)(S—) (any silane with this functional group is a "thiophosphoramidate ester silane"); dithiophosphoramidate ester, (—N—)P(=O)(S—)$_2$ or (—N—)P(=S)(O—)(S—) (any silane with this functional group is a "dithiophosphoramidate ester silane"); trithiophosphoramidate ester, silane").

In one embodiment, the functional group (—YS—) can be —C(=O)—S—; —SC(=O)S—; —SC(=S)—; —OC(=O)—; —SC(=O)—; —S(=O)—; —OS(=O)—; —(—S)P(=O)—; —P(=O)(—)$_2$ and the like.

In one embodiment of the present invention, n is an integer between 1 and about 10 and all subranges therebetween.

In one embodiment of the present invention, the silane can be wherein Y is —C(=O)— and G has a primary carbon attached to the carbonyl and is a $C_1$ to about $C_{18}$ alkyl. In yet another embodiment, G can be a $C_3$ to about $C_{12}$ alkyl. In yet another embodiment, G can be a $C_6$ to about $C_{10}$ alkyl.

In still another embodiment of the present invention, the silane can be represented by the following structure $[X_u Z^b_v Z^c_w SiGSC(=O)GC(=O)SGSiX_u Z^b_v Z^c_w]_n$ wherein G is a divalent hydrocarbon radical.

Representative examples of G include, but are not limited to, $CH_3(CH_2)_g$— wherein g is 1 to about 29 and all subranges therebetween; diethylene cyclohexane; 1,2,4-triethylene cyclohexane; diethylene benzene; phenylene; —$(CH_2)_g$— wherein g is 1 to about 29, which represent the terminal straight-chain alkyls further substituted terminally at the other end, such as —$CH_2$—, —$CH_2CH_2$—, —$CH_2CH_2CH_2$—, and —$CH_2CH_2CH_2CH_2CH_2CH_2CH_2CH_2$—, and their beta-substituted analogs, such as, for example, —$CH_2(CH_2)_m CH(CH_3)$—, where m is 0 to about 17; —$CH_2CH_2C(CH_3)_2 CH_2$—; the structure derivable from methallyl chloride, —$CH_2CH(CH_3)CH_2$—; any of the structures derivable from divinylbenzene, such as, for example, —$CH_2CH_2(C_6H_4)CH_2CH_2$— and —$CH_2CH_2(C_6H_4)CH(CH_3)$—, where the notation $C_6H_4$ denotes a disubstituted benzene ring; any of the structures derivable from dipropenylbenzene, such as —$CH_2CH(CH_3)(C_6H_4)CH(CH_3)CH_2$—, where the notation $C_6H_4$ denotes a disubstituted benzene ring; any of the structures derivable from butadiene, such as —$CH_2CH_2CH_2CH_2$—, —$CH_2CH_2CH(CH_3)$—, and —$CH_2CH(CH_2CH_3)$—; any of the structures derivable from piperylene, such as —$CH_2CH_2CH_2CH(CH_3)$—, —$CH_2CH_2CH(CH_2CH_3)$—, and —$CH_2CH(CH_2CH_2CH_3)$—; any of the structures derivable from isoprene, such as —$CH_2CH(CH_3)CH_2CH_2$—, —$CH_2CH(CH_3)CH(CH_3)$—, —$CH_2C(CH_3)(CH_2CH_3)$—, $CH_2CH_2CH(CH_3)CH_2$—, —$CH_2CH_2C(CH_3)_2$— and —$CH_2CH[CH(CH_3)_2]$—; any of the isomers of —$CH_2CH_2$-norbornyl-, —$CH_2CH_2$-cyclohexyl-; any of the diradicals obtainable from norbornane, cyclohexane, cyclopentane, tetrahydrodicyclopentadiene, or cyclododecene by loss of two hydrogen atoms; the structures derivable from limonene, —$CH_2CH(4-CH_3-1-C_6H_9—)CH_3$, where the notation $C_6H_9$ denotes isomers of the trisubstituted cyclohexane ring lacking substitution in the 2 position; any of the monovinyl-comprising structures derivable from trivinylcyclohexane, such as —$CH_2CH_2(vinyl C_6H_9)CH_2CH_2$— and —$CH_2CH_2(vinyl C_6H_9)CH(CH_3)$—, where the notation $C_6H_9$ denotes any isomer of the trisubstituted cyclohexane ring; any of the monounsaturated structures derivable from myrcene comprising a trisubstituted C=C, such as —$CH_2CH[CH_2CH_2CH=C(CH_3)_2]CH_2CH_2$—, —$CH_2CH[CH_2CH_2CH=C(CH_3)_2]CH(CH_3)$—, —$CH_2C[CH_2CH_2CH=C(CH_3)_2](CH_2CH_3)$—, —$CH_2CH_2CH[CH_2CH_2CH=C(CH_3)_2]CH_2$—, —$CH_2CH_2(C—)(CH_3)[CH_2CH_2CH=C(CH_3)_2]$, and —$CH_2CH[CH(CH_3)[CH_2CH_2CH=C(CH_3)_2]]$—; and any of the monounsaturated structures derivable from myrcene lacking a trisubstituted C=C, such as —$CH_2CH(CH=CH_2)CH_2CH_2CH_2C(CH_3)_2$—, —$CH_2CH(CH=CH_2)CH_2CH_2CH[CH(CH_3)_2]$—, —$CH_2C(=CH—CH_3)CH_2CH_2CH_2C(CH_3)_2$—, —$CH_2C(=CH—CH_3)CH_2CH_2CH[CH(CH_3)_2]$—, —$CH_2CH_2C(=CH_2)CH_2CH_2CH_2C(CH_3)_2$—, —$CH_2CH_2C(=CH_2)CH_2CH_2CH$

[CH(CH$_3$)$_2$]—, —CH$_2$CH═C(CH$_3$)$_2$CH$_2$CH$_2$CH$_2$C(CH$_3$)$_2$—, and —CH$_2$CH═C(CH$_3$)$_2$CH$_2$CH$_2$CH[CH(CH$_3$)$_2$].

In one embodiment, the structures for G are those in which the sum of the carbon atoms within the G groups within the molecule are from 3 to about 18 and all subranges therebetween. In another embodiment, the structures for G are those in which the sum of the carbon atoms within the G groups within the molecule are from 6 to about 14 and all subranges therebetween. This amount of carbons in the blocked mercaptosilane facilitates the dispersion of the inorganic filler into the organic polymers, thereby improving the balance of properties in the cured filled rubber composition. In another embodiment, G can be —CH$_2$CH$_2$CH$_2$— and CH$_3$CH$_2$CH$_2$CH$_2$CH$_2$CH$_2$CH$_2$—.

Representative examples of R, R$^4$ and R$^5$ groups include R, but are not limited to hydrogen, branched and straight-chain alkyls of 1 to 18 carbon atoms or more, such as methyl, ethyl, propyl, isopropyl, octenyl, cyclohexyl, and butyl; phenyl; benzyl; tolyl; and allyl. In one embodiment, the R groups are C$_1$ to C$_4$ alkyls, and hydrogen. In another embodiment, the R$^4$ and R$^5$ groups are independently hydrogen, methyl, ethyl, and propyl.

Specific examples of X are methoxy, ethoxy, isobutoxy, propoxy, isopropoxy, acetoxy and oximato. X may also be a monovalent alkyl group, such as methyl and ethyl. In one embodiment, X is methoxy, acetoxy or ethoxy.

Specific examples of Z$^b$ and Z$^c$ are the divalent alkoxy groups derived from diols such as, for example, ethylene glycol, propylene glycol, neopentyl glycol, 1,3-propanediol, 2-methyl-1,3-propanediol, 1,3-butanediol, 2-methyl-2,4-pentanediol, 1,4-butanediol, cyclohexane dimethanol, and pinacol. In one embodiment, the divalent alkoxy groups are derived from ethylene glycol, propylene glycol, neopentyl glycol, 1,3-propanediol, 2-methyl-1,3-propanediol, 1,3-butanediol or 2-methyl-2,4-pentanediol. In another embodiment, the divalent alkoxy groups are derived from 1,3-propanediol, 2-methyl-1,3-propanediol, 1,3-butanediol or 2-methyl-2,4-pentanediol.

The cyclic dialkoxy content of the silanes herein must be kept sufficiently high relative to the total dialkoxy content present to prevent excessive crosslinking, which could lead to gellation. In one embodiment, v and w in Formulae 1, 2, and 3 are such that the ratio, v/w, is between 0 and about 1. In another embodiment, the ratio, v/w, is between 0 and about 0.1. In yet another embodiment, the ratio, v/w, is zero.

In one embodiment, v and w in Formulae 1, 2, and 3 are such that the ratio, v/w, is between 0 and about 1; p is 0 to 2; X is RO— or RC(═O)O—; Z$^b$ and Z$^c$ are the divalent alkoxy groups derived from 1,3-propanediol, 2-methyl-1,3-propanediol, 1,3-butanediol, and/or 2-methyl-2,4-pentanediol; R is C$_1$ to C$_4$ alkyl or hydrogen; and G is a straight chain alkyl of 3 to about 18 carbon atoms. In another embodiment, the ratio, v/w, is between 0 and about 0.1; X is ethoxy; Z$^b$ and Z$^c$ are the divalent alkoxy groups derived from 1,3-propanediol, 2-methyl-1,3-propanediol, 1,3-butanediol, and/or 2-methyl-2,4-pentanediol; and G is a C$_3$ to about C$_{12}$ straight-chain alkyl derivative.

In another embodiment of the present invention, when in the silane p is 0, s, r, j and k each is 1, n is 1 to 3, X is —OC$_2$H$_5$, Y is —C(═O)—, G is —(CH$_2$)$_3$— or —(CH$_2$)$_6$CH$_3$, then either w is 0 or at least one occurrence of Z$^b$ is (—O—)$_{0.5}$.

Representative examples of the cyclic and bridging dialkoxy blocked mercaptofunctional silanes of the present invention include, but are not limited to, 2-(2-methyl-2,4-pentanedialkoxyethoxysilyl)-1-ethyl thioacetate; 2-(2-methyl-2,4-pentanedialkoxymethoxysilyl)-1-ethyl thioacetate; 2-(2-methyl-2,4-pentanedialkoxy methylsilyl)-1-ethyl thioacetate; 3-(2-methyl-2,4-pentanedialkoxymethoxysilyl)-1-propyl thioacetate; 2-methyl-2,4-pentanedialkoxyethoxysilylmethyl thioacetate; 2-methyl-2,4-pentanedialkoxyisopropoxysilylmethyl thioacetate; neopentylglycoxypropoxysilylmethyl thioacetate; propyleneglycoxymethylsilylmethyl thioacetate; neopentylglycoxyethylsilylmethyl thioacetate; 2-(neopentylglycoxyisopropoxysilyl)-1-ethyl thioacetate; 2-(neopentylglycoxymethylsilyl)-1-ethyl thioacetate; 2-(1,3-butanedialkoxymethylsilyl)-1-ethyl thioacetate; 3-(1,3-butanedialkoxyethoxysilyl)-1-propyl thioacetate; 3-(1,3-butanedialkoxyisopropoxysilyl)-4-butyl thioacetate: 3-(1,3-butanedialkoxyethylsilyl)-1-propyl thioacetate; 3-(1,3-butanedialkoxymethylsilyl)-1-propyl thioacetate; 6-(2-methyl-2,4-pentanedialkoxyethoxysilyl)-1-hexyl thioacetate; 1-(2-methyl-2,4-pentanedialkoxyethoxysilyl)-5-hexyl thioacetate; 8-(2-methyl-2,4-pentanedialkoxyethoxysilyl)-1-octyl thioacetate; 10-(2-methyl-2,4-pentanedialkoxyethoxysilyl)-1-decyl thioacetate; 3-(2-methyl-2,4-pentanedialkoxyethoxysilyl)-1-propyl thiooctanoate; 3-(2-methyl-2,4-pentanedialkoxyethoxysilyl)-1-propyl thiodecanoate; 3-(2-methyl-2,4-pentanedialkoxyethoxysilyl)-1-propyl thiododecanoate; 3-(2-methyl-2,4-pentanedialkoxyethoxysilyl)-1-propyl thio-2-ethylhexanoate; 3-(2-methyl-2,4-pentanedialkoxyethoxysilyl)-1-propyl thio-2-methylheptanoate; bis-(3-(2-methyl-2,4-pentanedialkoxyethoxysilyl)-1-propyl)dithioadipate; 6-(1,3-butanedialkoxyethoxysilyl)-1-hexyl thioacetate; 1-(1,3-butanedialkoxyethoxysilyl)-5-hexyl thioacetate; 8-(1,3-butanedialkoxyethoxysilyl)-1-octyl thioacetate; 10-(1,3-butanedialkoxyethoxysilyl)-1-decyl thioacetate; 3-(1,3-butanedialkoxyethoxysilyl)-1-propyl thiooctanoate; 3-(1,3-butanedialkoxyethoxysilyl)-1-propyl thiodecanoate; 3-(1,3-butanedialkoxypropoxysilyl)-1-propyl thiododecanoate; 3-(2-methyl-2,4-pentanedialkoxyethoxysilyl)-1-propyl thio-2-ethylhexanoate; 3-(2-methyl-2,4-pentanedialkoxyethoxysilyl)-1-propyl thio-2-methylheptanoate; bis-(3-(2-methyl-2,4-pentanedialkoxyethoxysilyl)-1-propyl) dithioadipate; tris-(3-(2-methyl-2,4-pentanedialkoxyethoxysilyl)-1-propyl)trithiophosphate; bis-(3-(2-methyl-2,4-pentanedialkoxyethoxysilyl-1-propyl)methyldithiophosphonate; bis-(3-(2-methyl-2,4-pentanedialkoxyethoxysilyl-1-propyl) ethyldithiophosphonate; 3-(2-methyl-2,4-pentanedialkoxyethoxysilyl-1-propyldimethylthiophosphinate; 3-(2-methyl-2,4-pentanedialkoxyethoxysilyl-1-propyldiethylthiophosphinate; tris-(3-(2-methyl-2,4-pentanedialkoxyethoxysilyl-1-propyl)tetrathiophosphate; bis-(3-(2-methyl-2,4-pentanedialkoxyethoxysilyl-1-propyl) methyltrithiophosphonate; bis-(3-(2-methyl-2,4-pentanedialkoxyethoxysilyl-1-propyl)ethyltrithiophosphonate; 3-(2-methyl-2,4-pentanedialkoxyethoxysilyl-1-propyldimethyldithiophosphinate; 3-(2-methyl-2,4-pentanedialkoxyethoxysilyl-1-propyldiethyldithiophosphinate; tris-(3-(2-methyl-2,4-pentanedialkoxy-methyl-silyl-1-propyl)trithiophosphate; 3-(2-methyl-2,4-pentanedialkoxyethoxysilyl-1-propylmethylthiosulphate; 3-(2-methyl-2,4-pentanedialkoxyethoxysilyl-1-propylmethanethiosuiphonate; 3-(2-methyl-2,4-pentanedialkoxyethoxysilyl-1-propylethanethiosulphonate; 3-(2-methyl-2,4-pentanedialkoxyethoxysilyl-1-propylbenzenethiosulphonate; and the like.

In another embodiment, cyclic and bridging dialkoxy blocked mercaptofunctional silanes include, but are not limited to, 3-(2-methyl-1,3-propanedialkoxyethoxysilyl)-1-propyl thiooctanoate; 3-methyl-1,3-propanedialkoxyethoxysilyl)-1-propyl thiodecanoate; 3-(2,2-dimethyl-1,3- propanedialkoxyethoxysilyl)-1-propyl thiodecanoate; 3-(2, 2-dimethyl-1,3-propanedialkoxyethoxysilyl)-1-propyl thiooctanoate; 3-(2-methyl-2,4-pentanedialkoxyethoxysilyl)-1-propyl thiooctanoate; 3-[2-methyl-1,3-propanedialkoxy(2-methyl-3-hydroxypropoxy)silyl]-1-propyl thiooctanoate; 3-(2-methyl-2,4-pentanedialkoxyethoxysilyl)-1-propyl thiodecanoate; 3-(2-methyl-2,4-pentanedialkoxyethoxysilyl)-1-propyl thiododecanoate; 3-(2-methyl-2,4-pentanedialkoxyethoxysilyl)-1-propyl thiotetradecanoate; 3-(2-methyl-2,4-pentanedialkoxyethoxysilyl)-1-propyl thio-2-ethylhexanoate; 3-(2-methyl-2,4-pentanedialkoxyethoxysilyl)-1-propyl thio-2-methylheptanoate; bis-(3-(2-methyl-2,4-pentanedialkoxyethoxysilyl)-1-propyl) dithioadipate and the like.

In yet another embodiment, cyclic and bridging dialkoxy blocked mercaptofunctional silanes include, but are not limited to, 3-(2-methyl-2,4-pentanedialkoxyethoxysilyl)-1-propyl thiooctanoate; 3-(2-methyl-2,4-pentanedialkoxyethoxysilyl)-1-propyl thiodecanoate; bis-(3-(2-methyl-2,4-pentanedialkoxyethoxysilyl)-1-propyl) dithioadipate and the like.

In one embodiment, the majority of the cyclic and bridging dialkoxy blocked mercaptofunctional silanes are cyclic and bridging dialkoxy analogs to 3-octanoylthio-1-propyltriethoxysilane with, in some cases, minor variations of the carboxyl group.

Representative examples of the cyclic and bridging dialkoxy haloalkyl silanes of the present invention include, but are not limited, to 2-(2-methyl-2,4-pentanedialkoxyethoxysilyl)-1-propyl chloride; 2-(2-methyl-2,4-pentanedialkoxyisopropoxysilyl)-1-propyl chloride; 2-(2-methyl-2,4-pentanedialkoxymethylsilyl)-1-propyl chloride; 2-(2-methyl-2,4-pentanedialkoxyphenylsilyl)-1-propyl chloride; 3-(1,3-butanedialkoxyethoxysilyl)-1-propyl chloride; 3-(1,3-butanedialkoxyisopropoxysilyl)-1-propyl chloride; 3-(1,3-propanedialkoxyethoxysilyl)-1-propyl chloride; 3-(1,3-propanedialkoxyisopropoxysilyl)-1-propyl chloride: 3-(1,2-propanedialkoxyethoxysilyl)-1-propyl chloride and 3-(1,2-propanedialkoxyisopropoxysilyl)-1-propyl chloride, both derivable from propylene glycol; 3-(1,2-ethanedialkoxyethoxysilyl)-1-propyl chloride and 3-(1,2-ethanedialkoxyisopropoxysilyl)-1-propyl chloride, both derivable from ethylene glycol; 3-(neopentyl glycoxyethoxysilyl)-1-propyl chloride and 3-(neopentyl glycoxyisopropoxysilyl)-1-propyl chloride, both derivable from neopentyl glycol; 3-(2,3-dimethyl-2,3-butanedialkoxyethoxysilyl)-1-propyl chloride and 3-(2,3-dimethyl-2,3-butanedialkoxyisopropoxysilyl)-1-propyl chloride, both derivable from pinacol; 3-(2,2-diethyl-1,3-propanedialkoxyethoxysilyl)-1-propyl chloride; 3-(2,2-diethyl-1,3-propanedialkoxyisopropoxysilyl)-1-propyl chloride; 3-(2-methyl-1,3-propanedialkoxyethoxysilyl)-1-propyl chloride; 3-(2-methyl-1,3-propanedialkoxyisopropoxysilyl)-1-propyl chloride; 3-(1,3-butanedialkoxymethylsilyl)-1-propyl chloride; 3-(1,3-propanedialkoxymethylsilyl)-1-propyl chloride; 3-(1,3-propanedialkoxyphenylsilyl)-1-propyl chloride; 3-(1,2-propanedialkoxymethylsilyl)-1-propyl chloride and 3-(1,2-propanedialkoxyphenylsilyl)-1-propyl chloride, both derivable from propylene glycol; 3-(1,2-ethanedialkoxymethylsilyl)-1-propyl chloride and 3-(1,2-ethanedialkoxyphenylsilyl)-1-propyl chloride, both derivable from ethylene glycol; 3-(neopentyl glycoxymethylsilyl)-1-propyl chloride and 3-(neopentyl glycoxyphenylsilyl)-1-propyl chloride, both derivable from neopentyl glycol; 3-(2,3-dimethyl-2,3-butanedialkoxymethylsilyl)-1-propyl chloride and 3-(2,3-dimethyl-2,3-butanedialkoxyphenylsilyl)-1-propyl chloride, both derivable from pinacol; 3-(2,2-diethyl-1,3-propanedialkoxymethylsilyl)-1-propyl chloride; 3-(2,2-diethyl-1,3-propanedialkoxyphenylsilyl)-1-propyl chloride; 3-(2-methyl-1,3-propanedialkoxyethylsilyl)-1-propyl chloride; 3-(2-methyl-1,3-propanedialkoxyphenylsilyl)-1-propyl chloride; 2-(2-methyl-2,4-pentanedialkoxyethoxysilyl)-1-ethyl chloride; 2-(2-methyl-2,4-pentanedialkoxymethoxysilyl)-1-ethyl bromide; 2-(2-methyl-2,4-pentanedialkoxy methylsilyl)-1-ethyl toluenesulfonate; 2-methyl-2,4-pentanedialkoxyethoxysilylmethyl chloride; 2-methyl-2,4-pentanedialkoxyisopropoxysilylmethyl bromide; neopentylglycoxypropoxysilylmethyl chloride; propyleneglycoxymethylsilylmethyl bromide; neopentylglycoxyethylsilylmethyl sulfinate; 2-(neopentylglycoxyisopropoxysilyl)-1-ethyl chloride; 2-(neopentylglycoxy methylsilyl)-1-ethyl bromide; 2-(1,3-butanedialkoxymethylsilyl)-1-ethyl chloride; 3-(1,3-butanedialkoxyisopropoxysilyl)-4-butyl bromide; 3-(1,3-butanedialkoxyethylsilyl)-1-propyl bromide; 3-(1,3-butanedialkoxymethylsilyl)-1-propyl benzenesulfonate; 6-(2-methyl-2,4-pentanedialkoxyethoxysilyl)-1-hexyl chloride; 1-(2-methyl-2,4-pentanedialkoxyethoxysilyl)-5-hexyl chloride; 8-(2-methyl-2,4-pentanedialkoxyethoxysilyl)-1-octyl chloride; 10-(2-methyl-2,4-pentanedialkoxyethoxysilyl)-1-decyl chloride; 3-(2-methyl-2,4-pentanedialkoxyethoxysilyl)-1-propyl methanesulfonate; 3-(2-methyl-2,4-pentanedialkoxypropoxysilyl)-1-propyl chloride; 3-(2-methyl-2,4-pentanedialkoxyisopropoxysilyl)-1-propyl chloride; 3-(2-methyl-2,4-pentanedialkoxybutoxysilyl)-1-propyl bromide; 3-(2-methyl-2,4-pentanedialkoxyisopropoxysilyl)-1-propyl bromide: bis-(3-(2-methyl-2,4-pentanedialkoxyethoxysilyl)-1-propyl) sulfate; 6-(1,3-butanedialkoxyethoxysilyl)-1-hexyl bromide; 1-(1,3-butanedialkoxyethoxysilyl)-5-hexyl chloride; 8-(1,3-butanedialkoxyethoxysilyl)-1-octyl bromide; 10-(1,3-butanedialkoxyethoxysilyl)-1-decyl chloride; bis-(3-(2-methyl-2,4-pentanedialkoxyethoxysilyl)-1-propyl) sulfate; and the like.

In another embodiment, the cyclic and bridging dialkoxy haloalkyl silanes include, but are not limited to, 3-(2-methyl-2,4-pentanedialkoxyethoxysilyl)-1-propyl chloride; 3-(2-methyl-2,4-pentanedialkoxyisopropoxysilyl)-1-propyl chloride; 3-(2-methyl-2,4-pentanedialkoxymethylsilyl)-1-propyl chloride; 3-(2-methyl-2,4-pentanedialkoxyphenylsilyl)-1-propyl chloride; 3-(1,3-butanedialkoxyethoxysilyl)-1-propyl chloride; 3-(1,3-butanedialkoxyisopropoxysilyl)-1-propyl chloride; 3-(1,3-propanedialkoxyethoxysilyl)-1-propyl chloride; 3-(1,3-propanedialkoxyisopropoxysilyl)-1-propyl chloride; 3-(1,2-propanedialkoxyethoxysilyl)-1-propyl chloride; 3-(1,2-propanedialkoxyisopropoxysilyl)-1-propyl chloride; 3-(1,2-ethanedialkoxyisopropoxysilyl)-1-propyl chloride; 3-(neopentyl glycoxyethoxysilyl)-1-propyl chloride; 3-(neopentyl glycoxyisopropoxysilyl)-1-propyl chloride; 3-(2,3-dimethyl-2,3-butanedialkoxyethoxysilyl)-1-propyl chloride; 3-(2,2-diethyl-1,3-propanedialkoxyisopropoxysilyl)-1-propyl chloride; 3-(2-methyl-1,3-propanedialkoxyethoxysilyl)-1-propyl chloride; 3-(2-methyl-1,3-propanedialkoxyisopropoxysilyl)-1-propyl chloride; 3-(1,3-butanedialkoxymethylsilyl)-1-propyl chloride; 3-(neopentyl glycoxymethylsilyl)-1-propyl chloride; 3-(2-methyl-1,3-propanedialkoxymethylsilyl)-1-propyl chloride; 3-(2-methyl-1,3-propanedialkoxyphenylsilyl)-1-propyl chloride; 2-methyl-2,4-pentanedialkoxyethoxysilylmethyl chloride; and 1,3-butanedialkoxyethoxysilylmethyl chloride and the like.

In one embodiment of the present invention, the cyclic and bridging dialkoxy haloalkyl silanes include, but are not limited to, 2-(2-methyl-2,4-pentanedialkoxyethoxysilyl)-1-propyl chloride; 2-(2-methyl-2,4-pentanedialkoxyisopropoxysilyl)-1-propyl chloride; 3-(1,3-butanedialkoxyethoxysilyl)-1-propyl chloride; 3-(1,3-butanedialkoxyisopropoxysilyl)-1-propyl chloride and the like.

In one embodiment, the cyclic dialkoxy haloalkyl silanes are cyclic and bridging dialkoxy analogs of 3-chloro-1-propyltriethoxysilane (3-triethoxysilyl-1-propyl chloride), which is used as a starting point for the manufacture of silane coupling agents.

In another embodiment of the present invention, each occurrence of X is R. Representative examples of the cyclic and bridging dialkoxy blocked mercaptofunctional silanes of this embodiment include, but are not limited to, 3-(2-methyl-2,4-pentanedialkoxymethylsilyl)-1-propyl thioacetate; 2-methyl-2,4-pentanedialkoxyisopropylsilylmethyl thioacetate; 6-(2-methyl-2,4-pentanedialkoxyethylsilyl)-1-hexyl thioacetate; 1-(2-methyl-2,4-pentanedialkoxymethylsilyl)-5-hexyl thioacetate; 8-(2-methyl-2,4-pentanedialkoxymethylsilyl)-1-octyl thioacetate; 10-(2-methyl-2,4-pentanedialkoxymethylsilyl)-1-decyl thioacetate; 3-(2-methyl-2,4-pentanedialkoxymethylsilyl)-1-propyl thiooctanoate: 3-(2-methyl-2,4-pentanedialkoxymethylsilyl)-1-propyl thiodecanoate; 3-(2-methyl-2,4-pentanedialkoxymethylsilyl)-1-propyl thiododecanoate: 3-(2-methyl-2,4-pentanedialkoxymethylsilyl)-1-propyl thio-2-ethylhexanoate; 3-(2-methyl-2,4-pentanedialkoxymethylsilyl)-1-propyl thio-2-methylheptanoate; bis-(3-(2-methyl-2,4-pentanedialkoxymethylsilyl)-1-propyl) dithioadipate; 3-(1,3-butanedialkoxybutylsilyl)-1-propyl thioacetate; 3-(1,3-butanedialkoxyisopropylsilyl)-4-butyl thioacetate; 6-(1,3-butanedialkoxymethylsilyl)-1-hexyl thioacetate; 8-(1,3-butanedialkoxymethylsilyl)-1-octyl thioacetate; 10-(1,3-butanedialkoxymethylsilyl)-1-decyl thioacetate; 3-(1,3-butanedialkoxymethylsilyl)-1-propyl thiooctanoate; 3-(1,3-butanedialkoxymethylsilyl)-1-propyl thiodecanoate; 3-(1,3-butanedialkoxypropylsilyl)-1-propyl thiododecanoate; 3-(2,2-dimethyl-1,3-propanedialkoxymethylsilyl)-1-propyl thiodecanoate; 3-(2,2-dimethyl-1,3-propanedialkoxymethylsilyl)-1-propyl thiooctanoate; 3-(2-methyl-1,3-propanedialkoxymethylsilyl)-1-propyl thiooctanoate; 3-(2-methyl-1,3-propane dialkoxymethylsilyl)-1-propyl thiodecanoate; 3-(2-methyl-1,3-propane dialkoxymethylsilyl)-1-propyl thiododecanoate; 3-(2-methyl-1,3-propane dialkoxymethylsilyl)-1-propyl thiotetradecanoate; 3-(2-methyl-1,3-propane dialkoxymethylsilyl)-1-propyl thio-2-ethylhexanoate; 3-(2-methyl-1,3-propane dialkoxymethylsilyl)-1-propyl thio-2-methylheptanoate; bis-(3-(2-methyl-1,3-propane dialkoxymethylsilyl)-1-propyl) dithioadipate; neopentylglycoxypropylsilylmethyl thioacetate and the like.

In another embodiment, cyclic and bridging dialkoxy blocked mercaptofunctional silanes include, but are not limited to bis-(3-(2-methyl-2,4-pentanedialkoxymethylsilyl-1-propyl)methyldithiophosphonate; bis-(3-(2-methyl-2,4-pentanedialkoxymethylsilyl-1-propyl)ethyldithiophosphonate: 3-(2-methyl-2,4-pentanedialkoxymethylsilyl-1-propyldimethylthiophosphinate; 3-(2-methyl-2,4-pentanedialkoxymethylsilyl-1-propyldiethylthiophosphinate; tris-(3-(2-methyl-2,4-pentanedialkoxymethylsilyl-1-propyl) tetrathiophosphate; bis-(3-(2-methyl-2,4-pentanedialkoxymethylsilyl-1-propyl) methyltrithiophosphonate; bis-(3-(2-methyl-2,4-pentanedialkoxymethylsilyl-1-propyl) ethyltrithiophosphonate; 3-(2-methyl-2,4-pentanedialkoxyethylsilyl-1-propyldimethyldithiophosphinate; 3-(2-methyl-2,4-pentanedialkoxymethylsilyl-1-propyldiethyldithiophosphinate; 3-(2-methyl-2,4-pentanedialkoxymethylsilyl-1-propylmethylthiosulphate; 3-(2-methyl-2,4-pentanedialkoxymethylsilyl-1-propyl-methanethiosulphonate; 3-(2-methyl-2,4-pentanedialkoxypropylsilyl-1-propylethanethiosulphonate; 3-(2-methyl-2,4-pentanedialkoxymethylsilyl-1-propylbenzenethiosulphonate; and the like.

The cyclic and bridging dialkoxy blocked mercaptofunctional silane compositions included herein may comprise single components or various mixtures of individual cyclic and bridging dialkoxy blocked mercaptofunctional silane components, blocked mercaptofunctional silane components that comprise only monofunctional alkoxy groups, and which optionally include other species as well, including, for example, those wherein synthetic methods result in a distribution of various silanes and those wherein mixtures of the starting components are employed for generating mixtures of cyclic and bridging dialkoxy blocked mercaptofunctional silane products. Moreover, it is to be understood that the partial hydrolyzates and/or condensates of these cyclic and bridging dialkoxy blocked mercaptofunctional silanes (i.e., cyclic and bridging dialkoxy blocked mercaptofunctional siloxanes and/or silanols) may also be encompassed by the silanes herein, in that these partial hydrolyzates and/or condensates will be a side product of most methods of manufacture of the cyclic and bridging dialkoxy blocked mercaptofunctional silanes or can occur upon storage of the cyclic and bridging dialkoxy blocked mercaptofunctional silanes, especially in humid conditions, or under conditions in which residual water remaining from their preparation is not completely removed subsequent to their preparation.

Likewise, the cyclic and bridging dialkoxy haloalkyl silane compositions included herein may comprise single components or various mixtures of individual cyclic and bridging dialkoxy haloalkyl silane components, haloalkyl silane components which comprise only monofunctional alkoxy groups, and optionally including other species as well, including, for example, those wherein synthetic methods result in a distribution of various silanes and including those wherein mixtures of the starting components are employed for generating mixtures of cyclic and bridging dialkoxy haloalkyl and/or cyclic and bridging dialkoxy blocked mercaptofunctional silane products.

Moreover, it is to be understood that the partial hydrolyzates and/or condensates of these cyclic and bridging dialkoxy haloalkyl silanes (i.e., cyclic and bridging dialkoxy haloalkyl siloxanes and/or silanols) may also be encompassed by the cyclic and bridging dialkoxy haloalkyl silanes herein, in that these partial hydrolyzates and/or condensates will be a side product of most methods of manufacture of the cyclic and bridging dialkoxy haloalkyl silanes or can occur upon storage of the cyclic and bridging dialkoxy haloalkyl silanes, especially in humid conditions, or under conditions in which residual water remaining from their preparation is not completely removed subsequent to their preparation.

Furthermore, partial to substantial hydrolysis and siloxane content of the cyclic and bridging dialkoxy blocked mercaptofunctional silanes are encompassed by the silanes described herein and may be deliberately prepared by incorporating the appropriate stoichiometry or an excess of water into the methods of preparation described herein for the silanes. Silane structures herein encompassing hydrolyzates and siloxanes are described in the structures given in Formulae 1 and 2 wherein the subscripts, v, of $Z^b$=(—O—)$_{0.5}$ and/or u of X=OH are substantive (i.e., substantially larger than zero).

The cyclic and bridging dialkoxy blocked mercaptofunctional silane compositions may be loaded on a carrier, or filler, such as, for example, a porous polymer, carbon black, silica or the like, so that they are in a dry free flowing form for convenient delivery to rubber. In one embodiment, the carrier would be part of the inorganic filler to be used in the rubber.

In one embodiment, a dry free flowing composition comprises a silane in accordance with this invention in admixture with one or more of the aforesaid carrier materials. e.g., in a weight ratio of from about 0.1 to about 60 weight percent. The BET surface area of such carriers as silica can vary widely and in one embodiment can vary from about 100 $m^2/g$ to about 300 $m^2/g$. Another property of such carriers is their DOP adsorption, an oil adsorption index. In the case of nonporous carriers such as silica, the DOP adsorption can range from about 100 ml/100 gm to about 400 ml/100 gm. Porous carriers such as foamed polyolefins can advantageously absorb from about 10 ml to about 250 ml/100 gm (from about 9 to about 70 weight percent) of the silane of the present invention.

The filler can be essentially inert to the silane with which it is admixed as is the case with carbon black or organic polymers, or it can be reactive therewith, e.g., the case with carriers possessing metal hydroxyl surface functionality, e.g., silicas and other silaceous particulates which possess surface silanol functionality.

Manufacture of Cyclic and Bridging Dialkoxy
Blocked Mercaptofunctional Silanes Anhydrous
Methods The methods for the preparation of the cyclic and bridging dialkoxy blocked mercaptofunctional silanes herein can involve esterification of sulfur in a sulfur-comprising silane and direct incorporation of the blocked mercapto group into a silane, either by substitution of an appropriate leaving group or by addition across a carbon-carbon double bond or can involve transesterification or ester exchange of the alkoxysilyl moieties of a blocked mercapto silane.

Illustrative examples of synthetic procedures for the preparation of thioester silanes would include: Reaction 1) the reaction between a mercaptosilane and an acid anhydride corresponding to the thioester group present in the desired product; Reaction 2) the reaction of an alkali metal salt of a mercaptosilane with the appropriate acid anhydride or acid halide; Reaction 3) the transesterification between a mercaptosilane and an ester, optionally using any appropriate catalyst such as, for example, an acid, base, tin compound, titanium compound, transition metal salt, a salt of the acid corresponding to the ester and the like; Reaction 4) the transesterification between a thioester silane and another ester, optionally using any appropriate catalyst such as, for example, an acid, base, tin compound, titanium compound, transition metal salt, a salt of the acid corresponding to the ester and the like; Reaction 5) the transesterification between a 1-sila-2-thiacyclopentane or a 1-sila-2-thiacyclohexane and an ester, optionally using any appropriate catalyst such as, for example, an acid, base, tin compound, titanium compound, transition metal salt, a salt of the acid corresponding to the ester and the like; Reaction 6) the free radical addition of a thioacid across a carbon-carbon double bond of an alkene-functional silane, catalyzed by UV light, heat, or the appropriate free radical initiator wherein, if the thioacid is a thiocarboxylic acid, the two reagents are brought into contact with each other in such a way as to ensure that whichever reagent is added to the other is reacted substantially before the addition proceeds; and Reaction 7) the reaction between an alkali metal salt of a thioacid with a haloalkylsilane under anhydrous conditions.

Acid halides for use herein include, but are not limited to, organic acid halides, inorganic acid halides, e.g., $POT_3$, $SOT_2$, $SO_2T_2$, $COT_2$, $CST_2$, $PST_3$ and $PT_5$ wherein T is a halide, and the like and mixtures thereof. Acid anhydrides, include, but are not limited to, organic acid anhydrides (and their sulfur analogs), inorganic acid anhydrides, e.g., $SO_3$, $SO_2$, $P_2O_5$, $P_2S_5$, $H_2S_2O_7$, $CO_2$, COS, and $CS_2$, and the like and mixtures thereof.

Illustrative examples of synthetic procedures for the preparation of cyclic and bridging dialkoxy blocked mercaptofunctional silanes include: Reaction 8) the reaction between a mercaptosilane and a carboxylic acid anhydride corresponding to the thiocarboxylate group present in the desired product; Reaction 9) reaction of an alkali metal salt of a mercaptosilane with the appropriate carboxylic acid anhydride or acid halide; Reaction 10) the transesterification between a mercaptosilane and a carboxylate ester, optionally using any appropriate catalyst such as, for example, an acid, base, tin compound, titanium compound, transition metal salt, a salt of the acid corresponding to the carboxylate ester and the like; Reaction 11) the transesterification between a thiocarboxylate-functional silane and another ester, optionally using any appropriate catalyst such as, for example, an acid, base, tin compound, titanium compound, transition metal salt, a salt of the acid corresponding to the other ester and the like; Reaction 12) the transesterification between a 1-sila-2-thiacyclopentane or a 1-sila-2-thiacyclohexane and a carboxylate ester, optionally using any appropriate catalyst such as, for example, an acid, base, tin compound, titanium compound, transition metal salt, a salt of the acid corresponding to the carboxylate ester and the like; Reaction 13) the free radical addition of a thiocarboxylic acid across a carbon-carbon double bond of an alkene-functional silane, catalyzed by UV light, heat, or the appropriate free radical initiator; Reaction 14) the reaction between an alkali metal salt of a thiocarboxylic acid with a haloalkylsilane under anhydrous conditions; Reaction 15) the transesterification between the alkoxysilyl moieties of a thiocarboxylate silane and a diol, catalyzed by an acid or a base, titanium alkoxide or chelate, or zirconium alkoxide or chelate; and Reaction 16) the continuous transesterification between the alkoxysilyl moieties of a thiocarboxylate silane and a diol, catalyzed by an acid or a base, titanium alkoxide or chelate, or zirconium alkoxide or chelate, conducted simultaneously with distillation, e.g., thin film distillation.

Reactions 1 and 8 could be carried out by distilling a mixture of the mercaptosilane and the acid anhydride and optionally a solvent. Appropriate boiling temperatures of the mixture can range from about 50 to about 250° C. and all subranges therebetween. In one embodiment, the boiling temperature can range from about 60 to about 200° C. and all subranges therebetween. In another embodiment, the boiling temperature can range from about 70 to about 170° C. and all subranges therebetween. This process leads to a chemical reaction in which the mercapto group of the mercaptosilane is esterified to the thioester silane analog with release of an equivalent of the corresponding acid. The acid typically is more volatile than the acid anhydride. The reaction is driven by the removal of the more volatile acid by distillation. For the more volatile acid anhydrides, e.g., acetic anhydride, the distillation can be carried out at ambient pressure to reach temperatures sufficient to drive the reaction toward completion. For less volatile materials solvents, e.g., toluene, xylene, glyme and diglyme, could be used with the process to limit temperature. Alternatively, the process could be run at reduced pressure. It can be advantageous to use up to a two-fold excess or more of the acid anhydride which would be distilled out of the mixture after all of the more volatile reaction coproducts, consisting of acids and non-silane esters, have been distilled out. This excess of acid anhydride would serve to drive the reaction to completion, as well as to help drive the coproducts out of the reaction mixture. At the completion of the reaction, distillation should be continued to drive out the remaining acid anhydride. The product optionally could be distilled.

Reactions 2 and 9 can be carried out in two steps. The first step involves at least the conversion of the mercaptosilane to a corresponding metal derivative, e.g., alkali metal derivatives such sodium, potassium or lithium. The metal derivative can generally be prepared by adding the alkali metal or a strong base derived from the alkali metal to the mercaptosilane. The reaction can occur at ambient temperature. Useful bases include, but are not limited to, alkali metal alkoxides, amides, hydrides, mercaptides. Alternatively, alkali metal organometallic reagents or grignard reagents which would yield magnesium derivatives) may also be used. Solvents such as, for example, toluene, xylene, benzene, aliphatic hydrocarbons, ethers, alcohols and the like could be used to prepare the alkali metal derivatives. Once the alkali metal derivative is prepared, any alcohol present would need to be removed. This could be done by distillation or evaporation. Alcohols such as methanol, ethanol, propanol, isopropanol, butanol, isobutanol, and t-butanol may be removed by azeotropic distillation with benzene, toluene, xylene, or aliphatic hydrocarbons. In one embodiment, toluene and xylene are used. In another embodiment, toluene is used. The second step in the overall process would be to add to this solution, with stirring, the acid chloride or acid anhydride at temperatures between −20° C. and the boiling point of the mixture; and at temperatures between 0° C. and ambient temperature in another embodiment. The product would be isolated by removing the salt and solvent. It could be purified by distillation.

Reactions 3 and 10 could be carried out by distilling a mixture of the mercaptosilane and the ester and optionally a solvent and/or a catalyst. Appropriate boiling temperatures of the mixture would be above about 100° C. This process leads to a chemical reaction in which the mercapto group of the mercaptosilane is esterified to the thioester silane analog with release of an equivalent of the corresponding alcohol. The reaction is driven by the removal of the alcohol by distillation, either as the more volatile species, or as an azeotrope with the ester. For the more volatile esters the distillation is suitably carried out at ambient pressure to reach temperatures sufficient to drive the reaction toward completion. For less volatile esters, solvents, such as toluene, xylene, glyme, and diglyme could be used with the process to limit temperature. Alternatively, the process could be run at reduced pressure. It can be advantageous to use up to a two-fold excess or more of the ester, which would be distilled out of the mixture after all of the alcohol coproduct has been distilled out. This excess ester would serve to drive the reaction to completion as well as to help drive the coproduct alcohol out of the reaction mixture. At the completion of the reaction, distillation would be continued to drive out the remaining ester. The product optionally could be distilled.

Reactions 4 and 11 could be carried out by distilling a mixture of the thioester silane and the other ester and optionally a solvent and/or a catalyst. Appropriate boiling temperatures of the mixture would be above about 80° C.; and usually above about 100° C. In one embodiment, the temperature may not exceed about 250° C. This process leads to a chemical reaction in which the thioester group of the thioester silane is transesterified to a new thioester silane with release of an equivalent of a new ester. The new thioester silane generally would be the least volatile species present; however, the new ester would be more volatile than the other reactants. The reaction would be driven by the removal of the new ester by distillation. The distillation can be carried out at ambient pressure to reach temperatures sufficient to drive the reaction toward completion. For systems using only less volatile materials, solvents, such as toluene, xylene, glyme, and diglyme could be used with the process to limit temperature. Alternatively, the process could be run at reduced pressure. It could be advantageous to use up to a two-fold excess or more of the other ester, which would be distilled out of the mixture after all of the new ester coproduct has been distilled out. This excess other ester would serve to drive the reaction to completion as well as to help drive the co-product other ester out of the reaction mixture. At the completion of the reaction, distillation would be continued to drive out the remaining said new ester. The product optionally then could be distilled.

Reactions 5 and 12 could be carried out by heating a mixture of the 1-sila-2-thiacyclopentane or the 1-sila-2-thiacyclohexane and the ester with the catalyst. Optionally, the mixture could be heated or refluxed with a solvent. In another embodiment, a solvent whose boiling point matches the desired temperature is used. Optionally, a solvent of higher boiling point than the desired reaction temperature can be used at reduced pressure, the pressure being adjusted to bring the boiling point down to the desired reaction temperature. The temperature of the mixture can be in the range of about 80 to about 250° C. and all subranges therebetween. In another embodiment, the temperature can range from about 100 to about 200° C. and all subranges therebetween. Solvents, such as toluene, xylene, aliphatic hydrocarbons, and diglyme could be used with the process to adjust the temperature. Alternatively, the process could be run under reflux at reduced pressure. In one embodiment, the condition is to heat a mixture of the 1-sila-2-thiacyclopentane or the 1-sila-2-thiacyclohexane and the ester, without solvent, optionally under inert atmosphere, for a period of about 20 to about 100 hours and all subranges therebetween and at a temperature of about 120 to about 170° C. and all subranges therebetween using the sodium, potassium, or lithium salt of the acid corresponding to the ester as a catalyst. The process leads to a chemical reaction in which the sulfur-silicon bond of the 1-sila-2-thiacyclopentane or the 1-sila-2-thiacyclohexane is transesterified by addition of the ester across said sulfur-silicon bond. The product is the thioester silane analog of the original 1-sila-2-thiacyclopentane or the 1-sila-2-thiacyclohexane. Optionally, up to a two-fold excess or more of the ester could be used to drive the reaction toward completion. At the completion of the reaction, the excess ester can be removed by, e.g., distillation. The product optionally could be purified by distillation.

Reactions 6 and 13 can be carried out by heating or refluxing a mixture of the alkene-functional silane and the thioacid. Aspects of Reaction 13 have been disclosed previously in U.S. Pat. No. 3,692,812 and by G. A. Gornowicz et al. in *J. Org. Chem.* (1968), 33(7), 2918-24. The uncatalyzed reaction may occur at temperatures as low as about 105° C. In another embodiment, the temperature may exceed about 160° C. The reaction may be made reliable and the reaction brought largely to completion by using UV radiation or a catalyst. With a catalyst, the reaction can be made to occur at temperatures below about 90° C. Useful catalysts are free radical initiators, e.g., peroxides, such as organic peroxides, and azo compounds. Examples of peroxide initiators include peracids, such bybenzoic and peracetic acids; esters of peracids; hydroperoxides, such as t-butyl hydroperoxide; peroxides, such as di-t-butyl peroxide; and peroxy-acetals and ketals, such as 1,1-bis(t-butylperoxy)cyclohexane, or any other peroxide. Examples of azo initiators include azobisisobutyronitrile (AIBN); 1,1'-azobis(cyclohexanecarbonitrile) (VAZO; DuPont product); and azo-tert-butane.

The reaction can be run by heating a mixture of the alkene-functional silane and the thioacid with the catalyst. In one embodiment, the overall reaction can be run on an equimolar or near equimolar basis to the highest conversions. The reaction is sufficiently exothermic that it tends to lead to a rapid temperature increase to reflux followed by a vigorous reflux as the reaction initiates and continues rapidly. This vigorous reaction can lead to hazardous boilovers for larger quantities. Side reactions, contamination, and loss in yield can result as well from uncontrolled reactions.

The reaction can be controlled effectively by adding partial quantities of one reagent to the reaction mixture, initiating the reaction with the catalyst, allowing the reaction to run its course largely to completion, and then adding the remainder of the reagent, either as a single addition or as multiple additives. The initial concentrations and rate of addition and number of subsequent additions of the deficient reagent depend on the type and amount of catalyst used, the scale of the reaction, the nature of the starting materials, and the ability of the apparatus to absorb and dissipate heat. A second way of controlling the reaction would involve the continuous addition of one reagent to the other with concomitant continuous addition of catalyst. Whether continuous or sequential addition is used, the catalyst can be added alone and/or pre-blended with one or both reagents, or combinations thereof. In one embodiment, two methods may be used for reactions involving thioacetic acid and alkene-functional silanes having terminal carbon-carbon double bonds. The first method involves initially bringing the alkene-functional silane to a temperature of about 160 to about 180° C. and all subranges therebetween, or to reflux, whichever temperature is lower. The first portion of thioacetic acid can be added at a rate as to maintain up to a vigorous, but controlled reflux. For alkene-functional silanes with boiling points above about 100 to about 120° C. this reflux results largely from the relatively low boiling point of thioacetic acid (about 88 to about 92° C. depending on purity) relative to the temperature of the alkene-functional silane.

At the completion of the addition, the reflux rate rapidly subsides. It often accelerates again within several minutes, especially if an alkene-functional silane with a boiling point above about 120° C. is used, as the reaction initiates. If it does not initiate within about 10 to about 15 minutes, initiation can be brought about by addition of catalyst. In one embodiment, the catalyst is di-t-butyl peroxide. The appropriate quantity of catalyst is from about 0.2 to about 2 percent and all subranges therebetween of the total mass of mixture to which the catalyst is added. In another embodiment, the quantity of catalyst can range from about 0.5 to about 1 percent and all subranges therebetween of the total mass of mixture to which the catalyst is added. The reaction typically initiates within a few minutes as evidenced by an increase in reflux rate. The reflux temperature gradually increases as the reaction proceeds. Then the next portion of thioacetic acid is added, and the aforementioned sequence of steps are repeated. The number of thioacetic additions for total reaction quantities of about one to about four kilograms can be two, with about one-third of the total thioacetic acid used in the first addition and the remainder in the second. For total quantities in the range of about four to ten kilograms, a total of three thioacetic additions can be used, the distribution being about 20 percent of the total used in the first addition, about 30 percent in the second addition, and the remainder in the third addition. For larger scales involving thioacetic acid and alkene-functional silanes, it is advantageous to use more than a total of three thioacetic additions and more advantageous, to add the reagents in the reverse order. Initially, the total quantity of thioacetic acid is brought to reflux. This is followed by continuous addition of the alkene-functional silane to the thiolacetic acid at such a rate as to bring about a smooth, but vigorous, reaction rate.

The catalyst, e.g., di-t-butylperoxide, can be added in small portions during the course of the reaction or as a continuous flow. It is best to accelerate the rate of catalyst addition as the reaction proceeds to completion to obtain the highest yields of product for the lowest amount of catalyst required. The total quantity of catalyst used should be about 0.5 to about 2 percent of the total mass of reagents used. Whichever method is used, the reaction is followed up by a vacuum stripping process to remove volatiles and unreacted thioacetic acid and silane. The product may be purified by distillation.

Methods to run Reactions 7 and 14 can generally be carried out in two steps. The first step involves preparation of a salt of the thioacid. In one embodiment, alkali metal derivatives are used, e.g., sodium derivatives. These salts can be prepared as solutions in solvents in which the salt is appreciably soluble, but suspensions of the salts as solids in solvents in which the salts are only slightly soluble can also be used. Alcohols, such as methanol, ethanol, propanol, isopropanol, butanol, isobutanol, t-butanol and the like are useful because the alkali metal salts are slightly soluble in them. In cases where the desired product is an alkoxysilane, it is advantageous to use an alcohol corresponding to the silane alkoxy group to prevent transesterification at the silicon ester. Alternatively, nonprotic solvents can be used. Examples of appropriate solvents are ethers or polyethers such as, for example, glyme, diglyme, and dioxanes: N,N'-dimethylformamide; N,N'-dimethylacetamide; dimethylsulfoxide; N-methylpyrrolidinone; hexamethylphosphoramide and the like. Once a solution, suspension, or combination thereof of the salt of the thioacid has been prepared, the second step is to react it with the appropriate haloalkylsilane. This may be accomplished by stirring a mixture of the haloalkylsilane with the solution, suspension, or combination thereof of the salt of the thioacid at temperatures corresponding to the liquid range of the solvent for a period of time sufficient to complete substantially the reaction. In one embodiment, temperatures are those at which the salt is appreciably soluble in the solvent and at which the reaction proceeds at an acceptable rate without excessive side reactions. With reactions starting from chloroalkylsilanes in which the chlorine atom is not allylic or benzylic, temperatures and range from about 60 to about 160° C. and all subranges therebetween. Reaction times can range from one or several hours to several days. For alcohol solvents where the alcohol possesses four carbon atoms or fewer, the temperature can be at or near reflux. When using diglyme as a solvent, the temperature can range from about 70 to about 120° C. and all subranges therebetween, depending on the thioacid salt used. If the haloalkylsilane is a bromoalkylsilane or a chloroalkylsilane in which the chlorine atom is allylic or benzylic, temperature reductions of about 30 to about 60° C. and all subranges therebetween are appropriate relative to those appropriate for nonbenzylic or nonallylic chloroalkylsilanes because of the greater reactivity of the bromo group. In one embodiment, bromoalkylsilanes are used because of their greater reactivity, lower temperatures required, and greater ease in filtration or centrifugation of the coproduct alkali metal halide. This, however, can be overridden by the lower cost of the chloroalkylsilanes, especially for those having the halogen in the allylic or benzylic position. For reactions between straight chain chloroalkylethoxysilanes and sodium thiocarboxylates to form thiocarboxylate ester ethoxysilanes, ethanol can be used at reflux for about 10 to about 20 hours and all subranges therebetween if 5 to 20% mercaptosilane is acceptable in the product. Otherwise, diglyme can be used in which the reaction can be carried out at a temperature in the range of about 80 to about 120° C. and all subranges therebetween for about one to about three hours and all subranges therebetween. Upon completion of the reaction, the salts and solvent should be removed and the product may be distilled to achieve higher purity.

If the salt of the thioacid to be used in Reactions 7 and 14 is not commercially available, its preparation may be accomplished by one of two methods, described below as Method A and Method B. Method A involves adding the alkali metal or a base derived from the alkali metal to the thioacid. The reaction occurs at ambient temperature. Useful bases include, but are not limited to, alkali metal alkoxides, hydrides, carbonate, bicarbonate and the like and mixtures thereof. Solvents, such as toluene, xylene, benzene, aliphatic hydrocarbons, ethers, and alcohols may be used to prepare the alkali metal derivatives. In Method B, acid chlorides or acid anhydrides would be converted directly to the salt of the thioacid by reaction with the alkali metal sulfide or hydrosulfide. Hydrated or partially hydrous alkali metal sulfides or hydrosulfides are available, however, anhydrous or nearly anhydrous alkali metal sulfides or hydrosulfides can also be used. Hydrous materials can be used, however, but with loss in yield and hydrogen sulfide formation as a co-product. The reaction involves addition of the acid chloride or acid anhydride to the solution or suspension of the alkali metal sulfide and/or hydrosulfide and heating at temperatures ranging from ambient to the reflux temperature of the solvent for a period of time sufficient to largely complete the reaction, as evidenced by the formation of the co-product salts.

If the alkali metal salt of the thioacid is prepared in such a way that an alcohol is present, either because it was used as a solvent, or because it was formed, for example, by the reaction of a thioacid with an alkali metal alkoxide, it may be desirable to remove the alcohol if a product low in mercaptosilane is desired and if loss of diol from silicon is to be prevented. In this case, it would be necessary to remove the alcohol prior to reaction of the salt of the thioacid with the haloalkylsilane. This could be done by distillation or evaporation. Alcohols such as methanol, ethanol, propanol, isopropanol, butanol, isobutanol, and t-butanol can be removed by, for example, azeotropic distillation with benzene, toluene, xylene, or aliphatic hydrocarbons. In one embodiment, toluene and xylene are used.

Reaction 15 can be carried out by at least reacting a catalyzed mixture of a thiocarboxylate-alkoxy silane and a diol with simultaneous distillation. The reaction leads to the alcohol exchange of one or more of the alkoxy groups selectively at the silicon atom of the thiocarboxylate silane with the diol. The reaction is driven by the removal of the more volatile alcohol by distillation. In one embodiment, the catalysts are acids. Suitable acid catalysts include, but are not limited to, p-toluenesulfonic acid, sulfuric acid, hydrochloric acid, chlorosilanes, chloroacetic acids, phosphoric acid, and the like and mixtures thereof. In another embodiment, base catalysts are used. However, base catalysts are less desirable as they have been found to be less efficient. For example, sodium ethoxide is active, but causes some degradation of the thiocarboxylate silane. In another embodiment, titanium alkoxides or chelates and zirconium alkoxides or chelates are used as catalysts.

Examples of diols that are capable of transesterification of the alkoxysilyl groups include, but are not limited 1,2-ethylene glycol, neopentyl glycol, 1,2-propanediol, 1,3-propanediol, 2-methyl-1,3-propanediol, 1,3-butanediol, 2-methyl-2,4-pentanediol, 1,4-butanediol, 1,6-hexanediol, cyclohexane dimethanol, pinacol and the like and mixtures thereof.

Reaction 16 could be carried out by continuously premixing the flow-streams of thiocarboxylate-alkoxy silane, diol and catalyst at appropriate ratios and then introducing the premixed reactants into a reactive distillation system, e.g., a thin film distillation device operating at the desired reaction temperature and partial vacuum conditions. Conducting the reaction in a thin film at low pressure can accelerate the removal of the alcohol byproduct and improve the transesterification reaction rate. The vaporization and removal of the alcohol byproduct from the film shifts the chemical equilibrium of the reaction to favor formation of the desired product and minimizes undesired side reactions.

Preparation of Cyclic and Bridging Dialkoxy Blocked Mercaptofunctional Silanes Aqueous Method for Thiocarboxylate Silanes The preparation of the cyclic and bridging dialkoxy blocked mercaptofunctional silanes generally involves at least the reaction between an aqueous solution of a salt of a thiocarboxylic acid or other (thus, an aqueous solution of a thiocarboxylate salt, which would possess the thiocarboxylate anion) with a cyclic and bridging dialkoxy haloalkyl silane, in the presence or absence of a phase transfer catalyst. Optionally, mixtures comprising aqueous thiocarboxylate salts and/or cyclic and bridging dialkoxy haloalkyl silanes may be used, from which mixtures comprising cyclic and bridging dialkoxy blocked mercaptofunctional silanes may be prepared. The cyclic and bridging dialkoxy haloalkyl silanes may themselves be used as mixtures with haloalkyl silanes, thereby yielding products comprising mixtures comprising cyclic and bridging dialkoxy blocked mercaptofunctional silanes with thiocarboxylate or thioester silanes comprising only monofunctional alkoxy groups. As used herein, the term "cyclic and bridging dialkoxy haloalkyl silane" refers to any silane whose structure can be represented by Formula 3, first given above. The term "haloalkyl silane" as used herein refers to any silane whose structure can be represented by Formula 6 below. Collectively, the cyclic and bridging dialkoxy haloalkyl silanes and haloalkyl silanes will herein be referred to as "alkoxy haloalkyl silanes". Thus, the terms "cyclic and bridging dialkoxy haloalkyl silane", "haloalkyl silane", and "alkoxy haloalkyl silane", as used herein, would include single components or mixtures comprising silanes with one or more halogen substitutions for hydrogen on their hydrocarbon groups, as well as other substitutions that would represent potential leaving groups during nucleophilic substitution reactions, as described below.

Structures for the cyclic and bridging dialkoxy haloalkyl silanes and haloalkyl silanes are given in Formulae 3 and 6, respectively,

$$L_r\text{-}G\text{-}(SiX_u Z^b_v Z^c_w)_s \quad\quad (\text{Formula 3}),$$

$$L_r\text{-}G\text{-}(SiX_3)_s \quad\quad (\text{Formula 6})$$

and structures for the thiocarboxylate salts are given in Formulae 7, 8 and 9, respectively,

$$G(-Y^1-SM)_d \quad\quad (\text{Formula 7})$$

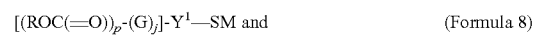
$$[(ROC(=O))_p\text{-}(G)_j]\text{-}Y^1\text{---}SM \text{ and} \quad\quad (\text{Formula 8})$$

$$[(Z^c_w Z^b_v X_u Si)_q\text{-}G]\text{-}Y^1\text{---}SM \quad\quad (\text{Formula 9})$$

wherein each occurrence of M is independently an alkali metal; ammonium; or a mono-, di-, or tri-substituted ammonium;

each occurrence of $Y^1$ is independently carbonyl, d is 1 to about 6 and R, L, G, X, $Z^b$, $Z^c$, j, p, q, u, v, w, r and s have the aforestated meanings.

M can be an alkali metal; ammonium; or a mono-, di-, or tri-substituted ammonium. Thus, M can be a monocation, meaning it occurs as a cation, typically with a single positive charge. Dicationic ions could also be used in cases where their thiocarboxylate salts are available and are sufficiently solubile in water. As such, M is the counterion to the anionic thiocarboxylate such as $G(-Y^1-S^-)_d$. Representative examples of M include, but are not limited to, sodium, potassium, ammonium, methyl ammonium, and triethyl ammonium. In one embodiment, sodium, potassium, or ammonium are used. In another embodiment, M is sodium.

L can be a halogen atom (i.e., F, Cl, Br, or I), sulfonate group, sulfinate group, or carboxylate group. From a synthetic chemical standpoint, L is any group that can function as a leaving group during nucleophilic substitution reactions. Representative examples of L are chloride, bromide, toluenesulfonate, benzenesulfonate, and methanesulfonate. L could even be a divalent group such as sulfate or phosphate. In one embodiment, L is chloro or bromo. In another embodiment, L is chloro.

The preparation of the cyclic and bridging dialkoxy blocked mercaptofunctional silane compositions can be carried out by addition of the alkoxy haloalkyl silane to an aqueous solution of the thiocarboxylate salt and agitating the mixture until the reaction has reached the desired level of completeness. Additional salts may optionally be present or be added to the aqueous thiocarboxylate salt to increase the ionic strength of the solution so as to further stabilize the silanes against hydrolysis. The level of completeness of the reaction may be monitored by any means that distinguishes the reactants from the products, such as, for example, gas chromatography (GC), liquid chromatography (LC or HPLC), nuclear magnetic resonance spectroscopy (NMR), or infrared spectroscopy (IR) of the organic phase, or wet chemical analysis of the aqueous phase. A phase transfer catalyst may be added in one or several doses and/or in a continuous manner to the thiocarboxylate salt, the alkoxy haloalkyl silane, and/or the reaction mixture before, during, and/or after the addition of the alkoxy haloalkyl silane to the aqueous thiocarboxylate salt, to accelerate the reaction.

Appropriate reaction conditions comprise temperatures from about −30 to about 300° C. and either pressures from ambient to about 100 atmospheres or vacua from ambient to about 0.01 torr. In one embodiment, the conditions are from about −10 to about 100° C. at ambient pressure. In another embodiment, the reaction temperatures are from about 25 to about 95° C. In yet another embodiment, reaction temperatures are from about 40 to about 85° C. Variable temperatures within the aforementioned ranges may be employed, as, for example, a gradual upward or downward ramping of the temperature during the course of the reaction.

Appropriate concentrations of the starting aqueous thiocarboxylate salts are from about 1 weight percent to saturation and all subranges therebetween, which can be as high as about 50 weight % or more. In another embodiment, concentrations are from about 20 to about 45 weight % and all subranges therebetween. In another embodiment, concentrations are from about 30 to about 40 weight % and all subranges therebetween. Optionally, an excess of the thiocarboxylate salt, relative to that demanded by the reaction stoichiometry, may be used to drive the reaction to completion so as to obtain a product of minimal residual alkoxy haloalkyl silane starting material, to obtain the product with minimal reaction time and/or temperature, and/or to obtain a product with minimal loss to or contamination by silane hydrolysis/condensation products. Alternatively, an excess of the alkoxy haloalkyl silane, relative to that demanded by the reaction stoichiometry, may be used to reduce the residual aqueous thiocarboxylate salt content at the completion of the reaction to a minimum.

The reactions may be run neat (i.e., without solvent) or in the presence of one or more solvents which are insoluble or have limited solubility in water. Useful solvents are ethers, for example, diethyl ether; hydrocarbons, for example, hexane, petroleum ether, toluene, and xylene; and ketones, for example, methyl ethyl ketone. In one embodiment, toluene or xylene are used. In one embodiment, the reaction is carried out in the absence of solvent (neat).

Upon completion of the reaction, the agitation is terminated, resulting in the segregation of the reaction mixture into two liquid phases. The organic phase (typically the upper phase) comprises the cyclic and bridging dialkoxy blocked mercaptofunctional silane product, and the aqueous phase comprises the co-produced salts plus any salts initially present or subsequently added to increase the ionic strength. If a starting aqueous solution of sufficient concentration was used, a solid phase may also separate comprising precipitated or crystallized salts. These salts may optionally be dissolved by addition of water so as to obtain a mixture comprising of mainly or exclusively two liquid phases. These phases can then be separated by decantation. Any solvents used during the process may then be removed by distillation or evaporation. Residual water may be removed by vacuum and/or heat stripping. Residual particulates may subsequently or concurrently be removed by filtration. Residual alkoxy haloalkyl silanes may be removed by stripping with a good vacuum at elevated temperatures.

Preparation of the Aqueous Thiocarboxylate Salts

If an aqueous solution of the thiocarboxylate salt(s) required for the preparation of the cyclic and bridging dialkoxy blocked mercaptofunctional silane composition is not available, it may be prepared in a separate step preceeding its use in the preparation of the cyclic and bridging dialkoxy blocked mercaptofunctional silane composition. Alternatively, the aqueous thiocarboxylate salt may be prepared in situ and used directly thereafter, as described above, to prepare the cyclic and bridging dialkoxy blocked mercaptofunctional silane composition.

If the thiocarboxylate salt is available, the aqueous solution thereof can simply be prepared by dissolving an effective amount of the salt into an effective amount of water to get a solution of the desired concentration, or it can be prepared by dilution or evaporative concentration of whatever solution is available. Alternatively, the desired thiocarboxylate salt or aqueous solution thereof can be prepared from another salt of the desired thiocarboxylic acid. If the thiocarboxylic acid is available, the thiocarboxylate salt or aqueous solution thereof can simply be prepared by neutralizing the acid with an appropriate base.

However, if neither the desired thiocarboxylic acid or one of its salts is available, it can be prepared by synthesis of the thiocarbonyl group by reaction of the appropriate acid halide and/or acid anhydride (e.g., acid chloride) with an aqueous solution of a sulfide, a hydrosulfide, or a mixture thereof (e.g., aqueous sodium hydrosulfide, NaSH), to yield an aqueous solution of the thiocarboxylate salt. If an aqueous mixture of thiocarboxylate salts is desired, the component thiocarboxylate salts can be blended or the appropriate mixture of acid halides and/or acid anhydrides can be used in the preparation of the thiocarboxylate salts. Mixtures of one or more acid halides and/or one or more acid anhydrides can optionally be used, as can mixtures of different sulfides and/or hydrosulfides when preparing either single-component or mixtures of aqueous thiocarboxylate salts.

Structures for the sulfides, hydrosulfides, and acid halides and acid anhydrides are given in Formulae 10-14, respectively, $$M_2S \quad \text{(Formula 10)}$$

$$MSH \quad \text{(Formula 11)}$$

$$G(-Y^1-L)_d \quad \text{(Formula 12)}$$

$$[(ROC(=O))_p-(G)_j]-Y^1-L \text{ and} \quad \text{(Formula 13)}$$

$$[(Z^c_v Z^b_w X_u Si)_q-G]-Y^1-L \quad \text{(Formula 14)}$$

wherein M, $Z^c$, $Z^b$, X, R, $Y^1$, G, L and d, j, p, q, u, v and w have the aforestated meanings.

In the descriptions of the preparation of aqueous thiocarboxylate salt solutions that follow, it is to be understood that, herein:

1) The term "acid halide" shall refer to the acid fluoride, acid chloride, acid bromide, acid iodide, acid anhydride, or mixed acid anhydride with another carboxylic acid, other organic acid, or an inorganic acid; or any mixture thereof;
2) The term "sulfide" shall refer to an alkali metal, ammonium, or substituted ammonium sulfide salt; or any mixture thereof; and
3) The term "thiocarboxylate salt" shall refer to a single-component or mixture of salts of one or more than one thiocarboxylate and/or counterion (cation).

The preparation of the aqueous thiocarboxylate salts is carried out by addition of the acid halide to an aqueous solution of the sulfide and/or hydrosulfide, and agitating the mixture. A phase transfer catalyst may be added in one or several doses and/or in a continuous manner to the aqueous sulfide and/or hydrosulfide solution, the acid halide, and/or the reaction mixture before, during, and/or after the addition of the acid halide to the aqueous sulfide and/or hydrosulfide solution, to accelerate the reaction. Appropriate reaction conditions are at temperatures from about −30 to about 250° C. and all subranges therebetween and either pressures of ambient to about 100 atmospheres and all subranges therebetween or vacuum from ambient to about 0.01 torr and all subranges therebetween. In another embodiment, the reaction conditions are from about −10 to about 100° C. and all subranges therebetween at about ambient pressure. In another embodiment, reaction temperatures are from about 20 to about 95° C. and all subranges therebetween. In another embodiment, reaction temperatures are from about 25 to about 85° C. and all subranges therebetween. Variable temperatures within the aforementioned ranges may be employed, as, for example, a gradual upward or downward ramping of the temperature during the course of the reaction, or simply allowing the temperature to rise as a result of the reaction exotherm. Appropriate concentrations of the starting aqueous sulfide and/or hydrosulfides are from about 1 weight percent to saturation, which can be as high as about 60 weight % or more. In another embodiment, concentrations are from about 10 to about 40 weight % and all subranges therebetween. In another embodiment, concentrations are from about 15 to about 25 weight % and all subranges therebetween. The reaction is usually complete when the acid halide has dissolved in the aqueous phase, an exotherm is no longer evident from this reaction, and the evolution of any hydrogen sulfide subsides. Additional salts may optionally be present or be added to the aqueous thiocarboxylate salt to increase the ionic strength of the solution. At the completion of the reaction, the solution may optionally be filtered, if necessary, to remove particulate impurities and/or crystallized coproduced salts.

Preparation of the Aqueous Sulfides and/or Hydrosulfides

These solutions can be obtained by dissolving the appropriate quantity of sulfide or hydrosulfide, or the appropriate quantity of each if a mixture is desired, into the appropriate quantity of water to obtain the desired concentration of sulfide and/or hydrosulfide. Alternatively, these solutions can be prepared by addition of hydrogen sulfide to an aqueous solution of the appropriate base. A ratio of about one or more moles of hydrogen sulfide to about one equivalent of base would yield the hydrosulfide, whereas a ratio of about one mole of hydrogen sulfide to about two equivalents of base would yield the sulfide. Ratios of one mole of hydrogen sulfide to between one and two equivalents of base would yield the corresponding mixtures of the hydrosulfide and sulfide.

Alternatively, an aqueous solution of sulfide can also be prepared by addition of about one equivalent of base to about one equivalent of aqueous hydrosulfide, and an aqueous solution of hydrosulfide can also be prepared by addition of about one or more equivalents of hydrogen sulfide to about one equivalent of aqueous sulfide. For example, aqueous sodium hydrosulfide could be prepared by addition of one mole or an excess of hydrogen sulfide to an aqueous solution comprising one mole of sodium hydroxide or sodium sulfide, and aqueous sodium sulfide could be prepared by addition of one mole of hydrogen sulfide or two moles of sodium hydrosulfide to an aqueous solution comprising two moles of sodium hydroxide.

The phase transfer catalysts used herein can accelerate the preparations by facilitating chemical reactions across the phase boundary of two immiscible liquids. The phase transfer catalysts can comprise any substance capable of facilitating transfer of reacting species, whether molecules or ions, across the phase boundary. Useful catalysts can be organic cations, which are capable of transferring sulfur anions, such as sulfide, hydrosulfide, and thiocarboxylate, from the aqueous phase into the organic phase, where these anions can then react with species in the organic phase, such as acid halides and haloalkyl silanes. The organic cations can be added as salts, or as concentrated or dilute solutions in water and/or other suitable solvents, such as alcohols. A wide variety of anions can be associated with the organic cations, e.g., fluoride, chloride, bromide, iodide, sulfate, bisulfate, carbonate, bicarbonate, hydroxide, phosphate, carboxylate, thiocarboxylate, and the like.

In one embodiment, the phase transfer catalysts may be represented by general Formula 15:

$$(R^6R^7R^8R^9N^+)_m A^{-m} \quad \text{(Formula 15)}$$

wherein
each separate occurrence of $R^6$, $R^7$, $R^8$ and $R^9$, is independently R;
N is nitrogen;
$A^{-m}$ is a monovalent or polyvalent anion, where the minus sign denotes that the species is an anion, and m denotes the number of negative charges on the anion;

the subscript m is a positive integer of from 1 to about 6.

Representative examples of $R^6$, $R^7$, $R^8$, and $R^9$ include, but are not limited to, branched and straight-chain alkyls, e.g., methyl, ethyl, propyl, isopropyl, butyl, isobutyl, hexyl, octyl, decyl, dodecyl, tetradecyl, octadecyl, phenyl, benzyl, tolyl, cyclohexyl, methylcyclohexyl, and allyl. In one embodiment, $R^6$, $R^7$, $R^8$, and $R^9$ are independently selected from methyl, ethyl, butyl, and octyl.

Representative examples of $A^{-m}$ include, but are not limited to, fluoride, chloride, bromide, iodide, sulfate, bisulfate, carbonate, bicarbonate, hydroxide, phosphate, carboxylate, and thiocarboxylate, sulfide, hydrosulfide and the like. In one embodiment, A is chloride. In another embodiment, $A^{-m}$ is bromide. In another embodiment, $A^{-m}$ is hydroxide.

Representative examples of suitable phase transfer catalysts include, but are not limited to, tetramethylammonium chloride, tetramethylammonium bromide, tetramethylammonium iodide, tetramethylammonium hydroxide, tetraethylammonium chloride, tetraethylammonium bromide, tetraethylammonium iodide, tetraethylammonium hydroxide, tetrabutylammonium chloride, tetrabutylammonium bromide, tetrabutylammonium iodide, tetrabutylammonium hydroxide, methyltributylammonium chloride, methyltributylammonium bromide, methyltributylammonium iodide, methyltributylammonium hydroxide, tetraoctylammonium chloride, tetraoctylammonium bromide, tetraoctylammonium iodide, tetraoctylammonium hydroxide, methyltrioctylammonium chloride, methyltrioctylammonium bromide, methyltrioctylammonium iodide, methyltrioctylammonium hydroxide, benzyltrimethylammonium chloride, benzyltrimethylammonium bromide, benzyltriethylammonium chloride, benzyltributylammonium chloride, dibenzyldimethylammonium chloride, dibenzyldiimethylammonium bromide, dibenzyldiethylammonium chloride, dibenzyldibutylammonium chloride, and the like and aqueous solutions thereof.

In one embodiment, the phase transfer catalysts are aqueous solutions of tetraethylammonium chloride, tetrabutylammonium chloride, tetrabutylammonium bromide, tetrabutylammonium hydroxide, methyltributylammonium chloride, tetraoctylammonium chloride, tetraoctylammonium bromide, methyltrioctylammonium bromide, methyltrioctylammonium iodide, methyltrioctylammonium hydroxide, benzyltrimethylammonium chloride, benzyltriethylammonium chloride, benzyltributylammonium chloride, dibenzyldiethylammonium chloride, and dibenzyldibutylammonium chloride.

In another embodiment, the phase transfer catalysts are aqueous solutions of tetraethylammonium chloride, tetrabutylammonium chloride, tetrabutylammonium bromide, tetrabutylammonium hydroxide, methyltributylammonium chloride, tetraoctylammonium chloride, methyltrioctylammonium chloride, methyltrioctylammonium bromide, methyltrioctylammonium hydroxide, benzyltriethylammonium chloride, benzyltributylammonium chloride, and dibenzyldibutylammonium chloride.

The phase transfer catalyst can be added at any point during the reaction, either all at once, in two or more doses, or in a continuous or semi-continuous manner, or as any combination thereof. A single phase transfer catalyst may be used, or a combination of several, added as a blend, as individual components, or any combination thereof. Different catalysts may optionally be added at different points along the entire reaction sequence. The phase transfer catalyst(s) may be added only in the first step, in which aqueous sulfide and/or hydrosulfide is reacted with the acid halide; or only in the second step, in which the aqueous thiocarboxylate is reacted with the haloalkyl silane. Alternatively, the phase transfer catalyst(s) may be added in both steps at the same or different levels.

As one skilled in the art will readily appreciate, the quantity of phase transfer catalyst to be used depends on the desired rate of reaction and the level of side products that can be tolerated, among other factors. Alternative, the reactions can be run without a phase transfer catalyst. However, if a phase transfer catalyst is used, appropriate concentrations to be used during the reactions can range from a concentration of about 1 ppm (part per million, by weight) to about 3 percent by weight and all subranges therebetween. In one embodiment, concentrations of the phase transfer catalyst can range from about 10 ppm to about 1 weight percent and all subranges therebetween. In another embodiment, the concentrations of the phase transfer catalyst can range from about 50 ppm to about 0.5 weight percent and all subranges therebetween. Quantities below about 1 ppm of phase transfer catalyst can also be used, but this will give results similar to that obtained without the use of a phase transfer catalyst.

Preparation of Cyclic and Bridging Dialkoxy Blocked Mercaptofunctional Silanes Transesterification Method for Thiocarboxylate Silanes The preparation of the cyclic and bridging dialkoxy blocked mercaptofunctional silanes generally involves at least a transesterification reaction between a neat thiocarboxylate-alkoxy silane and a diol. The reaction may be carried out by catalyzing a mixture of thiocarboxylate-alkoxy silane and a diol at a molar ratio of about 0.5 moles of diol per alkoxy-silyl group to be transesterified or cam range from about 0.5 to about 1.5 for a trialkoxy silane. In one embodiment, the ratio can range from about 1.0 to about 1.5 for a trialkoxy silane. The reaction can be carried out at a temperature ranging from about 10 to about 150° C. and all subranges therebetween while maintaining a pressure in the range of 0.1 to 2000 mm Hg absolute. In one embodiment, the temperature can range from about 30° C. to about 90° C. and all subranges therebetween. In another embodiment, the pressure can range from about 1 to about 80 mm Hg absolute. As those skilled in the art will recognize, excess diol could be utilized to increase reaction rate, but it is not necessary under these conditions as it increases the cost. The reaction may be carried out by slowly adding diol to catalyzed thiocarboxylate silane at the desired reaction temperature and vacuum. In this manner, the reaction has better selectivity, is better controlled, and has a shorter reaction and distillation cycle. If desired, a neutralization step may be utilized to neutralize an acid or base catalyst and improve product storage. Stripping of residual alcohol following neutralization may be conducted in a batch mode or can be run in continuous distillation equipment.

The thiocarboxylate silane transesterification advantageously proceeds without degradation or substitution of the thiol group. Additionally, the products of the transesterification of thiocarboxylate silane can comprise a considerable fraction of monomeric material with secondary formation of dimers and other low molecular weight cyclic and bridged oligomers as illustrated by low viscosity reaction products. Also, resin or gel formation can be substantially reduced or not present at all.

Optionally, an inert solvent may be used in the process. The solvent may serve as a diluent, carrier, stabilizer, refluxing aid, or heating agent. Generally any inert solvent which does not enter into the reaction or adversely affect the reaction may be used. In one embodiment, the solvents are those which are liquid under normal conditions and have a boiling point below about 150° C. Examples include aromatic, hydrocarbon, ether, aprotic, or chlorinated hydrocarbon solvents such as toluene, xylene, hexane, butane, diethyl ether, dimethylformamide, dimethyl sulfoxide, carbon tetrachloride, methylene chloride, and the like.

Alternatively, the transesterification process may be conducted continuously. In this case the process comprises:
a) reacting, in a thin film reactor, a thin film reaction medium comprising an organofunctional silane, e.g., a thiocarboxylate silane, a diol and a catalyst to provide diol-derived organofunctional silanes and by-product alcohol;
b) vaporizing the by-product alcohol from the thin film to drive the reaction;
c) recovering the diol-derived organofunctional silane reaction product;
d) optionally, recovering the by-product alcohol by condensation; and,
e) optionally, neutralizing the diol-derived organofunctional silane product to improve its storage stability.

The molar ratio of diol to thiocarboxylate silane used in the continuous thin film process will depend upon the number of alkoxy groups that are desired to be replaced with a diol group. Theoretically, a molar ratio of about 0.5 moles of diol is required per alkoxy-silyl group to be transesterified. For a trialkoxy silane, the stoichiometric equivalent molar ratio is about 1, wherein one diol replaces two alkoxy groups. Generally, the necessary molar ratio operates close to theoretical. The molar ratio of diol to thiocarboxylate silane can vary, e.g., within a range of about 95 to about 125 percent and all subranges therebetween of stoichiometric equivalence for each alkoxy-silyl group to be transesterified. In one embodiment, the molar ratio of diol to thiocarboxylate silane can range from about 100 to about 110 percent of stoichiometric equivalence and all subranges therebetween. In another embodiment, a range of about 100 to about 105 percent of stoichiometric equivalence and all subranges therebetween for the molar ratio of diol to thiocarboxylate can be used. As one skilled in the art will readily recognize, excess diol can be utilized to increase reaction rates, but it is not necessary when conducting the reaction in a thin film and it is not economical.

The method of forming the film can be any of those known in the art. Typical known devices include but are not limited to, falling film or wiped film evaporators. Minimum film thickness and flow rates will depend on the minimum wetting rate for the film forming surface. Maximum film thickness and flow rates will depend on the flooding point for the film and device. Vaporization of the alcohol from the film is effected by heating the film, by reducing pressure over the film, or by a combination of both. In one embodiment, mild heating and reduced pressure are utilized to form the structures of this invention. Optimal temperatures and pressures (partial vacuum) for running this process will depend upon the specific thiocarboxylate silane's alkoxy groups and the diol or dialcoholamine used in the process. Additionally if an optional inert solvent is used in the process, that choice will affect the optimal temperatures and pressures (partial vacuum) utilized. Examples of such solvents include those listed above.

The byproduct alcohol vaporized from the film is removed from the reactive distillation device by a standard partial vacuum-forming device and can be condensed, collected, and recycled as feed to other processes. The silane product is recovered by standard means from the reactive distillation device as a liquid phase. If an inert solvent has been used or if additional purification is necessary, the silane product may be fed to another similar distillation device or distillation column to effect that separation. Optionally the product may be neutralized to improve product storage.

Utility of Cyclic and Bridging Dialkoxy Blocked Mercaptofunctional Silanes

The cyclic and bridging dialkoxy blocked mercaptofunctional silane compositions described herein are useful as coupling agents between organic polymers (i.e. rubbers) and inorganic fillers. The cyclic and bridging dialkoxy blocked mercaptofunctional silanes are unique in that the high efficiency of the mercapto group can be utilized without the detrimental side effects typically associated with the use of mercaptosilanes such as, for example, high processing viscosity, less than desirable filler dispersion, premature curing (scorch), and odor. These benefits are obtained because the mercaptan group initially is non-reactive because of the blocking group. The blocking group substantially prevents the silane from coupling to the organic polymer during the compounding of the rubber. Generally, only the reaction of the alkoxysilane group with the filler can occur at this stage of the compounding process. Thus, substantial coupling of the filler to the polymer is precluded during mixing, thereby minimizing the undesirable premature curing (scorch) and the associated undesirable increase in viscosity. One can achieve better cured filled rubber properties such as, for example, a balance of high modulus and abrasion resistance, because of the avoidance of premature curing.

The cyclic and bridging dialkoxy blocked mercaptofunctional silane coupling agents herein provide significant advantages over traditional coupling agents that have found extensive use in the known art. These all comprise in their molecular structures three ethoxy groups on each silicon atom, which results in the release of up to three moles of ethanol for each silane equivalent during the rubber manufacturing process in which the silane silicon couples to the filler. The release of this ethanol is a great disadvantage because it is flammable and therefore poses a threat of fire, and because it contributes so greatly to volatile organic compound (VOC) emissions and is therefore potentially harmful to the environment. The cyclic and bridging dialkoxy blocked mercaptofunctional silane coupling agent compositions described herein eliminate or greatly mitigate this problem by capping the ethanol emissions to only one, less than one, or even essentially zero moles of ethanol per silane equivalent. They accomplish this because the silane ethoxy groups are replaced with diol-derived alkoxy groups and thus diols are released during the rubber manufacture process in place of much, or nearly all, of the ethanol released. The diols, having boiling points well in excess of rubber processing temperatures, are not vaporized out of the rubber during the rubber manufacture process, as is the ethanol, but are retained by the rubber where they migrate to the silica surface due to their high polarity and become hydrogen bonded to the also polar silica surface. The presence of the diols on the silica surface then leads to further advantages not obtainable with ethanol (due to its volatility and ejection during the rubber compounding process) in the subsequent cure process, in which such presence prevents the silica surface from binding the curatives and thereby interfering with the cure. Traditional silanes not based on diols require more curatives to counter losses due to silica binding.

The addition of hydrocarbon-based diols to the rubber compounding formulation prior to and/or concurrent with the addition of curatives is of advantage for the efficient utilization of the curatives, in particular, and polar substances, such as (but not limited to) amines, amides, sulfenamides, thiurams, and guanidines. Whether diols are exclusively added in the form of diol-derived silanes or as free diols in combination with the silane coupling agents, the polarity of the diols is of advantage to the rubber compounding process. These polar substances tend to migrate to the filler surface due to dipole interactions with the filler. This tends to make them unavailable for their intended function within the organic polymer matrix, where their functions include such things as vulcanization and/or coupling initiatiation, acceleration, retardation, or sulfur atom transfer and/or activation. The hydrocarbon-based diols enhance the function of the curatives by interfering with their tendency to bind to the silica surface, thereby forcing them into the rubber matrix to perform their function. The hydrocarbon-based diols accomplish this by themselves being very polar, and thereby by themselves binding to the filler surface, leaving less room for the curatives to bind to filler. The hydrocarbon based diols thus act as curative displacing agents from the filler.

The short chain of the hydrocarbon-based diols can further enhance their function by a chelate effect. Chains of two or three carbon atoms between the two OH groups of the diol promote the formation of 5- or 6-membered rings when both oxygen atoms bind to a common atom, such as a proton residing on the filler. This dual binding to a common center, known as, and referred to herein as, the chelate effect, enhances the affinity of the diol to the filler and thereby enhances its ability to prevent the binding of the curatives to the filler.

The hydrocarbon-based diols used herein are superior to ether- and/or polyether-based monofunctional alcohols or difunctional alcohols (diols) because the lack of the ether functionality of the hydrocarbon based diols avoids the problems typically encountered with ethers. These problems include high toxicity, their tendency for spontaneous peroxide formation, and high chain lengths between OH groups. Spontaneous peroxide formation is a problem because it is difficult to prevent and because the peroxides lead to flammability hazards. Furthermore, the peroxides decompose when heated to free radicals, which can initiate unwanted side reactions in the rubber polymers. These side reactions include peroxide-induced cure chemistries, in which polymer chains are crosslinked. This can lead to premature, excess, and variable crosslinking during or prior to cure. The excess crosslinking can lead to inferior properties in the rubber, premature crosslinking can lead to scorch, and the variability makes it hard to fabricate a reproducible rubber composition and any articles of manufacture derived thereof.

The excess chain lengths of the ether-comprising diols forces chelation by the two OH groups to involve ring sizes of at least about 8 atoms, which is well beyond the optimum 5 or 6, accessible to hydrocarbon based diols. Chelation involving an OH group and an ether, which would give the optimum 5 or 6 membered rings, is not as strong as chelation with the two OH groups accessible to the hydrocarbon based diols because the OH groups are less sterically hindered and because the OH groups are more active at forming hydrogen bond interactions, which are key to binding the diols to the filler surface.

The silanes used herein are advantageously designed so that the byproducts of the silane coupling process are themselves of utility in enhancing the rubber compounding process, the value of the derived rubber composition, and/or any articles of manufacture derived from the rubber composition. Thus, 1) the sulfur portion of the coupling agent comprises a blocking group which not only retards coupling of silane to polymer during mixing, activating the sulfur only during the cure, but the blocking group also functions by compatibilizing the filler with the polymer during mixing through the hydrophobic interactions with the polymer, thereby enhancing the ease and completeness filler dispersion and retarding the reversal of this process, namely filler reagglomeration (Payne Effect); and 2) the diols released from the silane silicon during the process of coupling to the filler are not just shed as a waste product, but perform an important follow-up function. This function relates to enhancing the efficiency of the curatives, which was described above.

In use, at least one of the cyclic and bridging dialkoxy blocked mercaptofunctional silane compositions of the present invention is mixed with the organic polymer before, during, or after the compounding of the filler into the organic polymer. It is advantageous to add the silanes before or during the compounding of the filler into the organic polymer because these silanes facilitate and improve the dispersion of the filler. The total amount of the silane composition present in the resulting combination can range from about 0.05 to about 25 parts by weight per hundred parts by weight of organic polymer (phr) and all subranges therebetween. In another embodiment, the total amount of silane present in the resulting combination can range from about 1 to about 10 phr and all subranges therebetween. Fillers can be used in quantities ranging from about 5 to about 100 phr and all subranges therebetween. In another embodiment, the filler can be used in an amount ranging from about 25 to about 80 phr and all subranges therebetween.

When reaction of the mixture to couple the filler to the polymer is desired, a deblocking agent is added to the mixture to deblock the cyclic and bridging dialkoxy blocked mercaptofunctional silanes. The deblocking agent may be added at quantities ranging from about 0.1 to about 5 phr and all subranges therebetween. In another embodiment, the deblocking agent can be used in an amount ranging from about 0.5 to about 3 phr and all subranges therebetween. If alcohol or water are present in the mixture (as is common), a catalyst (e.g., tertiary amines, Lewis acids, or thiols) may be used to initiate and promote the loss of the blocking group by hydrolysis or alcoholysis to liberate the corresponding mercaptosilane. Alternatively, the deblocking agent may be a nucleophile comprising a hydrogen atom sufficiently labile such that hydrogen atom could be transferred to the site of the original blocking group to form the mercaptosilane. Thus, with a blocking group acceptor molecule, an exchange of hydrogen from the nucleophile would occur with the blocking group of the blocked mercaptosilane to form the mercaptosilane and the corresponding derivative of the nucleophile comprising the original blocking group. This transfer of the blocking group from the silane to the nucleophile could be driven by, for example, a greater thermodynamic stability of the products (mercaptosilane and nucleophile comprising the blocking group) relative to the initial reactants (cyclic and bridging dialkoxy blocked mercaptofunctional silanes and nucleophile). For example, if the nucleophile were an amine comprising an N—H bond, transfer of the blocking group from the cyclic and bridging dialkoxy blocked mercaptofunctional silane would yield the mercaptosilane and one of several classes of amides corresponding to the type of blocking group used. For example, carboxyl blocking groups deblocked by amines would yield amides, sulfonyl blocking groups deblocked by amines would yield sulfonamides, sulfinyl blocking groups deblocked by amines would yield sulfinamides, phosphonyl blocking groups deblocked by amines would yield phosphonamides, and phosphinyl blocking groups deblocked by amines would yield phosphinamides. What is important is that regardless of the blocking group initially present on the cyclic and bridging dialkoxy blocked mercaptofunctional silane and regardless of the deblocking agent used, the initially substantially inactive (from the standpoint of coupling to the organic polymer) cyclic and bridging dialkoxy blocked mercaptofunctional silane is substantially converted at the desired point in the rubber compounding procedure to the active mercaptosilane. It is noted that partial amounts of the nucleophile may be used (i.e., a stoichiometric deficiency), if one were to only deblock part of the cyclic and bridging dialkoxy blocked mercaptofunctional silane composition to control the degree of vulcanization of a specific formulation.

Water typically is present on the inorganic filler as a hydrate or bound to a filler in the form of a hydroxyl group. The deblocking agent can be added in the curative package or, alternatively, at any other stage in the compounding process as a single component. Examples of nucleophiles would include any primary or secondary amines, or amines comprising C=N double bonds, e.g., imines, guanidines and the like; with the proviso that the amine comprises at least one N—H (nitrogen-hydrogen) bond. Numerous examples of guanidines, amines, and imines well known in the art, which are useful as components in curatives for rubber, are cited in Rubber Chemicals; J. Van Alphen; Plastics and Rubber Research Institute TNO, Delft. Holland; 1973. Representative examples include, but are not limited to, N,N'-diphenylguanidine, N,N',N"-triphenylguanidine, N,N'-di-ortho-tolylguanidine, ortho-biguanide, hexamethylenetetramine, cyclohexylethylamine, dibutylamine, 4,4'-diaminodiphenylmethane and the like. Any general acid catalysts used to transesterify esters, such as Bronsted or Lewis acids, could be used as catalysts.

The rubber composition need not be, but usually is, substantially free of functionalized siloxanes, especially those of the type disclosed in Australian Patent AU-A-10082/97, which is incorporated herein by reference. In one embodiment, the rubber composition is free of functionalized siloxanes.

In practice, sulfur vulcanized rubber products typically are prepared by thermomechanically mixing rubber and various ingredients in a sequentially step-wise manner followed by shaping and curing the compounded rubber to form a vulcanized product. First, for the aforesaid mixing of the rubber and various ingredients, typically exclusive of sulfur and sulfur vulcanization accelerators (collectively "curing agents"), the rubber(s) and various rubber compounding ingredients are usually blended in at least one, and often (in the case of silica filled low rolling resistance tires) two, preparatory thermomechanical mixing stage(s) in suitable mixers. Such preparatory mixing is referred to as non-productive mixing or non-productive mixing steps or stages. Such preparatory mixing usually is conducted at temperatures in the range of from about 140° C. to about 20° C. and all subranges therebetween and often in the range of from about 150° C. to about 180° C. and all subranges therebetween.

Subsequent to such preparatory mix stages, in a final mixing stage, sometimes referred to as a productive mix stage, deblocking agent (in the case of this invention), curing agents, and possibly one or more additional ingredients, are mixed with the rubber compound or composition, typically at a temperature in a range of about 50° C. to about 130° C., which is a lower temperature than those utilized in the preparatory mix stages to prevent or retard premature curing of the sulfur curable rubber, which is sometimes referred to as scorching of the rubber composition.

The rubber mixture, sometimes referred to as a rubber compound or composition, typically is allowed to cool, sometimes after or during a process intermediate mill mixing, between the aforesaid various mixing steps, for example, to a temperature of about 50° C. or lower.

When it is desired to mold and to cure the rubber, the rubber is placed into the appropriate mold at about at least about 130° C. and up to about 200° C., which will cause the vulcanization of the rubber by the mercapto groups on the mercaptosilane and any other free sulfur sources in the rubber mixture.

By thermomechanical mixing, it is meant that the rubber compound, or composition of rubber and rubber compounding ingredients, is mixed in a rubber mixture under high shear conditions where it autogenously heats up as a result of the mixing, primarily due to shear and associated friction within the rubber mixture in the rubber mixer. Several chemical reactions may occur at various steps in the mixing and curing processes.

The first reaction is a relatively fast reaction and is considered herein to take place between the filler and the alkoxysilane group of the cyclic and bridging dialkoxy blocked mercaptofunctional silanes. Such reaction may occur at a relatively low temperature, such as, for example, about 120° C. The second and third reactions are considered herein to be the deblocking of the cyclic and bridging dialkoxy blocked mercaptofunctional silanes and the reaction which takes place between the sulfur portion of the organosilane (after deblocking), and the sulfur vulcanizable rubber at a higher temperature: for example, above about 140° C.

Another sulfur source may be used, for example, in the form of elemental sulfur as $S_g$. A sulfur donor is considered herein as a sulfur-containing compound that liberates free, or elemental sulfur, at a temperature in a range of about 140° C. to about 190° C. Such sulfur donors may be, for example, although are not limited to, polysulfide vulcanization accelerators and organosilane polysulfides with at least two connecting sulfur atoms in their polysulfide bridge. The amount of free sulfur source addition to the mixture can be controlled or manipulated as a matter of choice relatively independently from the addition of the aforesaid cyclic and bridging dialkoxy blocked mercaptofunctional silane composition.

Thus, for example, the independent addition of a sulfur source may be manipulated by the amount of addition thereof and by sequence of addition relative to addition of other ingredients to the rubber mixture.

Addition of an alkyl silane to the coupling agent system (cyclic and bridging dialkoxy blocked mercaptofunctional silane plus additional free sulfur source and/or vulcanization accelerator) typically in a mole ratio range of alkyl silane to cyclic and bridging dialkoxy blocked mercaptofunctional silane of about 1/50 to about 1/2 promotes an even better control of rubber composition processing and aging.

A rubber composition is prepared by a process comprising the sequential steps of:
  a) thermomechanically mixing, in at least one preparatory mixing step, under effective mixing conditions, e.g., at a temperature from about 120° C. to about 200° C. and all subranges therebetween in a first embodiment and from about 140° C. to about 190° C. and all subranges therebetween in a second embodiment, for a total mixing time of from about 2 to about 20 minutes and all subranges therebetween in a first embodiment and from about 4 to about 15 minutes and all subranges therebetween in a second embodiment for such mixing step(s):
    i) about 100 parts by weight of at least one sulfur vulcanizable rubber selected from conjugated diene homopolymers and copolymers, and copolymers of at least one conjugated diene and aromatic vinyl compound, ii) from about 5 to about 100 phr and all subranges therebetween of a particulate filler in a first embodiment and from about 25 to about 80 phr and all subranges therebetween of a particulate filler in a second embodiment, wherein the particulate filler can comprise from about 1 to about 85 weight percent and all subranges therebetween carbon black, and iii) from about 0.05 to about 20 parts by weight of filler (ii) and all subranges therebetween of at least one cyclic and bridging dialkoxy organofunctional silane composition; and, optionally, b) subsequently blending therewith, in a final thermomechanical mixing step under effective blending conditions, e.g., at a temperature of from about 50° C. to about 130° C. for a time sufficient to blend the rubber, e.g., from about 1 to about 30 minutes in a first embodiment and from about 1 to about 3 minutes in a second embodiment, at least one deblocking agent at about 0.05 to about 20 parts by weight of the filler and all subranges therebetween and at least one curing agent at 0 to about 5 phr and all subranges therebetween; and, optionally, c) curing the mixture under effective curing conditions, e.g., at a temperature of from about 130° C. to about 200° C. and all subranges therebetween for a period of from about 5 to about 60 minutes and all subranges therebetween.

The process may also comprise the additional steps of preparing an assembly of a tire or sulfur vulcanizable rubber with a tread comprised of the rubber composition prepared according to this invention and vulcanizing the assembly at a temperature in a range of about 130° C. to about 200° C. and all subranges therebetween.

Suitable organic polymers and fillers for use herein are well known in the art and are described in numerous texts, of which two examples include The Vanderbilt Rubber Handbook; R. F. Ohm, ed.; R.T. Vanderbilt Company, Inc., Norwalk, Conn.; 1990 and Manual For The Rubber Industry; T. Kempermann, S. Koch, J. Sumner, eds.; Bayer AG, Leverkusen, Germany; 1993. Representative examples of suitable polymers include solution styrene-butadiene rubber (SSBR), styrene-butadiene rubber (SBR), natural rubber (NR), polybutadiene rubber (BR), ethylene-propylene co- and ter-polymers (EP, EPDM), and acrylonitrile-butadiene rubber (NBR).

Generally, the rubber composition can be comprised of at least one diene-based elastomer, or rubber. Suitable conjugated dienes include, but are not limited to, isoprene, 1,3-butadiene and the like and mixtures thereof. Suitable vinyl aromatic compounds include, but are not limited to, styrene, alpha methyl styrene and the like and mixtures thereof. Thus, the rubber is a sulfur curable rubber. Such diene based elastomer, or rubber, may be selected, for example, from at least one of cis-1,4-polyisoprene rubber (natural and/or synthetic), and natural rubber), emulsion polymerization prepared styrene/butadiene copolymer rubber, organic solution polymerization prepared styrene/butadiene rubber, e.g., of from about 10 to about 80 weight percent vinyl content in one embodiment, from about 25 to about 48 weight percent vinyl content in a second embodiment and from about 53 to about 75 weight percent vinyl content in a third embodiment, 3,4-polyisoprene rubber, isoprene/butadiene rubber, styrene/isoprene/butadiene terpolymer rubber, polybutadiene rubber of low cis-1,4 content (i.e., from about 5 to about 19 weight percent), medium cis-1,4 content (i.e., from about 20 to about 89 weight percent) or high cis-1,4 content (i.e., at least about 90 weight percent), and a vinyl content of from 0 to about 50 weight percent, styrene/isoprene copolymers, emulsion polymerization prepared styrene/butadiene/acrylonitrile terpolymer rubber and butadiene/acrylonitrile copolymer rubber. An emulsion polymerization derived styrene/butadiene (E-SBR) may be used having a relatively conventional styrene content of from about 20 to about 28 weight percent bound styrene or, for some applications, an E-SBR having a medium to relatively high bound styrene content, namely, a bound styrene content of from about 30 to about 45 weight percent. Emulsion polymerization prepared styrene/butadiene/acrylonitrile terpolymer rubbers comprising from 2 to about 40 weight percent bound acrylonitrile in the terpolymer are also contemplated as diene based rubbers for use in this invention.

The solution polymerization prepared SBR (S-SBR) typically has a bound styrene content of up to about 50 percent in one embodiment and from about 5 to about 36 percent in another embodiment.

Representative examples of suitable filler materials include metal oxides, such as silica (pyrogenic and precipitated), titanium dioxide, aluminosilicate, and alumina, siliceous materials, including clays and talc, and carbon black. Particulate, precipitated silica is also sometimes used for such purpose, particularly in connection with a silane. In some cases, a combination of silica and carbon black is utilized for reinforcing fillers for various rubber products, including treads for tires. Alumina can be used either alone or in combination with silica. The term "alumina" can be described herein as aluminum oxide, or $Al_2O_3$. The fillers may be hydrated or in anhydrous form. Use of alumina in rubber compositions is known, see, for example, U.S. Pat. No. 5,116,886 and EP 631 982.

The cyclic and bridging dialkoxy blocked mercaptofunctional silane compositions may be premixed, or pre-reacted, with the filler particles or added to the rubber mix during the rubber and filler processing, or mixing stage. If the silane and filler are added separately to the rubber mix during the rubber and filler mixing, or processing stage, it is considered that the cyclic and bridging dialkoxy blocked mercaptofunctional silanes then couple in situ to the filler.

The vulcanized rubber composition should comprise a sufficient amount of filler to contribute a reasonably high modulus and high resistance to tear. The combined weight of the filler may be as low as about 5 to about 100 ph and all subranges therebetween r, but it can be from about 25 to about 85 phr and all subranges therebetween in another embodiment.

In one embodiment precipitated silicas are utilized as a filler. The silica may be characterized by having a BET surface area, as measured using nitrogen gas, in the range of about 40 to about 600, and more usually in a range of about 50 to about 300 m²/g. The BET method of measuring surface area is described in the *Journal of the American Chemical Society*, Volume 60, page 304 (1930). The silica typically may also be characterized by having a dibutylphthalate (DBP) absorption value in a range of about 100 to about 350, and more usually about 150 to about 300. Further, the silica, as well as the aforesaid alumina and aluminosilicate, may be expected to have a CTAB surface area in a range of about 100 to about 220. The CTAB surface area is the external surface area as evaluated by cetyl trimethylammonium bromide with a pH of about 9. The method is described in ASTM D 3849.

Mercury porosity surface area is the specific surface area determined by mercury porosimetry. For such technique, mercury is penetrated into the pores of the sample after a thermal treatment to remove volatiles. Set up conditions may be suitably described as using about a 100 mg sample, removing volatiles during about 2 hours at about 105° C. and ambient atmospheric pressure to about 2000 bars pressure measuring range. Such evaluation may be performed according to the method described in Winslow, Shapiro in ASTM bulletin, p. 39 (1959) or according to DIN 66133. For such an evaluation, a CARLO-ERBA Porosimeter 2000 might be used. The average mercury porosity specific surface area for the silica should be in a range of about 100 to about 300 m²/g.

In one embodiment a suitable pore size distribution for the silica, alumina and aluminosilicate according to such mercury porosity evaluation is considered herein to be five percent or less of its pores have a diameter of less than about 10 nm; about 60 to about 90 percent of its pores have a diameter of about 10 to about 100 nm; about 10 to about 30 percent of its pores have a diameter at about 100 to about 1,000 nm; and about 5 to about 20 percent of its pores have a diameter of greater than about 1,000 nm.

In a second embodiment the silica may be expected to have an average ultimate particle size, for example, in the range of about 0.01 to about 0.05 μm as determined by the electron microscope, although the silica particles may be even smaller, or possibly larger, in size. Various commercially available silicas may be considered for use in this invention such as, from PPG Industries under the HI-SIL trademark with designations HI-SIL 210, 243, etc.; silicas available from Rhone-Poulenc, with, for example, designation of ZEOSIL 1165 MP; silicas available from Degussa with, for example, designations VN2 and VN3, etc. and silicas commercially available from Huber having, for example, a designation of HUBER-SIL 8745.

Where it is desired for the rubber composition, which comprises both a siliceous filler such as silica, alumina and/or aluminosilicates and also carbon black reinforcing pigments, to be primarily reinforced with silica as the reinforcing pigment, the weight ratio of such siliceous fillers to carbon black can be about at least 3/1 in one embodiment, about at least 10/1 in another embodiment and, thus, in a range of about 3/1 to about 30/1. The filler may be comprised of about 15 to about 95 weight percent precipitated silica; alumina and/or aluminosilicate and, correspondingly about 5 to about 85 weight percent carbon black, wherein the carbon black has a CTAB value in a range of about 80 to about 150. Alternatively, the filler can be comprised of about 60 to about 95 weight percent of the silica and all subranges therebetween, alumina and/or aluminosilicate and, correspondingly, about 40 to about 5 weight percent carbon black and all subranges therebetween. The siliceous filler and carbon black may be pre-blended or blended together in the manufacture of the vulcanized rubber.

The rubber composition may be compounded by methods known in the rubber compounding art, such as mixing the various sulfur-vulcanizable constituent rubbers with various commonly used additive materials such as, for example, curing aids, such as sulfur, activators, retarders and accelerators, processing additives, such as oils, resins including tackifying resins, silicas, plasticizers, fillers, pigments, fatty acid, zinc oxide, waxes, antioxidants and antiozonants, peptizing agents, and reinforcing materials such as, for example, carbon black. Depending on the intended use of the sulfur vulcanizable and sulfur vulcanized material or rubber, the additives mentioned above are selected and commonly used in conventional amounts.

The vulcanization may be conducted in the presence of an additional sulfur vulcanizing agent. Examples of suitable sulfur vulcanizing agents include, for example elemental sulfur (free sulfur) or sulfur donating vulcanizing agents, for example, an amino disulfide, polymeric polysulfide or sulfur olefin adducts which are conventionally added in the final, productive, rubber composition mixing step. The sulfur vulcanizing agents, which are common in the art are used, or added in the productive mixing stage, in an amount ranging from about 0.4 to about 3 phr and all subranges therebetween, or even, in some circumstances, up to about 8 phr, with a range of from about 1.5 to about 2.5 phr and all subranges therebetween in one embodiment and from about 2 to about 2.5 phr and all subranges therebetween in another embodiment.

Vulcanization accelerators, i.e., additional sulfur donors, may be used herein. It is appreciated that may include the following examples, benzothiazole, alkyl thiuram disulfide, guanidine derivatives and thiocarbamates. Representative of such accelerators can be, but not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine) and dithiobis(dibenzyl amine). Other additional sulfur donors may be, for example, thiuram and morpholine derivatives. Representative of such donors are, for example, but not limited to, dimorpholine disulfide, dimorpholine tetrasulfide, tetramethyl thiuram tetrasulfide, benzothiazyl-2,N-dithiomorpholide, thioplasts, dipentamethylenethiuram hexasulfide, and disulfidecaprolactam.

Accelerators are used to control the time and/or temperature required for vulcanization and to improve the properties of the vulcanizate. In one embodiment, a single accelerator system may be used, i.e., a primary accelerator. Conventionally, a primary accelerator(s) is used in total amounts ranging from about 0.5 to about 4 and all subranges therebetween in one embodiment, and from about 0.8 to about 1.5 phr and all subranges therebetween in another embodiment. Combinations of a primary and a secondary accelerator might be used with the secondary accelerator being used in smaller amounts (of about 0.05 to about 3 phr and all subranges therebetween) in order to activate and to improve the properties of the vulcanizate. Delayed action accelerators may be used. Vulcanization retarders might also be used. Suitable types of accelerators are amines, disulfides, guanidines, thioureas, thiazoles, thiurams, sulfenamides, dithiocarbamates and xanthates. In one embodiment, the primary accelerator is a sulfenamide. If a second accelerator is used, the secondary accelerator can be a guanidine, dithiocarbamate or thiuram compound.

Typical amounts of tackifier resins, if used, comprise about 0.5 to about 10 phr and all subranges therebetween, usually about 1 to about 5 phr and all subranges therebetween. Typical amounts of processing aids comprise about 1 to about 50 phr and all subranges therebetween. Such processing aids can include, for example, aromatic, napthenic, and/or paraffinic processing oils. Typical amounts of antioxidants comprise about 1 to about 5 phr. Representative antioxidants may be, for example, diphenyl-p-phenylenediamine and others, such as, for example, those disclosed in the *Vanderbilt Rubber Handbook* (1978), pages 344-346. Typical amounts of antiozonants, comprise about 1 to about 5 phr and all subranges therebetween. Typical amounts of fatty acids, if used, which can include stearic acid, comprise about 0.5 to about 3 phr and all subranges therebetween. Typical amounts of zinc oxide comprise about 2 to about 5 phr and all subranges therebetween. Typical amounts of waxes comprise about 1 to about 5 phr and all subranges therebetween. Often microcrystalline waxes are used. Typical amounts of peptizers comprise about 0.1 to about 1 ph and all subranges therebetween r. Typical peptizers may be, for example, pentachlorothiophenol and dibenzamidodiphenyl disulfide.

The rubber compositions of this invention can be used for various purposes. For example, it can be used for various tire compounds. Such tires can be built, shaped, molded and cured by various methods, which are known and will be readily apparent to those having skill in such art. One particularly useful application of the rubber compositions herein is for the manufacture of tire treads. An advantage of tires, tire treads, of other articles of manufacture derived from the rubber compositions herein is they suffer from less VOC emissions during their lifetime and use as a result of having been manufactured from a rubber compound which comprises less residual silane ethoxy groups than do rubber compounds of the known and presently practiced art. This is a direct result of having used dialkoxy-functional silane coupling agents in their manufacture, which comprise fewer or essentially no ethoxy groups on silicon, relative to the silane coupling agents of the currently known and practiced art. The lack or reduction of ethoxysilane groups in the coupling agents used results in fewer residual ethoxy groups on silicon after the article of manufacture is produced, from which fewer or no ethanol can be released by hydrolysis of the residual ethoxysilane groups by exposure of the article of manufacture to water during use.

The rubber compositions herein and the articles of manufacture derivable thereof as described herein are novel from those of the known and commonly practiced art in that both comprise hydrocarbon backbone based diols, as defined herein. Typical examples of such species in the rubber compositions and articles of manufacture described herein include diols such as an isomer of propanediol, pentane diol, and such as ethylene glycol, and propylene glycol. Additional species would include stearate monoesters and/or diesters of these diols. These species possess polarities intermediate between those of the rubber polymers and the filler, thereby helping to stabilize the compositions and articles of manufacture from filler reagglomeration and the resulting degradation of the properties and performance parameters thereof.

The invention may be better understood by reference to the following examples in which the parts and percentages are by weight unless otherwise indicated.

EXAMPLE 1

Preparation of 3-(1,2-ethanedialkoxyethoxysilyl)-1-propyl thiooctanoate from aqueous sodium hydrosulfide, octanoyl chloride, and 3-(1,2-ethanedialkoxyethoxysilyl)-1-propyl chloride A 20 weight percent aqueous solution of sodium sulfide was prepared by dissolving sodium sulfide (116 grams, 1.48 moles) in the form of hydrated flakes (193 grams, 60%) into 385 grams of water in a 5-liter round-bottomed flask. This solution was then cooled by means of an ice-water bath and converted to an aqueous solution of sodium hydrosulfide (NaSH) by saturating it with an excess of hydrogen sulfide by adding hydrogen sulfide with stirring until no more was absorbed. A dropping funnel was charged with octanoyl chloride (241 grams, 1.48 moles). With the temperature of the sodium hydrosulfide solution in the 5-liter flask at 9° C. the addition of the octanoyl chloride to the 5-liter flask was begun with stirring of the contents of the 5-liter flask with a mechanical stirrer, immediately after the addition of 1.7 grams of a 10% aqueous solution of methyltrioctylammonium chloride to the 5-liter flask. The addition of the octanoyl chloride was completed over the course of 1.8 hours with a final temperature of 13° C. The content of the 5-liter flask was kept between 8 and 19° C. during the course of the addition. The content of the 5-liter flask was then allowed to reach ambient temperature and stirring was stopped, yielding a clear, slightly viscous, one-phase aqueous solution of sodium thiooctanoate and sodium chloride.

The solution of sodium thiooctanoate was then brought to 21° C. and stirred with a mechanical stirrer throughout the rest of this procedure. To this solution was added, all at once, 3-(1,2-ethanedialkoxyethoxysilyl)-1-propyl chloride (250 grams, 1.19 moles). Immediately thereafter was added 1.4 grams of a 10% aqueous solution of methyltrioctylammonium chloride. Over the next 15 to 20 minutes, the temperature of the contents of the 5-liter flask was increased to 30° C., with continued stirring. The temperature was then ramped up to 84° C. over the next 50 minutes, and maintained for about another 20 to 21 hours with continued stirring. After cooling to ambient temperature, agitation was stopped, the two phases were allowed to separate, and the organic phase was separated from the aqueous phase.

Gas chromatography and mass spectrometry (GC and GCMS) revealed a product having 80% 3-(1,2-ethanedialkoxyethoxysilyl)-1-propyl thiooctanoate with 1% residual 3-(1,2-ethanedialkoxyethoxysilyl)-1-propyl chloride (reported purities are based on area percent GC responses). This material was then purified by flash vacuum distillation yielding a product of 83% purity.

EXAMPLE 2

Preparation of 3-(2-methyl-2,4-pentanedialkoxyethoxysilyl)-1-propyl thiooctanoate from aqueous sodium hydrosulfide, octanoyl chloride, and 3-(2-methyl-2,4-pentanedialkoxyethoxysilyl)-1-propyl chloride A 20 weight percent aqueous solution of sodium sulfide was prepared and converted to an aqueous solution of sodium thiooctanoate, by a procedure similar to the one described in Example 1. A sample of this solution of sodium thiooctanoate (854 grams, 1.46 moles) was charged into a 3-liter flask. To this solution was added 3-(2-methyl-2,4-pentanedialkoxyethoxysilyl)-1-propyl chloride (330 grams, 1.24 moles). Immediately thereafter was added 1.5 grams of a 10% aqueous solution of methyltrioctylammonium chloride. Over the next 30 minutes, the temperature of the contents of the 3-liter flask was increased to 35° C., with continued stirring. The temperature was then ramped up to 81° C. over the next 1 to 1.5 hours, and maintained at that temperature for about another 5 to 6 hours with continued stirring. After cooling to ambient temperature, agitation was stopped, the two phases were allowed to separate, and the organic phase was separated from the aqueous phase.

Gas chromatography and mass spectrometry (GC and GCMS, respectively) revealed a product having 66% 3-(2-methyl-2,4-pentanedialkoxyethoxysilyl)-1-propyl thiooctanoate with 1% 3-chloro-1-propyltriethoxysilane and 8% residual 3-(2-methyl-2,4-pentanedialkoxyethoxysilyl)-1-propyl chloride (reported purities are based on area percent GC responses). This material was then purified by flash vacuum distillation yielding a product of 81% purity.

EXAMPLE 3

Preparation of 3-(2-methyl-2,4-pentanedialkoxyethoxysilyl)-1-propyl thiooctanoate from aqueous sodium hydrosulfide, octanoyl chloride, and 3-(2-methyl-2,4-pentanedialkoxyethoxysilyl)-1-propyl chloride A 20 weight percent aqueous solution of sodium sulfide was prepared and converted to an aqueous solution of sodium thiooctanoate, by a procedure similar to the one described in Example 1. A sample of this solution of sodium thiooctanoate (1506 grams, 2.74 moles) was charged into a 3-liter flask. To this solution was added 3-(2-methyl-2,4-pentanedialkoxyethoxysilyl)-1-propyl chloride (441 grams, 1.66 moles). Immediately thereafter was added 1.6 grams of a 10% aqueous solution of methyltrioctylammonium chloride. Over the next 15 minutes, the temperature of the contents of the 3-liter flask was increased to 32° C., with continued stirring. The temperature was then ramped up to 97° C. over the next 40 minutes. The temperature was then reduced to 80° C. and maintained at that temperature for another 4 hours with continued stirring. After cooling to ambient temperature, agitation was stopped, the two phases were allowed to separate, and the organic phase was separated from the aqueous phase.

Gas chromatography and mass spectrometry revealed a product having 70% 3-(2-methyl-2,4-pentanedialkoxyethoxysilyl)-1-propyl thiooctanoate with 6% residual 3-(2-methyl-2,4-pentanedialkoxyethoxysilyl)-1-propyl chloride (reported purities are based on area percent GC responses). This material was then purified by vacuum distillation yielding a product of 97% purity.

EXAMPLE 4

Preparation of 3-(2-methyl-2,4-pentanedialkoxyethoxysilyl)-1-propyl thiooctanoate from aqueous sodium hydrosulfide, octanoyl chloride, and 3-(2-methyl-2,4-pentanedialkoxyethoxysilyl)-1-propyl chloride A nominal 20 weight percent aqueous solution of sodium sulfide was prepared by dissolving sodium sulfide (ca. 166 grams, 2.12 moles) in the form of hydrated flakes (276 grams, ca. 60%) into 552 grams of water in a 5-liter round-bottomed flask. This solution was then cooled by means of an ice-water bath and converted to an aqueous solution of sodium hydrosulfide (NaSH) by saturating it with an excess of hydrogen sulfide by adding hydrogen sulfide with stirring until no more was absorbed. A dropping funnel was charged with octanoyl chloride (345 grams, 2.12 moles). With the temperature of the sodium hydrosulfide solution in the 5-liter flask at 9.5° C. the addition of the octanoyl chloride to the 5-liter flask was begun with stirring of the contents of the 5-liter flask with a mechanical stirrer. No phase transfer catalyst was added. The addition of the octanoyl chloride was completed over the course of 2 hours with a final temperature of 14° C. The content of the 5-liter flask was kept between 8 and 12° C. during the course of the addition. A pH measurement, using pH paper, revealed that the solution was alkaline. Additional octanoyl chloride was added dropwise (totaling 15 additional grams) to the stirred solution until a neutral pH reading was obtained. The content of the 5-liter flask was then allowed to reach ambient temperature and stirring was stopped, yielding a clear, slightly viscous, one-phase aqueous solution of sodium thiooctanoate and sodium chloride.

The solution of sodium thiooctanoate was then brought to 23° C. and stirred with a mechanical stirrer throughout the rest of this procedure. To this solution was added, all at once, 3-(2-methyl-2,4-pentanedialkoxyethoxysilyl)-1-propyl chloride (451 grams, 1.69 moles). Immediately thereafter was added 1.5 grams of a 10% aqueous solution of methyltrioctylammonium chloride. Over the next 15 minutes, the temperature of the contents of the 5-liter flask was increased to 36° C. with continued stirring. The temperature was then ramped up to 83° C. over the next 40 minutes, and maintained for about another 4 hours with continued stirring. After cooling to ambient temperature, agitation was stopped, the two phases were allowed to separate, and the organic phase was separated from the aqueous phase.

Gas chromatography and mass spectrometry (GC and GCMS) revealed a product having 68% 3-(2-methyl-2,4-pentanedialkoxyethoxysilyl)-1-propyl thiooctanoate and 2.8% 3-octanoylthio-1-propyltriethoxysilane, with 8% residual 3-(2-methyl-2,4-pentanedialkoxyethoxysilyl)-1-propyl chloride (reported purities are based on area percent GC responses). This material was then purified by flash vacuum distillation yielding a product of 78% purity.

EXAMPLE 5

Preparation of 3-(2-methyl-2,4-pentanedialkoxyethoxysilyl)-1-propyl thiooctanoate from aqueous sodium hydrosulfide, octanoyl chloride, and 3-(2-methyl-2,4-pentanedialkoxyethoxysilyl)-1-propyl chloride A 20 weight percent aqueous solution of sodium sulfide was prepared by dissolving sodium sulfide (ca. 428 grams, 5.49 moles) in the form of hydrated flakes (714 grams, ca. 60%) into 1430 grams of water in a 5-liter round-bottomed flask. This solution was then cooled by means of an ice-water bath and converted to an aqueous solution of sodium hydrosulfide by saturating it with an excess of hydrogen sulfide by adding hydrogen sulfide with stirring until no more was absorbed. A portion (163 grams, 0.77 mole) of this sodium hydrosulfide solution was removed. A dropping funnel was charged with octanoyl chloride (794 grams, 4.88 moles). With the temperature of the sodium hydrosulfide solution in the 5-liter flask at 9° C., the addition of the octanoyl chloride to the 5-liter flask was begun with stirring of the contents of the 5-liter flask with a mechanical stirrer. No phase transfer catalyst was added. The addition of the octanoyl chloride was completed over the course of 6.3 hours with a final temperature of 10° C. The contents of the 5-liter flask was kept between 8 and 10° C. during the course of the addition. At this point, a pH measurement, using pH paper, revealed that the solution was alkaline. Additional octanoyl chloride was added dropwise (totaling 15 additional grams) to the stirred solution until a neutral pH reading was obtained. The contents of the 5-liter flask was then allowed to reach ambient temperature and stirring was stopped, yielding a clear, slightly viscous, one-phase aqueous solution of sodium thiooctanoate and sodium chloride.

To this solution was added 3-(2-methyl-2,4-pentanedialkoxyethoxysilyl)-1-propyl chloride (1134 grams, 4.26 moles). Immediately thereafter was added 2.4 grams of a 10% aqueous solution of methyltrioctylammonium chloride. Over the next 45 minutes, the temperature of the contents of the 5-liter flask was increased to 50° C., with continued stirring. The temperature was then ramped up to 80° C. over the next 45 minutes, and maintained for about another 3.5 hours with continued stirring. After cooling to ambient temperature, agitation was stopped, the two phases were allowed to separate, and the organic phase was separated from the aqueous phase.

Gas chromatography and mass spectrometry revealed a product having 65% 3-(2-methyl-2,4-pentanedialkoxyethoxysilyl)-1-propyl thiooctanoate and 2% 3-octanoylthio-1-propyltriethoxysilane, with 10% residual 3-(2-methyl-2,4-pentanedialkoxyethoxysilyl)-1-propyl chloride (reported purities are based on area percent GC responses). This material was then purified by removing volatiles by means of flash vacuum distillation, and subsequently pressure filtered to yield a product of 85% purity.

EXAMPLE 6

Preparation of 3-neopentanedialkoxyisopropoxysilyl)-1-propyl thiooctanoate from aqueous sodium hydrosulfide, octanoyl chloride, and 3-(neopentanedialkoxyisopropoxysilyl)-1-propyl chloride A 20 weight percent aqueous solution of sodium sulfide was prepared and converted to an aqueous solution of sodium thiooctanoate, by a procedure similar to the one described in Example 1. A sample of this solution of sodium thiooctanoate (518 grams, 0.94 moles) was charged into a 2-liter flask. To this solution was added 3-(neopentanedialkoxyisopropoxysilyl)-1-propyl chloride (200 grams, 0.75 mole). Immediately thereafter was added 1.3 grams of a 10% aqueous solution of methyltrioctylammonium chloride. Over the next 30 minutes, the temperature of the contents of the 2-liter flask was increased to 35° C. with continued stirring. The temperature was then ramped up to 82° C. over the next 60 to 90 minutes, and maintained at that temperature for another 2.5 hours with continued stirring. After cooling to ambient temperature, agitation was stopped, the two phases were allowed to separate, and the organic phase was separated from the aqueous phase.

Gas chromatography and mass spectrometry revealed a product having 53% 3-neopentanedialkoxyisopropoxysilyl)-1-propyl thiooctanoate with 1.8% of 3-chloro-1-propyltriisopropoxysilane and 8% residual 3-(neopentane dialkoxyisopropoxysilyl)-1-propylchloride (reported purities are based on area percent GC responses).

EXAMPLE 7

Preparation of 3-neopentanedialkoxyisopropoxysilyl)-1-propyl thiooctanoate from aqueous sodium hydrosulfide, octanoyl chloride, and 3-(neopentanedialkoxyisopropoxysilyl-1-propyl chloride A 20 weight percent aqueous solution of sodium sulfide was prepared and converted to an aqueous solution of sodium thiooctanoate by a procedure similar to the one described in Example 1. A sample of this solution of sodium thiooctanoate (519.5 grams, 0.94 mole) was charged into a 2-liter flask. To this solution was added 3-(neopentanedialkoxyisopropoxysilyl-1-propyl chloride (201 grams, 0.75 mole) in the form of a 50 weight percent solution (402 grams) in toluene. Immediately thereafter was added 1.5 grams of a 10% aqueous solution of methyltrioctylammonium chloride. Over the next 25 minutes, the temperature of the contents of the 2-liter flask was increased to 33° C., with continued stirring. The temperature was then ramped up to 82° C. over the next 60 minutes, and maintained at that temperature for another 3.5 hours with continued stirring. The temperature was then reduced to 63° C. and maintained for an additional 1.7 hours with continued stirring. After cooling to ambient temperature, agitation was stopped, the two phases were allowed to separate, and the organic phase was separated from the aqueous phase. Volatiles were removed by rotary evaporation to yield a slightly viscous liquid.

Gas chromatography and mass spectrometry revealed a product having 57% 3-neopentanedialkoxyisopropoxysilyl)-1-propyl thiooctanoate with 1.4% of 3-chloro-1-propyltriisopropoxysilane and 22% residual 3-(neopentanedialkoxyisopropoxysilyl-1-propyl chloride (reported purities are based on area percent GC responses). This material was then purified by flash vacuum distillation yielding a product of 64% purity.

EXAMPLE 8

Preparation of 3-(2-methyl-1,3-propanedioxyethoxysilyl)-1-propyl thiooctanoate and related oligomers from 2-methyl-1,3-propanediol and S-[3-(triethoxysilyl)propyl]thiooctanoate This example illustrates the transesterification conversion of 2 of the 3 ethoxy groups in a trialkoxy silane. A 12-liter round bottom flask equipped with a mechanical agitator, condenser (connected to a vacuum pump), dropping funnel, internal thermometer, and heating mantle, was charged with 7292 g (20.0 mol) of S-[3-(triethoxysilyl)propyl]thiooctanoate and heated to 45° C. 4.55 g Sulfuric acid was added and the mixture was stirred well. The pressure in the reaction flask was reduced to 45 mm Hg and 1802 g (20 mol) 2-methyl-1,3-propanediol were added from the dropping funnel over 4 hrs. The mixture was maintained at 44 to 45° C. and 45 mm Hg until reaction completion. Ethanol formed during the diol addition was continuously removed from the reaction flask, condensed, and collected. Sodium ethylate (11.84 g, 21% solution in ethanol) was added to the flask to neutralize the acid catalyst, and the product was cooled to room temperature. The precipitated salts were removed by filtration to yield 6956 g of product. Quantitative gas chromatography analysis showed 2.52% unreacted S-[3-(triethoxysilyl)propyl]thiooctanoate. Product gel permeation chromatography analysis showed Mn=770 and Mw=1500. No gel was found in the product.

EXAMPLE 9

Preparation of 3-(2-methyl-1,3-propanedioxyethoxysilyl)-1-propyl thiooctanoate and related oligomers from 2-methyl-1,3-propanediol and S-[3-(triethoxysilyl)propyl]thiooctanoate This example illustrates the transesterification conversion of between 2 and 3 of the ethoxy groups. A 5-liter round bottom flask equipped with a mechanical agitator, condenser (connected to a vacuum pump), dropping funnel, internal thermometer, and heating mantle, was charged with 2916 g (8.0 mol) of S-[3-(triethoxysilyl)propyl]thiooctanoate and heated to 45° C. 1.9 g Sulfuric acid was added and the mixture was stirred well. The pressure in the reaction flask was reduced to 35 mm Hg and 865.5 g (9.6 mol) 2-methyl-1,3-propanediol were added from the dropping funnel over 4 hrs. The mixture was maintained at 44 to 45° C. and 35 mm Hg until reaction completion. Ethanol (844 g) formed during the diol addition was continuously removed from the reaction flask, condensed, and collected. Sodium ethylate (4.3 g, 21% solution in ethanol) was added to the flask to neutralize the acid catalyst, and the product was cooled to room temperature. The precipitated salts were removed by filtration to yield 2800.8 g of product. Quantitative gas chromatography analysis showed 0.6% unreacted S-[3-(triethoxysilyl)propyl] thiooctanoate. Gel permeation chromatography analysis showed Mn=940 and Mw=1940. No gel was found in the product.

EXAMPLE 10

Preparation of 3-(2-methyl-1,3-propanedioxyethoxysilyl)-1-propyl thiooctanoate and related oligomers from 2-methyl-1,3-propanediol and S-[3-(triethoxysilyl)propyl]thiooctanoate This example illustrates the transesterification conversion of approximately 3 of the 3 ethoxy groups. A 5-liter round bottom flask equipped with a mechanical agitator, condenser (connected to a vacuum pump), dropping funnel, internal thermometer, and heating mantle, was charged with 2916 g (8.0 mol) of S-[3-(triethoxysilyl)propyl]thiooctanoate and heated to 45° C. 1.9 g Sulfuric acid was added and the mixture was stirred well. The pressure in the reaction flask was reduced to 34 mm Hg and 1023.7 g (11.36 mol) 2-methyl-1,3-propanediol were added from the dropping funnel over 4 hrs. The mixture was maintained at 44 to 45° C. and 8-13 mm Hg until reaction completion. Ethanol (997 g) formed during the diol addition was continuously removed from the reaction flask, condensed, and collected. Sodium ethylate (4.15 g, 21% solution in ethanol) was added to the flask to neutralize the acid catalyst, and the product was cooled to room temperature. The precipitated salts were removed by filtration to yield 2804.3 g of product. Gel permeation chromatography analysis showed $M_n$=1100 and $M_w$=2280. No gel was found in the product.

EXAMPLE 11

Preparation of 3-(1-methyl-1,3-propanedioxyethoxysilyl)-1-propyl thiooctanoate and Related Oligomers from 1,3-butanediol and S-[3-(triethoxysilyl)propyl]thiooctanoate This example illustrates the use of a hindered diol for the transesterification reaction. A 1-liter round bottom flask equipped with a mechanical agitator, condenser (connected to a vacuum pump), dropping funnel, internal thermometer, and heating mantle, was charged with 365.7 g (1.0 mol) of S-[3-(triethoxysilyl)propyl]thiooctanoate, 91.3 g (1.0 mol) 1,3-butanediol, and 0.23 g p-toluenesulfonic acid. The mixture was stirred vigorously at 45° C. and 45 mm Hg vacuum until the reaction was completed, as indicated by GC analysis. Ethanol formed during the diol addition was continuously removed from the reaction flask, condensed, and collected. Sodium carbonate (0.5 g) was added to the flask, and the reaction mixture was stirred overnight at room temperature to neutralize the acid catalyst. The precipitated salts were removed by filtration to yield 328.4 g of product. Gas chromatography analysis showed 17.5% unreacted S-[3-(triethoxysilyl)propyl]thiooctanoate and 76.9% 3-(1-Methyl-1,3-propanedioxyethoxysilyl)-1-propyl thiooctanoate. No gel was found in the product.

EXAMPLE 12

Preparation of 3-(2-methyl-2,4-pentanedioxyethoxysilyl)-1-propyl thiooctanoate and Related Oligomers from 2-methyl-2,4-pentanediol and S-[3-(triethoxysilyl)propyl]thiooctanoate This example illustrates the use of a more hindered diol for the transesterification reaction. A 2-Liter round bottom flask equipped with a mechanical agitator, condenser (connected to a vacuum pump), dropping funnel, internal thermometer, and heating mantle, was charged with 1093.8 g (3.0 mol) of S-[3-(triethoxysilyl)propyl]thiooctanoate, 354.5 g (3.0 mol) 2-methyl-2,4-pentanediol, and 0.9 g p-toluenesulfonic acid. The mixture was stirred vigorously at 40° C. and 38 to 45 mm Hg vacuum until the reaction was completed, as indicated by GC analysis. Ethanol formed during the diol addition was continuously removed from the reaction flask, condensed, and collected. Sodium carbonate (5.0 g) was added to the flask, and the reaction mixture was stirred overnight at room temperature to neutralize the acid catalyst. The precipitated salts were removed by filtration to yield 1016.8 g of product. Gas chromatography analysis showed 16.1% unreacted S-[3-(triethoxysilyl)propyl]thiooctanoate and 64.8% 3-(2-Methyl-2,4-pentanedioxyethoxysilyl)-1-propyl thiooctanoate. No gel was found in the product.

EXAMPLE 13

Preparation of 3-(1,2-ethanedioxyethoxysilyl)-1-propyl thiooctanoate and Related Oligomers from 1,2-ethyleneglycol and S-[3-(triethoxysilyl)propyl]thiooctanoate This example illustrates the use of a 1,2 diol with no steric hindrance for the transesterification reaction. A 2-liter round bottom flask equipped with a mechanical agitator, condenser (connected to a vacuum pump), dropping funnel, internal thermometer, and heating mantle, was charged with 1093.8 g (3.0 mol) of S-[3-(triethoxysilyl)propyl]thiooctanoate, 167.6 g (2.7 mol) 1,2-ethyleneglycol, and 0.5 g p-toluenesulfonic acid. The mixture was stirred vigorously at 42° C. and 31 mm Hg vacuum until the reaction was completed, as indicated by GC analysis. Ethanol formed during the diol addition was continuously removed from the reaction flask, condensed, and collected. Sodium carbonate (6.0 g) was added to the flask, and the reaction mixture was stirred overnight at room temperature to neutralize the acid catalyst. The precipitated salts were removed by filtration to yield 1002.2 g of product. No gel was found in the product.

EXAMPLE 14

Preparation of 3-(2-methyl-1,3-propanedioxyethoxysilyl)-1-propyl thiooctanoate and Related Oligomers from 2-methyl-1,3-propanediol and S-[3-(triethoxysilyl)propyl]thiooctanoate, in a wiped film reactor This example illustrates a continuous transesterification process for producing the composition of this invention. The wiped film reactor consisted of a vertically positioned glass tube, 5.1 cm inside diameter and 38 cm length, fitted with a water-cooled internal condenser, 15 cm length. Three rotating teflon wiper blades, 20 cm in length, were positioned 10 cm below the top of the reactor and coupled to a variable speed control with forward and reverse rotation option. The wiper blades were held against the inner walls of the reactor by centrifugal action. The reactor temperature was controlled by means of two electrical heating jackets, wrapped around the outside walls of the reactor. Thermocouples for temperature measurement were placed in the space between the outer wall of the reactor and the heating mantle. The top of the reactor was connected to a dry ice condenser fitted with a collection flask, a pressure gauge and a vacuum pump. The reactor feed system consisted of two liquid metering piston pumps which co-fed S-[3-(triethoxysilyl)propyl]thiooctanoate and sulfuric acid having 2-methyl-1,3-propanol respectively to an in-line static mixer (22 cm length, 0.64 cm inner diameter). The reactant mixture was discharged into the reactor through a port situated 2.5 cm above the wiper blades. During the run, ethanol vapor produced was condensed in the dry ice condenser and collected. Non-evaporated product mixture (bottom product) and vapor mixture condensed on the internal condenser were removed continuously out of the system at a rate equal to the feed rate. To conduct the run, the heating jacket was heated to 120° C., the reactor pressure was reduced to 11 mm Hg, and S-[3-(triethoxysilyl)propyl]thiooctanoate (10.0 g/min, 27.4 mmol) and sulfuric acid having 2-methyl-1,3-propanol (2.7 g diol/min, 30.0 mmol diol, 0.003 g/min $H_2SO_4$) were continuously fed to the system. At the end of one hour, product mixture (719.5 g), vapor mixture (20.0 gr), and ethanol lights (60.2 gr) were collected and analyzed. Gas chromatography analysis of the product mixture showed 9.7% ethanol, 1.9% unreacted 2-methyl-1,3-propanediol, 9.6% unreacted S-[3-(triethoxysilyl)propyl]thiooctanoate, 46.54% 3-(1-methyl-1,3-propanedioxyethoxysilyl)-1-propyl thiooctanoate monomer, with the remaining to 100% consisting of related oligomers and siloxanes of 3-(1-methyl-1,3-propanedioxyethoxysilyl)-1-propyl thiooctanoate.

EXAMPLES 15, 16 and 17

Preparation of Rubber 3-(2-methyl-2,4-pentanedialkoxyethoxysilyl)-1-propyl thiooctanoate In this section, examples are presented that identify the performance differences between polysulfide silanes (e.g. TESPD), 3-octanoylthio-1-propyltriethoxysilanesilane (OPTES), and the cyclic dialkoxy thiocarboxylate silane, 3-(2-methyl-2,4-pentanedialkoxyethoxysilyl)-1-propyl thiooctanoate (MPESO) silane.

A typical silica-rubber SBR formulation was used (Table 1). Mixing was carried out in a 1.6 liter "B" type Banbury with tangential rotors. Silquest®A-1289 (TESPT, bis-(3-triethoxysilyl-1-propyl) tetrasulfide, sold by General Electric Corporation) and Silquest®A-1589 (TESPD, bis-(triethoxysilylpropyl) disulfide, sold by General Electric Corporation) were chosen as controls. The silane loadings were adjusted to a constant alkoxysilane silicon loading.

TABLE 1

Silica-Silane/Rubber Formulation

| PHR | Ingredient |
|---|---|
| 103.2 | SSBR (Buna VSL 5525-1, Bayer AG) |
| 25 | BR (Budene 1207, Goodyear) |
| variable | silica (Zeosil 1165MP, Rhodia) |
| variable | A-1589 |
| variable | 3-octanoylthio-1-propyltriethoxysilane-(OPTES) |
| variable | 3-(2-methyl-2,4-pentanedialkoxyethoxysilyl)-1-propyl thiooctanoate (MPESO) |
| 5.0 | oil (Sundex 8125, Sun Oil) |

TABLE 1-continued

Silica-Silane/Rubber Formulation

| PHR | Ingredient |
|---|---|
| 2.5 | zinc oxide (Kadox 720C, ZincCorp.) |
| 1.0 | stearic acid (Industrene R, Witco, Crompton) |
| 2.0 | 6 PPD (Flexzone 7P, Uniroyal, Crompton) |
| 1.5 | Wax (Sunproof Improved, Uniroyal, Crompton) |
| Variable | Hardness modifiers (carbon-black, fumed silica and accelerators) |
|  | Final Mix Ingredients |
| 1.4 | Sulfur (#104, Harwick) |
| 1.7 | CBS accelerator (Delac S. Uniroyal, Crompton) |
| 2.0 | DPG accelerator (Uniroyal, Crompton) |

TABLE 2

Procedure for Two- and One-Non productive mix steps
TWO PASS PROCEDURE

| Step | Procedure |
|---|---|
|  | First Banbury pass: cooling with water @ 25° C., 72% fill factor |
| 1. | Add polymers, RDM (ram down mix) 30 seconds @ 117 RPM |
| 2. | Add 50% silica, all silane, RDM 30 seconds |
| 3. | Add remaining 50% silica, oil, RDM 30 seconds |
| 4. | Dust down, RDM 20 seconds |
| 5. | Dust down, RDM 20 seconds |
| 6. | Dust down, RDM @ higher speeds to 160-170° C. (approx. 1 minute). Total time for first pass is approx. 5-6 minutes. |
| 7. | Dump, sheet off roll mill @ 50-60° C., cool below 60° C. |
|  | Second Banbury pass: |
| 1. | Add compound from 1st pass, RDM 30 seconds @ 117 RPM |
| 2. | Add remainder of ingredients, RDM 30 seconds |
| 3. | Dust down, RDM to 160-170° C. (in approx. 2 minutes) by increasing rotor speed. |
| 4. | Hold at 170° C. (or higher temperature) for 8 minutes by changing speeds on mixer. Total time for second Banbury pass is approx. 11-12 minutes. |
| 5. | Dump, sheet off roll mill @ 50-60° C. to cool |

* RDM: Ram down mix time.

Single Pass Procedure

Combine first and second pass of two-pass mix sequence by going to step 2 of second pass immediately after completing step 4 of first pass, which eliminates the intermediate cooling step.

Productive Mix

Add sulfur and accelerators (primary and secondary) into the above masterbatch on a two-roll mill at 50-60° C. The controls, Silquest®A-1289 (TESPT) and Silquest®A-1589 (TESPD), were mixed in two non-productive mix steps, which included an intermediate cooling step. The 3-octanoylthio-1-propyltriethoxysilane and MPESO silane-comprising compounds were mixed in one non-productive mix step, without any intermediate cooling step. After all silica, silane and oil are incorporated into the mix, the rpm of the rotors is raised so as to achieve the desired silanization temperature. The mix is then held at that temperature for 8 minutes. For polysulfide silanes, a cooling step is needed before this silanization step (sometimes even multiple cooling steps). 3-Octanoylthio-1-propyltriethoxysilane and MPESO silane eliminate this need. The mix procedures are shown in Table 2, above. Curing and testing were done according to ASTM standards. In addition, small strain dynamic tests were carried out on a Rheometrics Dynamic Analyzer (ARES—Rheometrics Inc.).

| Measurement/Procedure | Compound Testing Standards |
|---|---|
| Mooney viscosity and scorch | ASTM D1646 |
| Oscillating disc rheometry | ASTM D2084 |
| Curing of test plaques | ASTM D3182 |
| Stress-strain properties | ASTM D412 |
| Heat build-up | ASTM D623 |

Dynamic Mechanical Properties

Payne effect strain sweeps were carried out from dynamic strain amplitudes of 0.01% to about 25% shear strain amplitude at 10 Hz and 60° C. The dynamic parameters, $G'_{initial}$, $\Delta G'$, $G''_{max}$, $\tan \delta_{max}$ were extracted from the non-linear responses of the rubber compounds at small strains. In some cases, steady state values of tan δ were measured after 15 minutes of dynamic oscillations at strain amplitudes of 35% (at 60° C.). Temperature dependence of dynamic properties were also measured from about −80° C. to +80° C. at small strain amplitudes (1 or 2%) at a frequency of 10 Hz.

As observed from Example 15, the OPTES silane compound exhibits lower Mooney viscosity, and decreased non-linearity (lower G', ΔG' and tan $\delta_{max}$) compared to TESPD (di-sulfide silane). This is an indication of improved silica dispersion and lower hysteresis at 60° C. The OPTES silane compound also shows superior tensile properties compared to the control TESPD, with a fast rate of growth of its high strain moduli. The reinforcing index as measured by M300/M100 is higher than TESPD. The cyclic dialkoxy thiocarboxylate silane (MPESO) was tested at three loading levels (7.7, 8.2, and 9.0 phr respectively). The compounds using MPESO show similar processing and performance features as OPTES silane compound. The overall efficiency of MPESO is slightly inferior than OPTES silane in these rubber compounds. This can be inferred from the higher Mooney viscosities and tan $\delta_{max}$, hardness and lower moduli and reinforcement indices obtained with compounds using MPESO silane. The loading level of 8.2 phr for MPESO (at equal rate with OPTES silane) is sufficient to maximize all processing and performance attributes of the rubber compound. Examples 16 and 17 show simple modifications to the mixing procedures and addition of certain ingredients used to improve the MPESO compound properties up to the levels of OPTES silane compounds.

Example 16 demonstrates the use of higher mixing times or higher mixing temperatures (more specifically higher silanization temperatures) to enhance the reaction of MPESO silane with silica—and lead to an overall property set closer to OPTES silane compound. From the data, it is clearly evident that, upon increasing the mixing time of MPESO (from 8 minutes to 12 minutes) or increasing the mixing temperature from (170° C. to 180° C.), the hysteresis at 60° C. and reinforcing power of MPESO compounds improve and become essentially equivalent to the compounds using OPTES silane.

Another method of improving the processing and performance characteristics of MPESO silane was demonstrated in Example 17. In this example, certain hydrolysis catalysts that promote the reaction of MPESO with precipitated silica (viz. diethylene glycol and diethanolamine) were used to enhance the end properties resulting from MPESO rubber compounds. From the table in Example 17, it was observed that addition of small amounts of DEG or diethanolamine (base catalyst) substantially improved the reinforcing index and moduli growth rate of the MPESO compounds. The overall processing and performance behavior of MPESO compounds with DEG or diethanolamine was equivalent to the OPTES silane compound.

EXAMPLE 15

Comparison of TESPD, OPTES and MPESO Silane Compounds

| | TESPD | OPTES | MPESO Lower Loading | MPESO Equal loading | MPESO Higher Loading |
|---|---|---|---|---|---|
| Ingredient (phr) | | | | | |
| solution SBR | 103.2 | 103.2 | 103.2 | 103.2 | 103.2 |
| Butadiene rubber | 25.0 | 25.0 | 25.0 | 25.0 | 25.0 |
| Silica | 80 | 80 | 80 | 80 | 80 |
| TESPD | 6.2 | | | | |
| OPTES | | 8.2 | | | |
| MPESO | | | 7.7 | 8.2 | 9.0 |
| No. of Mixing steps | 2 | 1 | 1 | 1 | 1 |
| Mixing temperature | 160° C. | 170° C. | 170° C. | 170° C. | 170° C. |
| Silanization time (min) | 8 | 8 | 8 | 8 | 8 |
| Compound properties | | | | | |
| Processing | | | | | |
| Mooney Viscosity | 72 | 64 | 69 | 69 | 67 |
| Scorch time (min) | 10.1 | 11.2 | 10.5 | 9.3 | 8.5 |
| Cure time t90 (min) | 14.4 | 15.0 | 14.5 | 13.2 | 12.3 |
| $M_L$ (dNm) | 8.8 | 7.6 | 7.9 | 7.9 | 7.7 |
| $M_H$ (dNm) | 27.9 | 26.2 | 26.2 | 26.4 | 26.4 |
| Properties in the cured state | | | | | |
| Non-linearity (0-10%) @ 60° C. | | | | | |
| $G'_{initial}$ (MPa) | 4.47 | 3.43 | 3.47 | 3.15 | 3.49 |
| $\Delta G'$ (MPa) | 2.68 | 1.82 | 1.89 | 1.77 | 1.92 |
| $G''_{max}$ (MPa) | 0.53 | 0.37 | 0.38 | 0.35 | 0.37 |
| $\tan \delta_{max}$ | 0.21 | 0.15 | 0.17 | 0.17 | 0.16 |

-continued

|  | TESPD | OPTES | MPESO Lower Loading | MPESO Equal loading | MPESO Higher Loading |
|---|---|---|---|---|---|
| Wet-Skid Indicator, 10 Hz, 1% DSA | | | | | |
| tan δ|0° C. | 0.400 | 0.373 | 0.380 | 0.373 | 0.391 |
| Reinforcement | | | | | |
| Hardness (Shore A) | 58.0 | 54.0 | 55.0 | 55.0 | 56.0 |
| M 25% (MPa) | 0.89 | 0.78 | 0.84 | 0.82 | 0.82 |
| M 100% (MPa) | 1.73 | 1.73 | 1.73 | 1.8 | 1.78 |
| M 300% (MPa) | 8.65 | 9.55 | 8.33 | 8.57 | 8.54 |
| M 300%/M100% | 5.0 | 5.5 | 4.8 | 4.8 | 4.8 |
| Elongation at rupture (%) | 564.0 | 530.0 | 531.0 | 577.0 | 581.0 |
| Stress at rupture (MPa) | 23.1 | 23.2 | 19.9 | 22.7 | 22.0 |

EXAMPLE 16

Processing and Performance Behavior of MPESO Compounds Mixed at Higher Mixing Times or at Higher Mixing Temperatures

|  | TESPD | OPTES | MPESO Higher Mixing time | MPESO Higher Mixing temp. |
|---|---|---|---|---|
| Ingredient (phr) | | | | |
| solution SBR | 103.2 | 103.2 | 103.2 | 103.2 |
| Butadiene rubber | 25.0 | 25.0 | 25.0 | 25.0 |
| Silica | 80 | 80 | 80 | 80 |
| TESPD | 6.2 | | | |
| OPTES | | 8.2 | | |
| MPESO | | | 7.7 | 8.2 |
| No. of Mixing steps | 2 | 1 | 1 | 1 |
| Mixing temperature | 160° C. | 170° C. | 170° C. | 180° C. |
| Silanization time (min) | 8 | 8 | 12 | 8 |
| Compound properties | | | | |
| Processing | | | | |
| Mooney Viscosity | 72 | 64 | 65 | 69 |
| Scorch time (min) | 10.1 | 11.2 | 10.4 | 9.1 |
| Cure time t90 (min) | 14.4 | 15.0 | 13.5 | 13.3 |
| $M_L$ (dNm) | 8.8 | 7.6 | 7.7 | 8.0 |
| $M_H$ (dNm) | 27.9 | 26.2 | 25.6 | 26.0 |
| Properties in the cured state | | | | |
| Non-linearity (0-10%) @ 60° C. | | | | |
| $G'_{initial}$ (MPa) | 4.47 | 3.43 | 3.08 | 3.01 |
| ΔG' (MPa) | 2.68 | 1.82 | 1.49 | 1.47 |
| $G''_{max}$ (MPa) | 0.53 | 0.37 | 0.34 | 0.32 |
| $tanδ_{max}$ | 0.21 | 0.15 | 0.15 | 0.16 |
| Wet-Skid Indicator, 10 Hz, 1% DSA | | | | |
| tan δ|0° C. | 0.400 | 0.373 | 0.413 | 0.410 |
| Reinforcement | | | | |
| Hardness (Shore A) | 58.0 | 54.0 | 54.0 | 56.0 |
| M 25% (MPa) | 0.89 | 0.78 | 0.8 | 0.8 |
| M 100% (MPa) | 1.73 | 1.73 | 1.74 | 1.85 |
| M 300% (MPa) | 8.65 | 9.55 | 9.02 | 9.34 |
| M 300%/M100% | 5.0 | 5.5 | 5.2 | 5.0 |
| Elongation at rupture (%) | 564.0 | 530.0 | 533.0 | 550.0 |
| Stress at rupture (MPa) | 23.1 | 23.2 | 21.4 | 22.1 |

EXAMPLE 17

Processing and Performance Behavior of MPESO Compounds Using Diethylene Glycol

|  | TESPD | OPTES | MPESO with glycol | MPESO with base catalyst |
| --- | --- | --- | --- | --- |
| Ingredient (phr) |  |  |  |  |
| solution SBR | 103.2 | 103.2 | 103.2 | 103.2 |
| Butadiene rubber | 25.0 | 25.0 | 25.0 | 25.0 |
| Silica | 80 | 80 | 80 | 80 |
| TESPD | 6.2 |  |  |  |
| OPTES |  | 8.2 |  |  |
| MPESO |  |  | 7.7 | 8.2 |
| DEG |  |  | 1.0 |  |
| Diethanolamine |  |  |  | 0.5 |
| No. of Mixing steps | 2 | 1 | 1 | 1 |
| Mixing temperature | 160° C. | 170° C. | 170° C. | 170° C. |
| Silanization time (min) | 8 | 8 | 8 | 8 |
| Compound properties |  |  |  |  |
| Processing |  |  |  |  |
| Mooney Viscosity | 72 | 64 | 67 | 66 |
| Scorch time (min) | 10.1 | 11.2 | 9.3 | 7.0 |
| Cure time t90 (min) | 14.4 | 15.0 | 12.4 | 11.5 |
| $M_L$ (dNm) | 8.8 | 7.6 | 7.7 | 8.1 |
| $M_H$ (dNm) | 27.9 | 26.2 | 26.9 | 26.4 |
| Properties in the cured state |  |  |  |  |
| Non-linearity (0-10%) @ 60° C. |  |  |  |  |
| $G'_{initial}$ (MPa) | 4.47 | 3.43 | 3.96 | 2.84 |
| $\Delta G'$ (MPa) | 2.68 | 1.82 | 2.20 | 1.33 |
| $G''_{max}$ (MPa) | 0.53 | 0.37 | 0.42 | 0.30 |
| $\tan\delta_{max}$ | 0.21 | 0.15 | 0.17 | 0.16 |
| Wet-Skid Indicator, 10 Hz, 1% DSA |  |  |  |  |
| $\tan\delta|0°$ C. | 0.400 | 0.373 | 0.377 | 0.380 |
| Reinforcement |  |  |  |  |
| Hardness (Shore A) | 58.0 | 54.0 | 57.0 | 55.0 |
| M 25% (MPa) | 0.89 | 0.78 | 0.81 | 0.81 |
| M 100% (MPa) | 1.73 | 1.73 | 1.83 | 1.87 |
| M 300% (MPa) | 8.65 | 9.55 | 9.25 | 10.34 |
| M 300%/M100% | 5.0 | 5.5 | 5.1 | 5.5 |
| Elongation at rupture (%) | 564.0 | 530.0 | 557.0 | 517.0 |
| Stress at rupture (MPa) | 23.1 | 23.2 | 22.5 | 23.3 |

EXAMPLE 18

VOC Measurements from the Banbury Mixer

The mixing recipe for VOC measurements included all ingredients used in the non-productive mix steps. Mixing was carried out as indicated in Table 2, until Step 6 of the first non-productive mix step. At this point the speed (rpm) of the mixer was raised so as to attain a temperature of 160° C., and the mix was held at that temperature for more than 40 minutes. The mixing times were purposely pushed for long times at 160° C. to get the maximum volatile generation possible.

Exhaust vapors were sampled for VOC analysis during compounding in the Banbury mixer. Three silanes, TESPT, OPTES, and MPESO were evaluated. A sampling rate of 320 cc/minute was used. Isopropanol was injected into the exhaust stream at a given rate to calibrate the experiment, i.e., to establish an exact known ratio of sampling stream to total exhaust. Exhaust gases were adsorbed on activated charcoal by passing the exhaust sample through a column of the activated charcoal. The charcoal was subsequently desorbed by saturating the charcoal with carbon disulfide, which quantitatively displaced the adsorbed exhaust gases. Results obtained are based on hydrolysis of all alkoxy groups to ethanol. Assumptions were 6 moles of ethanol released per mole of TESPT, 3 for OPTES, and 1 for MPESO. The results obtained from VOC measurements are tabulated below. Based on these results, a substantial reduction in VOC emissions can be achieved by using OPTES and MPESO silanes. Under standard mixing conditions, the MPESO may be expected to provide even larger reductions in VOC emissions.

EXAMPLE 18

VOC Measurements from the Banbury Mixer

| Silane | Silane phr Loading Silica: 80 phr | EtOH evolved (Kg) per Kg of silane (Maximum) All ethoxy's react | Gms. EtOH evolved per Kg of Rubber (Actual) | % VOC reduction w.r.t. TESPT |
|---|---|---|---|---|
| TESPT | 6.2 | 0.582 | 13.9 | 0 |
| OPTES | 8.2 | 0.379 | 11.93 | 14 |
| MPESO | 8.2 | 0.117 | 5.92 | 57 |
| OPTES | 6.2 | 0.379 | 9.02 | 35 |
| MPESO | 6.2 | 0.117 | 4.47 | 68 |

Although the invention has been described in its embodiments with a certain degree of particularity, obviously many changes and variations are possible therein and will be apparent to those skilled in the art after reading the foregoing description. It is therefore to be understood that the present invention may be presented otherwise than as specifically described herein without departing from the spirit and scope thereof.

EXAMPLE 19

Preparation of 3-(2-methyl-1,3-propanedialkoxymethylsilyl)-1-propyl thiooctanoate and related oligomers from 2-methyl-1,3-propanediol and 3-thiooctanoyl-1-propyldiethoxymethylsilane Into a 100 ml, 3-neck round bottom flask equipped with a magnetic stirrer, thermocouple and temperature controller, distillation head and cold finger were charged water (13.55 grams), sodium hydrogen sulfide (45 percent in water, 16.85 grams, 0.1354 moles) and tetrabutylammonium bromide (50 percent in water, 0.01 grams, 0.015 mmoles). The octanoyl chloride (10 grams, 0.0615 moles) was added at room temperature over a period of 16 minutes. During the addition, the temperature rose to 38.2° C. The mixture was stirred for an additional 30 minutes and allowed to cool to room temperature. Tetrabutyl ammonium bromide (0.76 grams 0.0185 moles) and 3-chloropropylmethyldiethoxysilane (12.95 grams, 0.06154 moles) were added and then the mixture was heated at 80° C. for 6 hours. The mixture was cooled to room temperature and the organic phase was separated for the aqueous phase using a 250 ml separatory funnel. The organic phase was stripped under reduced pressure and nitrogen sparge at 140° C. The reaction was repeated to produce more 3-thiooctanoyl-1-propyldiethoxymethylsilane. Gas phase analysis indicated that the intermediate was 90.1 percent pure.

Into a 500 ml round bottom flask equipped with a mechanical agitator, condenser (connected to a vacuum pump), dropping funnel, internal thermometer, nitrogen sparge and heating mantle were charged 3-thiooctanoyl-1-propyldiethoxymethylsilane (167.3 grams, 0.5 moles) and sulfuric acid (0.106 gram). The mixture was heated to 45° C. under reduced pressure and then the 2-methyl-1,3-propanediol (45.1 grams, 0.5 moles) was added dropwise over a 30 minute period. After the addition was completed, the mixture was stripped under reduce pressure for 30 minutes and then the pH of the mixture was adjusted to pH=5.5 using sodium ethoxide in ethanol (21% sodium ethoxide in ethanol, 0.36 grams). Gas phase analysis of the mixture found 8.3 percent 2-methyl-1,3-propanediol, 1.1 percent 3-thiooctanoyl-1-propyldiethoxymethylsilane and 53.3 percent 3-(2-methyl-1,3-propanedialkoxymethylsilyl)-1-propyl thiooctanoate. The bridge diol silane components did not elute from the gas chromatographic column.

EXAMPLE 20

Preparation of 3-(1,3-Butanedialkoxymethylsilyl)-1-propyl thiooctanoate and Related Oligomers from 1,3-butanediol and 3-thiooctanoyl-1-propyldiethoxymethylsilane The 3-(1,3-butanedialkoxymethylsilyl)-1-propyl thiooctanoate was prepared according to the procedure similar to Example 19, except that 1,3-butanediol was substituted for the 2-methyl-1,3-propanediol.

EXAMPLE 21

Preparation of Rubber Using 3-(2-methyl-1,3-propanedialkoxymethylsilyl)-1-propyl thiooctanoate (MPDMS) and 3-(1,3-butanedialkoxymethylsilane)-1-propyl thiooctanoate (BDMS)

In this section, examples are presented that identify the performance differences between bis-(3-triethoxysilylpropyl) disulfide (TESPD), 3-thiooctanoyl-1-propyltriethoxysilane (OPTES) and 3-(2-methyl-1,3-propanedialkoxymethylsilyl)-1-propyl thiooctanoate when used in rubber compounds. A typical silica-rubber SBR formulation given in Table 1 was used. The silane loadings were adjusted to achieve equivalent silicon loading. The rubber compounds were prepared and tested using according to the procedure similar to the one described in Example 15. The results are present in table below.

Processing and Performance Behavior of 3-(2-methyl-1,3-propanedialkoxymethylsilyl)-1-propyl thiooctanoate (MPDMS) and 3-(1,3-butanedialkoxymethylsilane)-1-propyl thiooctanoate (BDMS)

| | TESPD | OPTES | MPDMS | BDMS |
|---|---|---|---|---|
| Ingredient (phr) | | | | |
| Solution SBR | 103.2 | 103.2 | 103.2 | 103.2 |
| Butadiene rubber | 25 | 25 | 75 | 25 |
| silica | 80 | 80 | 80 | 80 |
| TESPD | 6.2 | | | |

-continued

|  | TESPD | OPTES | MPDMS | BDMS |
|---|---|---|---|---|
| OPTES |  | 8.2 |  |  |
| MPDMS |  |  | 7.5 |  |
| BDMS |  |  |  | 7.5 |
| No. of mixing steps | 2 | 1 | 1 | 1 |
| Mixing temperature | 160° C. | 170° C. | 170° C. | 170° C. |
| Silanization time (min) | 8 | 8 | 8 | 8 |
| Compound Properties |  |  |  |  |
| Processing |  |  |  |  |
| Mooney Viscosity at 100° C. (ML1 + 4) | 71.5 | 61.6 | 61.6 | 63.7 |
| Scorch at 135° C. (MS1 + $t_3$) (min) | 10.2 | 11.1 | 10.1 | 10.3 |
| Cure time 't90 (min) | 16.2 | 14.4 | 11.0 | 11.3 |
| $M_L$ (dN-m) | 9.8 | 7.9 | 8.4 | 8.6 |
| $M_H$ (dN-m) | 30.1 | 26.9 | 29.9 | 30.6 |
| Properties in the cured state |  |  |  |  |
| Non-linearity (0-10%) 60° C. |  |  |  |  |
| $G'_{initial}$ (MPa) | 4.16 | 3.12 | 3.50 | 3.28 |
| $\Delta G'$ (MPa) | 2.57 | 1.59 | 1.81 | 1.72 |
| $G''_{max}$ (MPa) | 0.528 | 0.414 | 0.393 | 0.364 |
| $\tan\delta_{max}$ | 0.195 | 0.156 | 0.137 | 0.136 |
| Wet-Skid Indicator, 10 Hz, 1% DSA |  |  |  |  |
| $\tan\delta$ 0° C. | 0.422 | 0.411 | 0.481 | 0.484 |
| Reinforcement |  |  |  |  |
| Hardness (Shore A) | 62 | 56 | 60 | 61 |
| 25% Modulus (MPa) | 0.939 | 0.795 | 0.895 | 0.914 |
| 100% Modulus (MPa) | 2.02 | 1.86 | 2.37 | 2.45 |
| 300% Modulus (MPa) | 10.81 | 10.13 | 12.80 | 12.72 |
| Reinforcement Index, (300%/25%) | 11.51 | 12.74 | 14.30 | 13.92 |
| Reinforcement Index, (300%/100%) | 5.35 | 5.45 | 5.40 | 5.19 |
| Elongation at rupture (%) | 513 | 541 | 501 | 493 |
| Stress at rupture (MPa) | 23.90 | 23.03 | 24.17 | 23.27 |

What is claimed is:

1. A process for the preparation of a cyclic and bridging dialkoxy silane composition comprising at least one component having a chemical structure selected from the group consisting of:

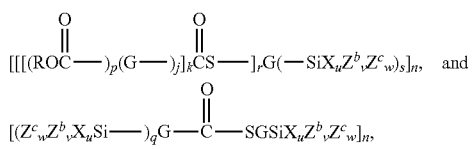

wherein:
each occurrence of the —$SiX_uZ^b_vZ^c_w$ group is independently selected from the group consisting of —$SiXZ^c$, —$SiZ^bZ^c$, —$SiX_2Z^b$, —$SiXZ^b_2$ and —$SiZ^b_3$;

each occurrence of R is independently selected from the group consisting of hydrogen, straight, cyclic or branched alkyl group, alkenyl group, aryl group, and aralkyl group, with each R, other than hydrogen, containing from 1 to 18 carbon atoms;

each occurrence of G is independently selected from the group consisting of hydrogen, a monovalent alkyl, alkenyl, aryl or aralkyl group containing from 1 to 30 carbon atoms, and polyvalent group containing from 1 to 30 carbon atoms derived from an alkyl, alkenyl, aryl or aralkyl group;

each occurrence of X is independently selected from the group consisting of —Cl, —Br, $R^1O$—, $R^1O(R^4CR^5)_fO$—, $R^1C(=O)O$—, $R^1R^2C=NO$—, $R^1R^2NO$—, $R^1R^2N$—, —$R^1$, and —$(OSi\ R^1R^2)_t(OSi\ R^1R^2R^3)$, wherein each occurrence of $R^1$, $R^2$ and $R^3$ is independently R;

each occurrence of $Z^b$, which forms a bridging structure between two different silicon atoms, is independently selected from the group consisting of (—O—)$_{0.5}$ and [—$O(R^4CR^5)_fO$—]$_{0.5}$, wherein each occurrence of $R^4$ and $R^5$ is independently R;

each occurrence of $Z^c$, which forms a cyclic structure with a single silicon atom, is independently given by —$O(R^4CR^5)_fO$— wherein each occurrence of $R^4$ and $R^5$ is independently R;

each occurrence of the subscripts, u, n, v, w, f, p, r, q, j, t, and s, and k, is independently given by u is 0 to 3; n is 1 to 100, with the proviso that when n is greater than 1, v is greater than 0 and all the valences for $Z^b$ have a silicon atom bonded to them; v is 0 to 3; w is 0 to 1 with the proviso that u+v+2w is 3; f is 1 to 15; p is 0 to 5; r is 1 to 3; q is 0 to 6; j is 0 to 1, with the proviso that when j is 0 p is 1; t is 0 to 50; s is 1 to 3; and k is 1 and wherein that each of the above structures comprise at least two hydrolysable bridging dialkoxy group, $Z^b$, or at least one hydrolysable cyclic dialkoxy group, $Z^c$, the process comprising reacting an aqueous solution of a salt of at least one thioacid with at least one cyclic and bridging dialkoxy haloalkyl silane and, optionally, at least one haloalkyl silane to provide cyclic and bridging dialkoxy silane composition.

2. The process of claim 1, wherein the cyclic and bridging dialkoxy haloalkyl silane is:

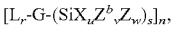

and the structure for the thiocarboxylate salt is selected from the group consisting of the formula:

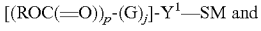

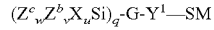

wherein
each occurrence of M is independently selected from alkali metal; ammonium; and mono-, di-, or tri- substituted ammonium;

each occurrence of $Y^1$ is carbonyl;

each occurrence of R is independently selected from the group consisting of hydrogen, straight, cyclic or branched alkyl group, alkenyl group, aryl group, and aralkyl group, with each R, other than hydrogen, containing from 1 to 18 carbon atoms;

each occurrence of G is independently selected from the group consisting of hydrogen, monovalent alkyl, alkenyl, aryl or aralkyl group containing from 1 to 30 carbon atoms, and polyvalent group containing from 1 to 30 carbon atoms derived from alkyl, alkenyl, aryl or aralkyl group;

each occurrence of X is independently selected from the group consisting of —Cl, —Br, $R^1O$—, $R^1O(R^4CR^5)_f$ O—, $R^1C(=O)O$—, $R^1R^2C=NO$—, $R^1R^2NO$—, $R^1R^2N$—, —$R^1$, and —$(OSi\ R^1R^2)_t(OSi\ R^1R^2R^3)$, wherein each occurrence of $R^1$, $R^2$ and $R^3$ is independently R;

each occurrence of $Z^b$, which forms a bridging structure between two different silicon atoms, is independently selected from the group consisting of (—O—)$_{0.5}$ and [—$O(R^4CR^5)_fO$—]$_{0.5}$, wherein each occurrence of $R^4$ and $R^5$ is independently R;

each occurrence of $Z^c$, which forms a cyclic structure with a single silicon atom, is independently given by —$O(R^4CR^5)_fO$— wherein each occurrence of $R^4$ and $R^5$ is independently R;

each occurrence of L is independently chloro or bromo, and each occurrence of the subscripts, f, j, n, p, q, u, v, w, r, t, and s is independently given by f is 1 to 15; j is 0 to 1, with the proviso that when j is 0 p is 1; n is 1 to 100, with the proviso that when n is greater than 1, v is greater than 0 and all the valences for $Z^b$ have a silicon atom bonded to them; p is 0 to 5; q is 0 to 6; u is 0 to 3; v is 0 to 3; w is 0 to 1 with the proviso that u+v+2w is 3; r is 1 to 3; t is 0 to 50, and s is 1 to 3 and wherein the structure, $[L_r\text{-}G\text{-}(SiX_uZ^b{}_vZ_w)_s]_n$, comprises at least two hydrolysable bridging dialkoxy groups, $Z^b$, or at least one hydrolysable cyclic dialkoxy group, $Z^c$.

3. The process of claim 1, wherein the reaction temperature is about 40 to about 85° C. and the pressure is ambient.

4. The process of claim 1, wherein the reaction is carried out in the presence of at least one phase transfer catalyst of the formula:

$$(R^6R^7R^8R^9N^+)_mA^{-m}$$

wherein each occurrence of $R^6$, $R^7$, $R^8$ and $R^9$ is independently R, where R is selected from the group consisting of hydrogen, straight, cyclic or branched alkyl group-alkenyl group, aryl group, and aralkyl group, with each R, other than hydrogen, containing from 1 to 18 carbon atoms; N is nitrogen; $A^{-m}$ is a monovalent or polyvalent anion selected from the group consisting of fluoride, chloride, bromide, iodide, sulfate, bisulfate, carbonate, bicarbonate, hydroxide, phosphate, carbox late and h drosulfide, where the minus sign denotes that the species is an anion, and m denotes the number of negative charges on the anion; and the subscript m is a positive integer of from 1 to 6.

5. The process of claim 4, wherein the phase transfer catalyst is selected from the group consisting of tetramethylammonium chloride, tetramethylammonium bromide, tetramethylammonium iodide, tetramethylammonium hydroxide, tetraethylammonium chloride, tetraethylammonium bromide, tetraethylammonium iodide, tetraethylammonium hydroxide, tetrabutylammonium chloride, tetrabutylammonium bromide, tetrabutylammonium iodide, tetrabutylammonium hydroxide, methyltributylammonium chloride, methyltributylammonium bromide, methyltributylammonium iodide, methyltributylammonium hydroxide, tetraoctyl ammonium chloride, tetraoctylammonium bromide, tetraoctylammonium iodide, tetraoctylammonium hydroxide, methyltrioctylammonium chloride, methyltrioctylammonium bromide, methyltrioctylammonium iodide, methyltrioctylammonium hydroxide, benzyltrimethylammonium chloride, benzyltrimethylammonium bromide, benzyltriethylammonium chloride, benzyltributylammonium chloride, dibenzyldimethylammonium chloride, dibenzyldimethylammonium bromide, dibenzyldiethylammonium chloride and dibenzyldibutylammonium chloride.

6. A process for the preparation of a cyclic and bridging dialkoxy silane composition comprising at least one component having a chemical structure selected from the group consisting of:

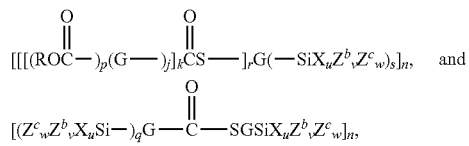

wherein:
each occurrence of the $-SiX_uZ^b{}_vZ^c{}_w$ group is independently selected from the group consisting of $-SiXZ^c$, $-SiZ^bZ^c$, $-SiX_2Z^b$, $-SiXZ^b{}_2$ and $-SiZ^b{}_3$;

each occurrence of R is independently selected from the group consisting of hydrogen, straight, cyclic or branched alkyl group, alkenyl group, aryl group, and aralkyl group, with each R, other than hydrogen, containing from 1 to 18 carbon atoms;

each occurrence of G is independently selected from the group consisting of hydrogen, a monovalent alkyl, alkenyl, aryl or aralkyl group containing from 1 to 30 carbon atoms, and a polyvalent group containing from 1 to 30 carbon atoms derived from alkyl, alkenyl, aryl or aralkyl group;

each occurrence of X is independently selected from the group consisting of $-Cl$, $-Br$, $R^1O-$, $R^1O(R^4CR^5)_fO-$, $R^1C(=O)O-$, $R^1R^2C=NO-$, $R^1R^2NO-$, $R^1R^2N-$, $-R^1$, and $-(OSi\ R^1R^2)_t(OSi\ R^1R^2R^3)$, wherein each occurrence of $R^1$, $R^2$ and $R^3$ is independently R;

each occurrence of $Z^b$, which forms a bridging structure between two different silicon atoms, is independently selected from the group consisting of $(-O-)_{0.5}$ and $[-O(R^4CR^5)_fO-]_{0.5}$, wherein each occurrence of $R^4$ and $R^5$ is independently R;

each occurrence of $Z^c$, which forms a cyclic structure with a single silicon atom, is independently given by $-O(R^4CR^5)_fO-$ wherein each occurrence of $R^4$ and $R^5$ is independently R;

each occurrence of the subscripts, u, n, v, w, f, p, r, q, j, p, t, and s, and k, is independently given by u is 0 to 3; n is 1 to 100, with the proviso that when n is greater than 1, v is greater than 0 and all the valences for $Z^b$ have a silicon atom bonded to them;

v is 0 to 3; w is 0 to 1 with the proviso that u+v+2w is 3; f is 1 to 15; p is 0 to 5; r is 1 to 3; q is 0 to 6; j is 0 to 1, with the proviso that when j is 0 p is 1; t is 0 to 50; s is 1 to 3; and k is 1 and wherein that each of the above structures comprise at least two hydrolysable bridging dialkoxy group, $Z^b$, or at least one hydrolysable cyclic dialkoxy group, $Z^c$, the process comprising reacting a thiocarboxylate-alkoxy silane having an alkoxysilyl moiety with a diol of the general formula:

$$HO(R^4CR^5)_fOH$$

in the presence of a catalyst to effect the transesterification of the alkoxysilyl moiety of the thiocarboxylate-alkoxy silane and provide the cyclic and bridging dialkoxy silane composition.

7. The process of claim 6 carried out in the presence of a catalyst which is an acid, base or transition metal-containing compound.

8. The process of claim 7, where the acid is selected from the group consisting of p-toluenesulfonic acid, sulfuric acid, hydrochloric acid, chlorosilanes, chloroacetic acid, phosphoric acid and mixtures thereof; the base is selected from the group consisting of sodium methoxide, sodium ethoxide and mixtures thereof; the transition metal-containing compound is selected from the group consisting of tetraisopropyl titanate, dibutyltin dilaurate, titanium alkoxides, titanium-containing chelates, zirconium alkoxides, zirconium-containing chelates and mixtures thereof.

9. The process of claim 6, wherein the catalyzed reaction of silane and diol is carried under distillation to remove volatile alcohol by-product.

10. The process of claim 6, wherein the diol is selected from the group consisting of 1,2-ethylene glycol, neopentyl glycol, 1,2-propanediol, 1,3-propanediol, 2-methyl-1,3-propanediol, 1,3-butanediol, 2-methyl-2,4-pentanediol, 1,4-butanediol, 1,6-hexanediol, cyclohexane dimethanol, pinacol and mixtures thereof.

11. The process of claim 6, where the reaction temperature is about 30 to about 90° C.

12. The process of claim 6, where the reaction pressure is about 1 to about 80 mm Hg absolute pressure.

13. The process of claim 6, wherein a molar ratio of at least about 0.5 moles of diol per alkoxy-silyl in the silane is employed.

14. The process of claim 6, further comprising:
a) reacting, in a thin film reactor, a thin film reaction medium comprising a thiocarboxylate-alkoxy silane, a diol and a catalyst to provide a diol-derived thiocarboxylate-alkoxy silane and a by-product alcohol;
b) vaporizing the by-product alcohol from the film to drive the reaction;
c) recovering the diol-derived thiocarboxylate-alkoxy silane reaction product;
d) optionally, recovering the by-product alcohol by condensation; and,
e) optionally, neutralizing the diol-derived thiocarboxylate-alkoxy silane product to improve its storage stability.

15. The process of claim 14, where the film is formed in a falling film evaporator device, a wiped film evaporator device or a distillation column.

* * * * *